(12) United States Patent
Rhee et al.

(10) Patent No.: US 12,193,996 B2
(45) Date of Patent: Jan. 14, 2025

(54) MONOCYTE COMPOSITIONS AND METHODS FOR THE TREATMENT OF INFECTIOUS DISEASE

(71) Applicants: The General Hospital Corporation, Boston, MA (US); President and Fellows of Harvard College, Cambridge, MA (US)

(72) Inventors: Catherine Rhee, Melrose, MA (US); David T. Scadden, Weston, MA (US)

(73) Assignees: The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 184 days.

(21) Appl. No.: 17/525,673

(22) Filed: Nov. 12, 2021

(65) Prior Publication Data

US 2022/0202855 A1    Jun. 30, 2022

Related U.S. Application Data

(60) Provisional application No. 63/112,848, filed on Nov. 12, 2020.

(51) Int. Cl.
| | | |
|---|---|---|
| *A61P 31/04* | (2006.01) | |
| *A61K 38/17* | (2006.01) | |
| *A61K 38/19* | (2006.01) | |
| *A61K 38/20* | (2006.01) | |
| *A61K 39/00* | (2006.01) | |

(52) U.S. Cl.
CPC ........ *A61K 38/1774* (2013.01); *A61K 38/191* (2013.01); *A61K 38/204* (2013.01); *A61K 39/4614* (2023.05); *A61K 39/4622* (2023.05); *A61K 39/464821* (2023.05); *A61K 39/464831* (2023.05); *A61P 31/04* (2018.01); *A61K 2239/31* (2023.05)

(58) Field of Classification Search
CPC .... A61K 35/15; A61K 31/04; A61K 38/1774; A61K 38/191; A61K 38/204
See application file for complete search history.

(56) References Cited

U.S. PATENT DOCUMENTS

2009/0068157 A1*  3/2009  Kamps ............... C12N 5/0645
                                                    435/456
2019/0076473 A1*  3/2019  Nguyen ............... A61P 31/04

OTHER PUBLICATIONS

Anders et al., "Count-based differential expression analysis of RNA sequencing data using Rand Bioconductor," Nat Protoc, 2013, 8:1765-1786.
Anders et al., HTSeq—a Python framework to work with high-throughput sequencing data. Bioinformatics, 2015, 31:166-169.
Bailey et al., "MEME Suite: tools for motif discovery and searching," Nucleic Acids Res, 2009, 37:W202-208.
Bhang et al., "Studying clonal dynamics in response to cancer therapy using high-complexity barcoding," Nat Med, 2015, 21:440-448, 13 pages.
Boyette et al., "Phenotype, function, and differentiation potential of human monocyte subsets," PLoS One, 2017, 12:e0176460, 20 pages.
Breslin et al., "Mouse blood monocytes: standardizing their identification and analysis using CD115," J Immunol Methods, 2013, 390:1-8.
Buenrostro et al., "ATAC-seq: A Method for Assaying Chromatin Accessibility Genome-Wide," Curr Protoc Mol Biol, 2015, 109:21. 29.1-21.29.9.
Buenrostro et al., "Integrated Single-Cell Analysis Maps the Continuous Regulatory Landscape of Human Hematopoietic Differentiation," Cell, 2018, 173:1535-1548.e1516, 31 pages.
Cao et al., "A specific role of integrin Mac-1 in accelerated macrophage efflux to the lymphatics," Blood, 2005, 106:3234-3241.
Chen et al., Enrichr: interactive and collaborative HTML5 gene list enrichment analysis tool, BMC Bioinformatics, 2013, 14:128, 14 pages.
Cros et al., "Human CD14dim monocytes patrol and sense nucleic acids and viruses via TLR7 and TLR8 receptors," Immunity, 2010, 33:375-386.
Cui et al., "High-Yield Human Induced Pluripotent Stem Cell-Derived Monocytes and Macrophages are Functionally Comparable with Primary Cells," Cell Dev Biol., Apr. 2021, 9:656867, 14 pages.
De Laval et al., "C/EBPbeta-Dependent Epigenetic Memory Induces Trained Immunity in Hematopoietic Stem Cells," Cell Stem Cell, 2020, 26:657-674.e658, 29 pages.
Dobin et al., "STAR: ultrafast universal RNA-seq aligner," Bioinformatics, 2013, 29:15-21, 7 pages.
Drevets et al., "Measurement of bacterial ingestion and killing by macrophages," Curr Protoc Immunol, 2015, 109:14.6.1-14.6.17.
Francke et al., "Generation of mature murine monocytes from heterogeneous bone marrow and description of their properties," J Histochem Cytochem, 2011, 59(9):813-825.
Frankenberg et al., "Phagocytosis-induced apoptosis of macrophages is linked to uptake, killing and degradation of bacteria," Eur J Immunol, 2008, 38(1):204-215.
Geissmann et al., "Development of monocytes, macrophages, and dendritic cells," Science, 2010, 327:656-661.
GenBank Accession No. NG_007149.1, "*Homo sapiens* BCL6 transcription repressor (BCL6), RefSeqGene on chromosome 3," dated Aug. 24, 2019, 10 pages.
GenBank Accession No. NG_007161.2, "*Homo sapiens* MYC proto-oncogene, bHLH transcription factor (MYC), RefSeqGene on chromosome 8," dated Aug. 28, 2019, 6 pages.
GenBank Accession No. NG_007457.1, "*Homo sapiens* MYCN proto-oncogene, bHLH transcription factor (MYCN), RefSeqGene on chromosome 2," dated Aug. 21, 2019, 7 pages.
GenBank Accession No. NG_008163.1, "*Homo sapiens* notch receptor 2 (NOTCH2), RefSeqGene on chromosome 1," dated Aug. 24, 2019, 42 pages.

(Continued)

*Primary Examiner* — Daniel E Kolker
*Assistant Examiner* — James Ryland Melchior
(74) *Attorney, Agent, or Firm* — Fish & Richardson P.C.

(57) ABSTRACT

Described herein are compositions comprising subsets of monocyte having distinct functional properties and methods for using the same to treat infectious disease.

6 Claims, 78 Drawing Sheets

Specification includes a Sequence Listing.

(56) References Cited

OTHER PUBLICATIONS

GenBank Accession No. NG_008377.1, "*Homo sapiens* cytochrome P450 family 2 subfamily A member 6 (CYP2A6), RefSeqGene on chromosome 19," dated Aug. 24, 2019, 6 pages.

GenBank Accession No. NG_008853.1, "*Homo sapiens* integrin subunit alpha 6 (ITGA6), RefSeqGene on chromosome 2," dated Aug. 24, 2019, 23 pages.

GenBank Accession No. NG_009016.1, "*Homo sapiens* fibroblast growth factor 3 (FGF3), RefSeqGene on chromosome 11," dated May 7, 2019, 6 pages.

GenBank Accession No. NG_011475.1, "*Homo sapiens* toll like receptor 4 (TLR4), RefSeqGene on chromosome 9," dated Jun. 4, 2019, 9 pages.

GenBank Accession No. NG_011719.1, "*Homo sapiens* integrin subunit alpha M (ITGAM), RefSeqGene (LRG_1333) on chromosome 16," dated Apr. 1, 2019, 24 pages.

GenBank Accession No. NG_012083.1, "*Homo sapiens* intercellular adhesion molecule 1 (ICAM1), RefSeqGene on chromosome 19," dated Jun. 2, 2019, 9 pages.

GenBank Accession No. NG_016412.1, "*Homo sapiens* integral membrane protein 2A (ITM2A), RefSeqGene on chromosome X," dated Aug. 24, 2019, 5 pages.

GenBank Accession No. NG_021169.1, "*Homo sapiens* NME/NM23 nucleoside diphosphate kinase 1 (NME1), RefSeqGene on chromosome 17," dated Jul. 29, 2019, 6 pages.

GenBank Accession No. NG_032897.1, "*Homo sapiens* platelet factor 4 (PF4), RefSeqGene on chromosome 4," dated Aug. 26, 2019, 5 pages.

GenBank Accession No. NG_033933.1, "*Homo sapiens* toll like receptor 9 (TLR9), RefSeqGene on chromosome 3," dated Nov. 24, 2018, 9 pages.

GenBank Accession No. NP_000116.2, "estrogen receptor isoform 1 [*Homo sapiens*]," dated Sep. 3, 2019, 4 pages.

GenBank Accession No. NP_076921.1, "homeobox protein Hox-B8 [*Homo sapiens*]," dated Jun. 11, 2019, 3 pages.

GenBank Accession No. P14778.1, "RecName: Full=Interleukin-1 receptor type 1; Short=IL-1R-1; Short=IL-1RT-1; Short=IL-1RT1; AltName: Full=CD121 antigen-like family member A; AltName: Full=Interleukin-1 receptor alpha; Short=IL-1R-alpha; AltName: Full=Interleukin-1 receptor type I; AltName: Full=p80; AltName: CD_antigen=CD121a; Contains: RecName: Full=Interleukin-1 receptor type 1, membrane form; Short=mIL-1R1; Short=mIL-1RI; Contains: RecName: Full=Interleukin-1 receptor type 1, soluble form; Short=sIL-1R1; Short=sIL-1RI; Flags: Precursor," dated Jun. 5, 2019, 9 pages.

GenBank Accession No. P26951.1, "RecName: Full=Interleukin-3 receptor subunit alpha; Short=IL-3 receptor subunit alpha; Short=IL-3R subunit alpha; Short=IL-3R-alpha; Short=IL-3RA; AltName: CD_antigen=CD123; Flags: Precursor," dated Jun. 5, 2019, 8 pages.

GenBank Accession No. Q03111.2, "RecName: Full=Protein ENL; AltName: Full=YEATS domain-containing protein 1," dated Sep. 18, 2019, 6 pages.

Ghisletti et al., "Identification and characterization of enhancers controlling the inflammatory gene expression program in macrophages," Immunity, Mar. 2010, 32(3):317-328.

Gordon and Taylor, "Monocyte and macrophage heterogeneity," Nat Rev Immunol, 2005, 5(12):953-964.

Gu et al., "Complex heatmaps reveal patterns and correlations in multidimensional genomic data," Bioinformatics, Sep. 2016, 32(18):2847-2849.

Hanna et al., "The transcription factor NR4A1 (Nur77) controls bone marrow differentiation and the survival of Ly6C-monocytes," Nat Immunol, Jul. 2011, 12(8):778-785, 11 pages.

Heinz et al., "Simple combinations of lineage-determining transcription factors prime cis-regulatory elements required for macrophage and B cell identities," Mol Cell, 2010, 38(4):576-589.

Horvath et al., "CRISPR/Cas, the immune system of bacteria and archaea," Science, Jan. 2010, 327(592):167-170.

Huang et al., "Systematic and integrative analysis of large gene lists using DAVID bioinformatics resources," Nat Protoc, 2009, 4(1):44-57.

Italiani and Boraschi, "From Monocytes to M1/M2 Macrophages: Phenotypical vs. Functional Differentiation," Front Immunol, Oct. 2014, 5:514, 22 pages.

Jakubzick et al., "Monocyte differentiation and antigen-presenting functions," Nat Rev Immunol, Jun. 2017, 17(6):349-362.

Kapellos et al., "Human Monocyte Subsets and Phenotypes in Major Chronic Inflammatory Diseases," Front Immunol, Aug. 2019, 10:2035, 13 pages.

Kleinnijenhuis et al., "Bacille Calmette-Guérin induces NOD2-dependent nonspecific protection from reinfection via epigenetic reprogramming of monocytes," Proc Natl Acad Sci USA, 2012, 109:17537-17542.

Koressaar and Remm, "Enhancements and modifications of primer design program Primer3," Bioinformatics, 2007, 23:1289-1291.

Li and Durbin, "Fast and accurate short read alignment with Burrows-Wheeler transform," Bioinformatics, 2009, 25(14):1754-1760.

Makarova et al., "A putative RNA-interference-based immune system in prokaryotes: computational analysis of the predicted enzymatic machinery, functional analogies with eukaryotic RNAi, and hypothetical mechanisms of action," Biology Direct, 2006, 1:7, 26 pages.

Medzhitov and Janeway, "Innate Immunity," N. Engl J Med, Aug. 2000, 343:338-344.

Menezes et al., "The Heterogeneity of Ly6C(hi) Monocytes Controls Their Differentiation into iNOS(+) Macrophages or Monocyte-Derived Dendritic Cells," Immunity, 2016, 45:1205-1218.

Mercier et al., "Single Targeted Exon Mutation Creates a True Congenic Mouse for Competitive Hematopoietic Stem Cell Transplantation: The C57BL/6-CD45.1(STEM) Mouse," Stem Cell Reports, 2016, 6:985-992.

Mildner et al., "Genomic Characterization of Murine Monocytes Reveals C/EBPbeta Transcription Factor Dependence of Ly6C(−) Cells," Immunity, 2017, 46:849-862.e7, 22 pages.

Mitroulis et al., "Modulation of Myelopoiesis Progenitors is an Integral Component of Trained Immunity," Cell, 2018, 172:147-161.e112, 29 pages.

Mulder et al., "Therapeutic targeting of trained immunity," Nat Rev Drug Discov, 2019, 18:553-566.

Narasimhan et al., "Nonclassical Monocytes in Health and Disease," Annu Rev Immunol, 2019, 37:439-456, 20 pages.

Netea et al., "Trained immunity: a memory for innate host defense," Cell Host Microbe, 2011, 9:355-361.

Olingy et al., "Monocyte heterogeneity and functions in cancer," J Leukoc Biol, 2019, 106:309-322.

Passlick et al., "Identification and characterization of a novel monocyte subpopulation in human peripheral blood," Blood, 1989, 74:2527-2534.

Patel et al., "The fate and lifespan of human monocyte subsets in steady state and systemic inflammation," J Exp Med, 2017, 214:1913-1923.

Paul et al., "Transcriptional Heterogeneity and Lineage Commitment in Myeloid Progenitors," Cell, 2015, 163:1663-1677.

Pennisi, "The CRISPR craze," Science, 2013, 341:833-836.

Pham et al., "Mechanisms of in vivo binding site selection of the hematopoietic master transcription factor PU.1," Nucleic Acids Res, 2013, 41(13):6391-6402.

Quinlan and Hall, "BEDTools: a flexible suite of utilities for comparing genomic features," Bioinformatics, 2010, 26(6):841-842.

Randolph et al., "Differentiation of phagocytic monocytes into lymph node dendritic cells in vivo," Immunity, 1999, 11:753-761.

Rhee et al., "Functionally distinct subsets of monocytes in mouse and human blood," Blood, 2019, 134(Suppl 1):438, 4 pages.

Rhee et al., "Rigidity of Cell Fate and Function Among Monocytes," Blood, 2021, 138(Suppl 1):2057-2058.

Robinson et al., "edgeR: a Bioconductor package for differential expression analysis of digital gene expression data," Bioinformatics, 2010, 26(1):139-140.

(56) References Cited

OTHER PUBLICATIONS

Saeed et al., "Epigenetic programming of monocyte-to-macrophage differentiation and trained innate immunity," Science, 2014, 345(6204):1251086, 13 pages.

Schauer et al., "Monocytes with angiogenic potential are selectively induced by liver resection and accumulate near the site of liver regeneration," BMC Immunol, 2014, 15:50, 10 pages.

Shi and Pamer, "Monocyte recruitment during infection and inflammation," Nat Rev Immunol, 2011, 11:762-774.

Swirski et al., "Identification of splenic reservoir monocytes and their deployment to inflammatory sites," Science, 2009, 325:612-616.

Sykes et al., "Inhibition of Dihydroorotate Dehydrogenase Overcomes Differentiation Blockade in Acute Myeloid Leukemia," Cell, 2016, 167:171-186.e115, 32 pages.

Thomas et al., "Human Blood Monocyte Subsets: A New Gating Strategy Defined Using Cell Surface Markers Identified by Mass Cytometry," Arterioscler Thromb Vasc Biol, 2017, 37:1548-1558, 15 pages.

Varol et al., "Monocytes give rise to mucosal, but not splenic, conventional dendritic cells," J Exp Med, 2007, 204:171-180.

Villani et al., "Single-cell RNA-seq reveals new types of human blood dendritic cells, monocytes, and progenitors," Science, 2017, 356(6335):eaah4573, 13 pages.

Wang et al., "Quantitative production of macrophages or neutrophils ex vivo using conditional Hoxb8," Nat Methods, 2006, 3(4):287-293.

Wiedenheft et al., "RNA-guided genetic silencing systems in bacteria and archaea," Nature, 2012, 482:331-8.

Xie et al., "Gene Set Knowledge Discovery with Enrichr," Curr Protoc, 2021, 1:e90, 51 pages.

Yáñez et al., "Granulocyte-Monocyte Progenitors and Monocyte Dendritic Cell Progenitors Independently Produce Functionally Distinct Monocytes," Immunity, 2017, 47:890-902.e894, 26 pages.

Yang et al., "Monocyte and macrophage differentiation: circulation inflammatory monocyte as biomarker for inflammatory diseases," Biomark Res, 2014, 2:1, 9 pages.

Yona et al., "Fate mapping reveals origins and dynamics of monocytes and tissue macrophages under homeostasis," Immunity, 2013, 38:79-91.

Wolf et al., "The Ontogeny of Monocyte Subsets," Front. Immunol., Jul. 2019, 10:1642, 8 pages.

\* cited by examiner

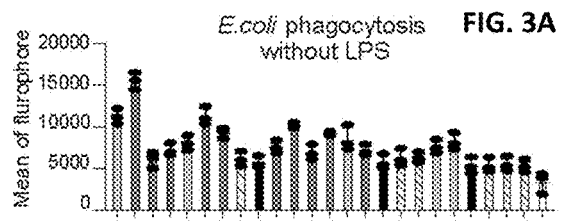
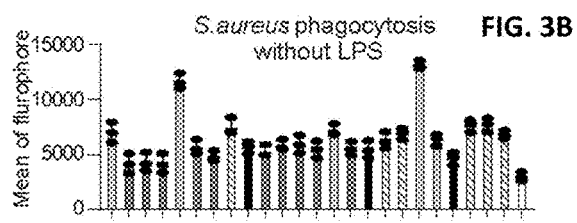
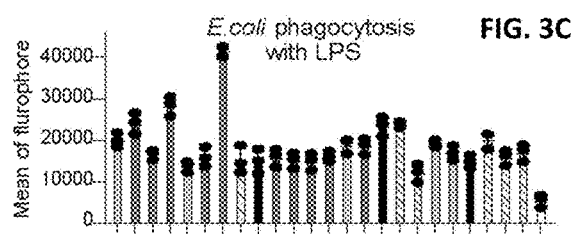
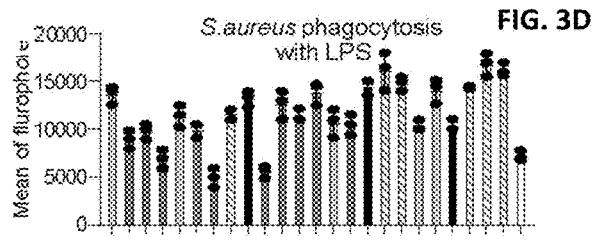
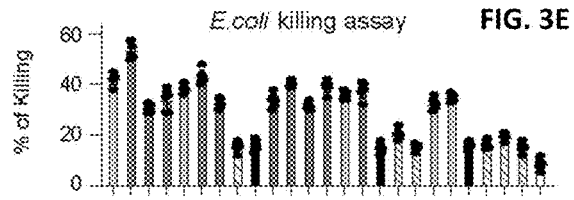
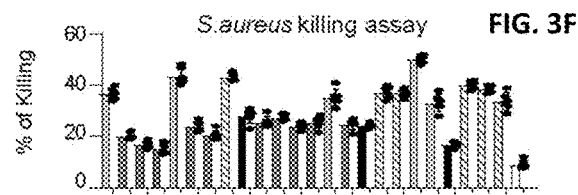
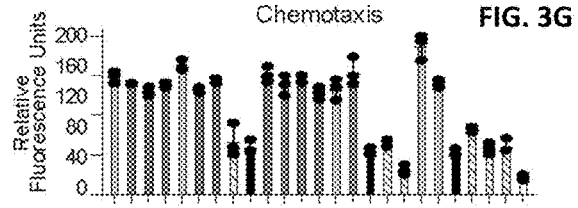
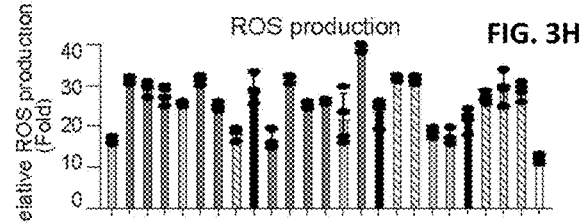
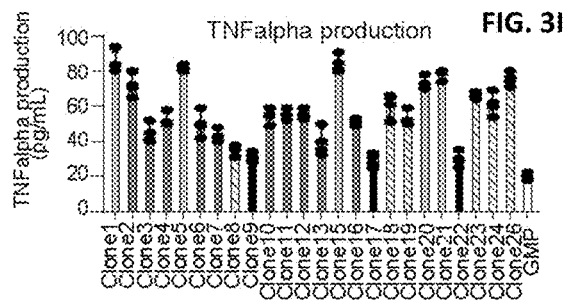
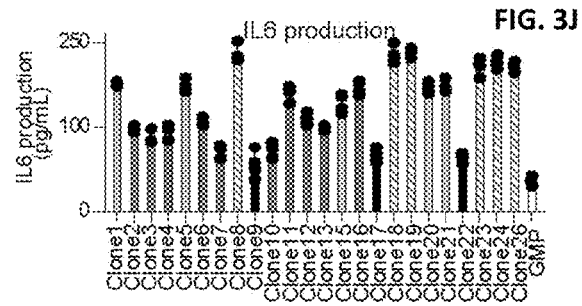

| Motif in blueprint ATACseq peaks | Motif (TF) | E-value |
|---|---|---|
| [logo] | KLF9 | 5.7e-16 |
| [logo] | BACH2<br>MAF::NFE2 | 5.9e-8 |
| [logo] | SP1<br>ZNF263<br>SP2 | 2.9e-4 |

FIG. 6I

MONOCYTE COMPOSITIONS AND METHODS FOR THE TREATMENT OF INFECTIOUS DISEASE

CLAIM OF PRIORITY

This application claims the benefit of U.S. Patent Application No. 63/112,848 filed on Nov. 12, 2020. The entire contents of the foregoing are incorporated herein by reference.

FEDERALLY SPONSORED RESEARCH

This invention was made with government support under Grant No. HL131477 awarded by the National Institutes of Health. The government has certain rights in the invention.

SEQUENCE LISTING

This application contains a Sequence Listing that has been submitted electronically as an ASCII text file named "Sequence Listing.txt." The ASCII text file, created on Feb. 4, 2022, is 23 kilobytes in size. The material in the ASCII text file is hereby incorporated by reference in its entirety.

BACKGROUND OF THE INVENTION

Myeloid cells are the most evolutionarily ancient aspect of a specialized immune system and the cornerstone of innate immunity in vertebrates. Innate immunity serves at the front line of host defense playing essential roles in directly clearing infection while also activating adaptive immune cell populations (Medzhitov and Janeway, 2000). Among myeloid cells, monocytes play a pivotal role in innate immunity as phagocytes, cytokine producers and sources of antigen presenting cells that patrol the blood and assume tissue resident sites (Frankenberg et al., 2008; Italiani and Boraschi, 2014; Jakubzick et al., 2017; Olingy et al., 2019).

In adults, monocytes differentiate from granulocyte-monocyte progenitors (GMPs) in the bone marrow and migrate from the bloodstream to other tissues where they differentiate into macrophages (Geissmann et al., 2010). Numerous studies have demonstrated that mouse monocytes can be isolated in the murine blood by Cd115, a receptor for the macrophage growth factor M-CSF (Breslin et al., 2013; Francke et al., 2011). Murine monocytes are grouped into two subsets based on their immunophenotypes and functions (Gordon and Taylor, 2005; Narasimhan et al., 2019; Yang et al., 2014). 'Inflammatory' classical monocytes co-express Lytic, Ccr2, and L-selectin, and are selectively recruited to inflamed tissues to secrete large quantities of TNF-alpha and IL-1 in response to damage. 'Resident and patrolling' non-classical monocytes highly express Cx3cr1, Lfal, and Cd43, and dynamically patrol the vascular endothelium during steady-state and inflammation. In parallel, three distinct human monocyte subsets were identified based on the expression of CD14 and CD16, named classical, intermediate, and non-classical subsets (Boyette et al., 2017; Kapellos et al., 2019; Passlick et al., 1989; Patel et al., 2017). Classical monocytes are thought to readily convert to non-classical monocytes with high responsiveness to exogenous cues (Yona et al., 2013) and dependent upon expression of transcription factors such as C/EBPβ (Mildner et al., 2017) and Nr4a1 (Hanna et al., 2011). However, this conversion is still controversial (Geissmann et al., 2010; Shi and Pamer, 2011; Varol et al., 2007; Yona et al., 2013).

Several recent studies have utilized unbiased single cell RNA-sequencing and high-dimensional mass cytometry analysis to map heterogenous human circulating monocytes (Thomas et al., 2017; Villani et al., 2017). These studies highlighted increased monocytic heterogeneity compared to the previous classification, based on the expression of cell surface markers and combination of myeloid-related genes, but the subsets are of unclear functional consequence. Other studies have employed similar high-throughput sequencing technologies to study GMP heterogeneity (Paul et al., 2015; Yanez et al., 2017). It has previously been shown that different progenitors, GMPs and MDPs, independently produce functionally distinct monocytes (Yanez et al., 2017). It has also been reported that differences of PU.1 levels in naïve monocytes lead to distinct microbicidal or dendritic cell differentiation upon stimulation (Ghisletti et al., 2010; Menezes et al., 2016; Pham et al., 2013). However, it has been extensively shown that monocytes are readily induced to acquire functional features dependent on physiological needs (Cros et al., 2010; Schauer et al., 2014; Swirski et al., 2009) supporting a prevailing model that monocytes are highly plastic, able to interconvert based on environmental factors.

Optimizing methods to isolate monocyte subsets with enhanced antimicrobial properties would enable new clinical methods of cell-based therapy to treat infectious disease.

SUMMARY OF THE INVENTION

It has now been determined that monocytic subsets exist with inherent, restricted capabilities which differ in their capacity to perform traditional monocytic functions. The subsets were identifiable by immunophenotype among primary monocytes and have distinctive in vivo capabilities in responding to and clearing infectious agents following adoptive transfer. Subsets of monocytes were classified based on epigenetics, transcriptomics, and function that responded distinctly to microbial infection (e.g., bacterial infection).

In one aspect, the invention provides a method of treating a microbial infection in a tissue of a subject, the method comprising administering to the subject a composition comprising isolated monocyte cells that express Cd49f, Cd54, and Cd11b, thereby treating the microbial infection in the tissue of the subject.

In one embodiment, the microbial infection in the tissue of the subject is bacterial, gram negative bacterial, or fungal and is caused by a local or systemic infection of *E. coli, S. aureus* or *Candida* spp.

In another embodiment, the cells express an increased level of Bcl6, Tlr4, Tlr9, Notch2 and Il1r1, and secrete an increased level of cytokines IL6 and TNF alpha compared to classical and non-classical monocytes.

In yet another embodiment, the cells express an increased level of Myc, Mllt1 and Mycn and exhibit preferential expansion in the presence of GM-CSF compared to classical and non-classical monocytes.

In yet another embodiment, the cells express an increased level of Cyp2a5 and produce an increased level of ROS compared to classical and non-classical monocytes.

In yet another embodiment, the cells express an increased level of Nme1, Fgf3, Itm2a, Pf4, and Il3ra and secrete an increased level of cytokines IL6 and TNF alpha compared to classical and non-classical monocytes.

In yet another embodiment, the cells comprise exogenous nucleic acid sequences recombined into their genomic DNA.

In yet another embodiment, the exogenous nucleic acid sequences encode ER-Hoxb8.

In yet another embodiment, the cells comprise transiently expressed exogenous nucleic acid sequences.

In another aspect, the invention provides a composition comprising isolated monocytic cells that express Cd49f, Cd54, and Cd11b and comprise exogenous nucleic acid sequences recombined into their genomic DNA.

In one embodiment, the exogenous nucleic acid sequences encode ER-Hoxb8 and comprise nucleic acid sequences having at least 85% (e.g., 86%, 87%, 88%, 89%, 90%, 91%, 92%, 93%, 94%, 95%, 96%, 97%, 98%, 99%, or 100%) sequence identity to the nucleic acid sequence of SEQ ID NO: 1 or 2.

In another embodiment, the cells further express an increased level of Bcl6, Tlr4, Tlr9, Notch2 and Il1r1, and secrete an increased level of cytokines IL6 and TNF alpha compared to classical and non-classical monocytes.

In yet another embodiment, the cells further express an increased level of Myc, Mllt1 and Mycn and exhibit preferential expansion in the presence of GM-CSF compared to classical and non-classical monocytes.

In yet another embodiment, the cells further express an increased level of Cyp2a5 and produce an increased level of ROS compared to classical and non-classical monocytes.

In yet another embodiment, the isolated monocytic cells further express an increased level of Nme1, Fgf3, Itm2a, Pf4 and secrete an increased level of cytokines IL6 and TNF alpha compared to classical and non-classical monocytes.

Other features and advantages of the invention will be apparent from the Detailed Description, and from the claims. Thus, other aspects of the invention are described in the following disclosure and are within the ambit of the invention.

BRIEF DESCRIPTION OF THE DRAWINGS

The following Detailed Description, given by way of example, but not intended to limit the invention to specific embodiments described, may be understood in conjunction with the accompanying figures, incorporated herein by reference.

FIGS. 6A-I. Depicts monocyte subsets primed epigenetically at the level of progenitor cells. (A) PCA plot of chromatin accessibility at ATAC-seq peaks in progenitors and monocytes ATAC-seq reveals distinct patterns of chromatin accessibility among GMP progenitors. (B) PCA of chromatin accessibility patterns in progenitors, with points colored grouped by functional classes of monocytes. (C) Representative genomic tracks of ATAC-seq tag density near cKit and Cd11b genes with similar chromatin accessibility across all classes (boxed). (D) Representative genomic tracks of differential ATAC-seq tag density between classes (boxed). (E) Gene expression is associated with chromatin openness in GMP. Plots of genome wide chromatin accessibility calculated as moving averages of ATAC-seq signal in a sliding window (window size, 55; bin size, 1), sorted by gene expression. (F) Scatter plots of RNA expression differences against chromatin accessibility differences between Class1 and Class2 as a representative example. (G) Representative genomic tracks of class-specific differences in enhancer chromatin accessibility among GMPs that precede the corresponding class-specific differences in gene expression among mature monocytes. (H) Class-specific monocyte expression signatures preceded by GMP enhancer differences are enriched in key functional gene categories. (I) Enriched transcription factor binding motifs among GMP enhancers with class-specific differential ATAC-seq peaks that precede class-specific monocyte gene expression. See FIGS. 5A-F.

DETAILED DESCRIPTION OF THE INVENTION

Definitions

Figure 1A:
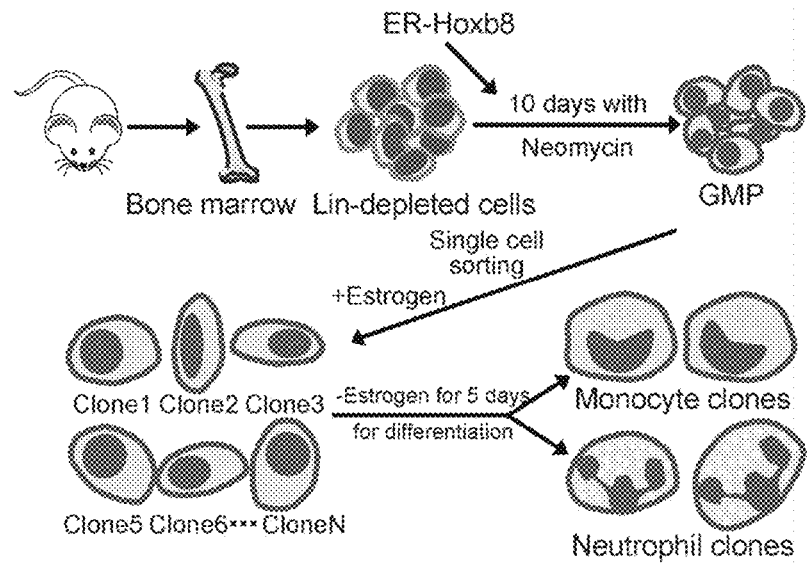
FIGS. 1A-I. Depicts monocytic cells having clone-specific behaviors that can be classified into functional groups. (A) Experimental scheme of conditional myeloid differentiation. (B) Representative FACS plots showing cell fates of ER-Hoxb8 clones. (C) Representative FACS plots showing monocytes derived from ER-Hoxb8 can emigrate and reside in tissues after injection into the blood (n=3 independent experiments, in triplicate technical replicates). (D) Experimental scheme of functional assays to evaluate heterogeneity within monocytic ER-Hoxb8 clones. (E) Heatmap showing monocytic clones have clone-specific behaviors that can be classified into four functional groups. (F) Radar plots showing the functional abilities of monocyte ER-Hoxb8 clones in vitro. (G) Bar graphs showing in vivo phagocytosis of ER-Hoxb8 monocytes using fluorescently labelled heat-killed bacteria (n=4 independent experiments, in triplicate biological replicates). (H) Bar graphs showing in vivo killing assay of ER-Hox8b monocytes using live bacteria (n=4 independent experiments, in triplicate biological replicates). (I) Heatmap showing in vivo functional assays correlate with in vitro data. *P<0.05, P<0.01, and *P<0.005. See FIGS. 2-3.

Unless otherwise defined, all technical and scientific terms used herein have the same meaning as commonly understood by one of ordinary skill in the art to which this invention belongs. In case of conflict, the present application, including definitions will control.

A "subject" is a vertebrate, including any member of the class mammalia, including humans, domestic and farm animals, and zoo, sports or pet animals, such as mouse, rabbit, pig, sheep, goat, cattle and higher primates.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "effective amount" is meant the amount of monocyte cells that produce the desired antimicrobial therapeutic response.

By "isolated" is meant a material that is free to varying degrees from components which normally accompany it as found in its native state. "Isolate" denotes a degree of separation from original source or surroundings.

The term "allogeneic", as used herein, refers to deriving from, originating in, or being members of the same species, where the members are genetically related or genetically unrelated but genetically similar. An "allogeneic transplant" refers to transfer of cells or organs from a donor to a recipient, where the recipient is the same species as the donor.

As used herein, the term "autologous" refers to deriving from or originating from the same subject or patient. An "autologous transplant" refers to the harvesting and reinfusion or transplant of a subject's own cells or organs.

As used herein, the term "exogenous nucleic acid sequence" refers to a non-genomic nucleic acid sequence, such as an added copy of a gene or genes that is introduced into a cell and becomes integrated into the genomic DNA of the cell.

As used herein "an increase" refers to an amount or level that is at least about 0.05 fold more (for example 0.1, 0.2, 0.3, 0.4, 0.5, 1, 5, 10, 25, 50, 100, 1000, 10,000-fold or more) than an amount or level compared to a reference level. "Increased" as it refers to an amount or level also means at least about 5% more (for example 5, 6, 7, 8, 9, 10, 15, 20, 25, 30, 35, 40, 45, 50, 55, 60, 65, 70, 75, 80, 85, 90, 95, 99 or 100% more) than an amount or level compared to a reference level. Amounts of gene expression, cytokine production or cell expansion can be measured according to methods known in the art. Reference levels can be determined using Classical and Non-classical monocytes as described, for example, by Boyette et al., 2017; Kapellos et al., 2019; Passlick et al., 1989; Patel et al., 2017.

Unless specifically stated or clear from context, as used herein, the term "about" is understood as within a range of normal tolerance in the art, for example within 2 standard deviations of the mean. "About" is understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Compositions and Methods of the Invention

Four monocyte subsets which express cell surface markers Cd49f, Cd54, and Cd11b and differ in their capacity to perform traditional monocytic functions can be identified through clonal expansion, functional gene expression profiles (Huang da et al., 2009) and functional assays described herein. The subsets are distinguishable by immunophenotype among primary monocytes and have enhanced capabilities in responding to and clearing infectious agents, including but not limited to gram negative bacteria such as *E. coli*, and *S. aureus*, and *Candida* spp, following adoptive transfer.

Class 1 monocytes express an increased level of inflammatory response genes and toxic response genes, and secrete an increased level of cytokines IL6 and TNF alpha compared to classical and non-classical monocytes. Inflammatory response genes and toxic response genes include, but are not limited to, Bcl6 (Genbank Accn. No. NG 007149.1), Tlr4 (Genbank Accn. No. NG 011475.1), Tlr9 (Genbank Accn No. NG 033933.1), Notch2 (NG 008163.1) and Il1r1 (Genbank Accn. No. P14778.1).

Class 2 monocytes express an increased level of DNA repair genes and exhibit preferential expansion in the presence of GM-CSF compared to classical and non-classical monocytes (the cells thrive the presence of GM-CSF whereas other growth factors are not as effective). DNA repair genes include, but are not limited to, Myc (Genbank Accn. No. NG_007161.2), Mllt1 (Genbank Accn. No. Q03111.2) and Mycn (Genbank Accn. No. NG_007457.1).

Class 3 monocytes express an increased level of bacterial inflammatory defense genes and acute-phase response genes and produce an increased level of ROS compared to classical and non-classical monocytes. Class 3 monocytes are also more efficient in killing *E. coli* than classical and non-classical monocytes. Inflammatory bacterial defense genes and acute-phase response genes include, but are not limited to, Cyp2a5 (Genbank Accn. No. NG008377.1).

Class 4 monocytes express an increased level of immune response genes and viral defense genes and secrete an increased level of cytokines IL6 and TNF alpha compared to classical and non-classical monocytes. Class 4 monocytes are also more efficient in killing *E. coli* than classical and non-classical monocytes. Immune response genes and viral defense genes include, but are not limited to, Nme1 (Genbank Accn No. NG021169.1), Fgf3 (Genbank Accn No. NG009016.1), Itm2a (Genbank Accn No. NG016412.1), Pf4 (Genbank Accn No. NG032897.1), and Il3ra (Genbank Accn No. P26951.1).

Isolation of the monocyte subsets of the invention can be achieved using multiple approaches. In one embodiment, inducible clonal expansion of primary mouse granulocyte-monocyte progenitors (GMP) capable of differentiating into mature myeloid cells can be generated in a system adapted from Sykes et al., 2016 and Wang et al., 2006. Primary murine bone marrow cells can be transduced with a nucleic acid encoding a fusion protein comprising an estrogen-binding domain of estrogen receptor (ERBD, or ER), optionally with a Gly400Val mutation, fused to Hoxb8. Such nucleic acids are referred to herein as ER-Hoxb8 fusion constructs, and can include a tag, e.g., at the N and/or C terminus, such as a tagged ER-Hoxb8 construct, e.g., an HA-tagged ER-Hoxb8 construct or a Flag-tagged ER-Hoxb8 construct. Exemplary HA tag sequences can comprise YPYDVPDYA (SEQ ID NO: 30), and exemplary FLAG tag sequences can comprise DYKDDDDK (SEQ ID NO:31). In some embodiments, the fusion proteins can comprise an EE epitope tag (EEYMPME, SEQ ID NO:32). Exemplary human ER ligand binding domains include amino acids 310-547 or 282-595 of GenBank Acc. No. NP 000116.2 (e.g., as shown in SEQ ID NO: 26 and 27, respectively). Exemplary human Hoxb8 sequences can comprise amino acids 2-243 of NP_076921.1 (e.g., SEQ ID NO:28). The fusion constructs can include a linker, e.g., a glycine-serine linker, between the ER and the Hoxb8. Linkers can be, e.g., 1-50 amino acids, and are typically flexible and do not interfere with binding or activity of the ER or the Hoxb8.

An HA-tagged ER-Hoxb8 construct can comprise a nucleic acid sequence having at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) sequence identity to the nucleic acid sequence of SEQ ID NO: 1. An HA-tagged ER-Hoxb8 construct can be generated by PCR using: 5' primers that comprise nucleic acid sequences having at least 80% sequence identity to the nucleic acid sequence of SEQ ID NO: 5; and 3' primers that comprise nucleic acid sequences having at least 80% sequence identity to the nucleic acid sequence of SEQ ID NO: 7.

A Flag-tagged ER-Hoxb8 construct can comprise a nucleic acid sequence having at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) sequence identity to the nucleic acid sequence of SEQ ID NO: 2. A Flag-tagged ER-Hoxb8 construct can be generated by PCR using: 5' primers that comprise nucleic acid sequences having at least 80% sequence identity to the nucleic acid sequence of SEQ ID NO: 6; and 3' primers that comprise nucleic acid sequences having at least 80% sequence identity to the nucleic acid sequence of SEQ ID NO: 7. Table 1 provides nucleic acid sequences tagged-ER Hoxb8 constructs (e.g., HA-tagged ER-Hoxb8 construct and Flag-tagged ER-Hoxb8 construct) and tags (e.g., HA tag and Flag tag); ER, Hoxb8, and ER-Hoxb8 fusion proteins; and primers used for generating such constructs. In some embodiments, the ER-Hoxb8 fusion proteins comprise a sequence having at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) sequence identity to amino acids 14-75 of SEQ ID NO: 29 (i.e., lacking the HA tag shown in SEQ ID NO:29).

TABLE 1

Exemplary sequences

| Description | Sequence | Sequence Identifier |
|---|---|---|
| HA-tagged ER-Hoxb8 construct | GCTCTCTTCCTCATCCGCCCCGTCTCTCCCCCT<br>TGAACCTCCTCGTTCGACCCCGCCTCGATCCTCCCTTT<br>ATCCAGCCCTCACTCCTTCTCTAGGCGCCGGAATTCG<br>CCACCATGGGATACCCATACGATGTTCCGGATTACGC<br>TACGCGTTCTGCTGGAGACATGAGAGCTGCCAACCTT<br>TGGCCAAGCCCGCTCATGATCAAACGCTCTAAGAAGA<br>ACAGCCTGGCCTTGTCCCTGACGGCCGACCAGATGGT<br>CAGTGCCTTGTTGGATGCTGAGCCCCCCATACTCTATT<br>CCGAGTATGATCCTACCAGACCCTTCAGTGAAGCTTC<br>GATGATGGGCTTACTGACCAACCTGGCAGACAGGGA<br>GCTGGTTCACATGATCAACTGGGCGAAGAGGGTGCCA<br>GGCTTTGTGGATTTGACCCTCCATGATCAGGTCCACCT<br>TCTAGAATGTGCCTGGCTAGAGATCCTGATGATTGGT<br>CTCGTCTGGCGCTCCATGGAGCACCCAGTGAAGCTAC<br>TGTTTGCTCCTAACTTGCTCTTGGACAGGAACCAGGG<br>AAAATGTGTAGAGGGCATGGTGGAGATCTTCGACATG<br>CTGCTGGCTACATCATCTCGGTTCCGCATGATGAATCT<br>GCAGGGAGAGGAGTTTGTGTGCCTCAAATCTATTATT<br>TTGCTTAATTCTGGAGTGTACACATTTCTGTCCAGCAC<br>CCTGAAGTCTCTGGAAGAGAAGGACCATATCCACCGA<br>GTCCTGGACAAGATCACAGACACTTTGATCCACCTGA<br>TGGCCAAGGCAGGCCTGACCCTGCAGCAGCAGCACC<br>AGCGGCTGGCCCAGCTCCTCCTCATCCTCTCCCACATC<br>AGGCACATGAGTAACAAAGGCATGGAGCATCTGTAC<br>AGCATGAAGTGCAAGAACGTGGTGCCCCTCTATGACC<br>TGCTGCTGGAGATGCTGGACGCCCACCGCCTACATGC<br>GCCCACTAGCCGTGGAGGGGCATCCGTGGAGGAGAC<br>GGACCAAAGCCACTTGGCCACTGCGGGCTCTACTTCA<br>TCGCATTCCTTGCAAAAGTATTACATCACGGGGGAGG<br>CAGAGGGTTTCCCTGCCACAGTCACGCGTGGAAGCTC<br>TTATTTCGTCAACTCACTGTTCTCCAAATACAAAACCG<br>GGGAGTCCCTGCGCCCCAATTATTATGACTGCGGCTT<br>CGCCCAGGACCTGGGCGGCCGACCCACCGTGGTGTAC<br>GGTCCCAGCAGCGGCGGCAGCTTCCAGCACCCTTCGC<br>AAATCCAGGAGTTCTACCACGGGCCATCGTCGCTGTC<br>CACAGCTCCCTACCAGCAGAACCCGTGCGCCGTGGCG<br>TGCCACGGCGACCCCGGCAACTTCTACGGCTACGACC<br>CTCTGCAGCGCCAGAGCCTGTTCGGTGCGCAGGATCC<br>AGACCTGGTGCAGTACGCAGACTGCAAGCTCGCGGC<br>AGCCAGCGGCCTGGGCGAGGAGGCCGAGGGGTCTGA<br>GCAGAGCCCGTCGCCCACACAGCTCTTTCCCTGGATG<br>CGCCCTCAAGCCGCCGGACGCAGGCGAGGCCGCCAG<br>ACCTACAGTCGCTACCAGACCCTGGAGCTGGAGAAG<br>GAGTTCCTATTTAATCCCTATCTGAATCGCAAGCGGA<br>GGATCGAGGTATCGCACGCGCTGGGACTGACAGAGA<br>GACAGGTCAAAATCTGGTTCCAGAATCGGAGAATGA<br>AGTGGAAAAAGGAGAACAACAAAGACAAGTTTCCCA<br>GCAGTAAATGCGAGCAGGAGGAGCTGGAGAAAGAGA<br>AGCTGGNGCGGGCACCAGAGACCGCCGAGCAGGGCG<br>ATGCGCAGAAGGGTGACAAGANNGTAGTAACTCGAG | SEQ ID NO: 1 |
| Flag-tagged Hoxb8 construct | GCTCTCTTCCTCATCCGCCCCGTCTCTCCCCCT<br>TGAACCTCCTCGTTCGACCCCGCCTCGATCCTCCCTTT<br>ATCCAGCCCTCACTCCTTCTCTAGGCGCCGGAATTCG<br>CCACCATGGACTACAAGGACGACGATGACAAAGGAA<br>CGCGTTCTGCTGGAGACATGAGAGCTGCCAACCTTTG<br>GCCAAGCCCGCTCATGATCAAACGCTCTAAGAAGAAC<br>AGCCTGGCCTTGTCCCTGACGGCCGACCAGATGGTCA<br>GTGCCTTGTTGGATGCTGAGCCCCCCATACTCTATTCC<br>GAGTATGATCCTACCAGACCCTTCAGTGAAGCTTCGA<br>TGATGGGCTTACTGACCAACCTGGCAGACAGGGAGCT<br>GGTTCACATGATCAACTGGGCGAAGAGGGTGCCAGG<br>CTTTGTGGATTTGACCCTCCATGATCAGGTCCACCTTC<br>TAGAATGTGCCTGGCTAGAGATCCTGATGATTGGTCT<br>CGTCTGGCGCTCCATGGAGCACCCAGTGAAGCTACTG<br>TTTGCTCCTAACTTGCTCTTGGACAGGAACCAGGGAA<br>AATGTGTAGAGGGCATGGTGGAGATCTTCGACATGCT<br>GCTGGCTACATCATCTCGGTTCCGCATGATGAATCTG<br>CAGGGAGAGGAGTTTGTGTGCCTCAAATCTATTATTT<br>TGCTTAATTCTGGAGTGTACACATTTCTGTCCAGCACC<br>CTGAAGTCTCTGGAAGAGAAGGACCATATCCACCGA<br>GTCCTGGACAAGATCACAGACACTTTGATCCACCTGA<br>TGGCCAAGGCAGGCCTGACCCTGCAGCAGCAGCACC<br>AGCGGCTGGCCCAGCTCCTCCTCATCCTCTCCCACATC<br>AGGCACATGAGTAACAAAGGCATGGAGCATCTGTAC | SEQ ID NO: 2 |

TABLE 1-continued

Exemplary sequences

| Description | Sequence | Sequence Identifier |
|---|---|---|
| | AGCATGAAGTGCAAGAACGTGGTGCCCCTCTATGACC<br>TGCTGCTGGAGATGCTGGACGCCCACCGCCTACATGC<br>GCCCACTAGCCGTGGAGGGGCATCCGTGGAGGAGAC<br>GGACCAAAGCCACTTGGCCACTGCGGGCTCTACTTCA<br>TCGCATTCCTTGCAAAAGTATTACATCACGGGGGAGG<br>CAGAGGGTTTCCCTGCCACAGTCACGCGTGGAAGCTC<br>TTATTTCGTCAACTCACTGTTCTCCAAATACAAAACCG<br>GGGAGTCCCTGCGCCCCAATTATTATGACTGCGGCTT<br>CGCCCAGGACCTGGGCGCCGACCCACCGTGGTGTAC<br>GGTCCCAGCAGCGGCGGCAGCTTCCAGCACCCTTCGC<br>AAATCCAGGAGTTCTACCACGGGCCATCGTCGCTGTC<br>CACAGCTCCCTACCAGCAGAACCCGTGCGCCGTGGCG<br>TGCCACGGCGACCCCGGCAACTTCTACGGCTACGACC<br>CTCTGCAGCGCCAGAGCCTGTTCGGTGCGCAGGATCC<br>AGACCTGGTGCAGTACGCAGACTGCAAGCTCGCGGC<br>AGCCAGCGGCCTGGGCGAGGAGGCCGAGGGGTCTGA<br>GCAGAGCCCGTCGCCCACACAGCTCTTTCCCTGGATG<br>CGCCCTCAAGCCGCCGGACGCAGGCGAGGCCGCCAG<br>ACCTACAGTCGCTACCAGACCCTGGAGCTGGAGAAG<br>GAGTTCCTATTTAATCCCTATCTGAATCGCAAGCGGA<br>GGATCGAGGTATCGCACGCGCTGGGACTGACAGAGA<br>GACAGGTCAAAATCTGGTTCCAGAATCGGAGAATGA<br>AGTGGAAAAAGGAGAACAACAAAGACAAGTTTCCCA<br>GCAGTAAATGCGAGCAGGAGGAGCTGGAGAAAGAGA<br>AGCTGGNGCGGGCACCAGAGACCGCCGAGCAGGGCG<br>ATGCGCAGAAGGGTGACAAGANNGTAGTAACTCGAG | |
| HA tag for HA-ER-Hoxb8 construct | GAATTCGCCACCATGGGATACCCATACGATGT<br>TCCGGATTACGCTACGCGT | SEQ ID NO: 3 |
| Flag tag for Flag-ER-Hoxb8 construct | GAATTCGCCACCATGGACTACAAGGACGACGA<br>TGACAAAGGAACGCGT | SEQ ID NO: 4 |
| 5' primer (HA tag) for tagged Hoxb8 construct | g gaa ttc gcc acc ATG GGA TAC CCA TAC GAT GTT CCG GAT TAC GCT ACG CGT GGA *AGC TCT TAT TTC GTC AAC TCA C* | SEQ ID NO: 5 |
| 5' primer (FLAG tag) for tagged Hoxb8 construct | g gaa ttc gcc acc ATG *GAC TAC AAG GAC GAC GAT GAC AAA GGA* ACG CGT GGA *AGC TCT TAT TTC GTC AAC TCA C* | SEQ ID NO: 6 |
| 3' primer for tagged Hoxb8 constructs | ccg ctc gag tta CTA *CTT CTT GTC ACC CTT CTG CG* | SEQ ID NO: 7 |
| Human estrogen receptor ligand-binding domain, amino acids 310-547 of NP_000116.2 with Gly400V mut | TADQMVSALLDAEPPILYSEYDPTRPFSEASMMG<br>LLTNLADRELVHMINWAKRVPGFVDLTLHDQVHLLEC<br>AWLEILMIGLVWRSMEHPVKLLFAPNLLLDRNQGKCVE<br>GMVEIFDMLLATSSRFRMMNLQGEEFVCLKSIILLNSGV<br>YTFLSSTLKSLEEKDHIHRVLDKITDTLIHLMAKAGLTLQ<br>QQHQRLAQLLLILSHIRHMSNKGMEHLYSMKCKNVVPL<br>YDLLLEMLDAH | SEQ ID NO: 26 |
| Human estrogen receptor ligand-binding domain, amino acids 282-595 of NP_000116.2 with Gly400V mut | SAGDMRAANLWPSPLMIKRSKKNSLALSLTADQ<br>MVSALLDAEPPILYSEYDPTRPFSEASMMGLLTNLADRE<br>LVHMINWAKRVPGFVDLTLHDQVHLLECAWLEILMIGL<br>VWRSMEHPVKLLFAPNLLLDRNQGKCVEGMVEIFDML<br>LATSSRFRMMNLQGEEFVCLKSIILLNSGVYTFLSSTLKS<br>LEEKDHIHRVLDKITDTLIHLMAKAGLTLQQQHQRLAQ<br>LLLILSHIRHMSNKGMEHLYSMKCKNVVPLYDLLLEML<br>DAHRLHAPTSRGGASVEETDQSHLATAGSTSSHSLQKY<br>YITGEAEGFPATV | SEQ ID NO: 27 |
| Human homeobox protein Hox-B 8, amino acids 2-243 of NP_076921.1 | SSYFVNSLFSKYKTGESLRPNYYDCGFAQDLGG<br>RPTVVYGPSSGGSFQHPSQIQEFYHGPSSLSTAPYQQNPC<br>AVACHGDPGNFYGYDPLQRQSLFGAQDPDLVQYADCK<br>LAAASGLGEEAEGSEQSPSPTQLFPWMRPQAAAGRRRG<br>RQTYSRYQTLELEKEFLFNPYLTRKRRIEVSHALGLTER<br>QVKIWFQNRRMKWKKENNKDKFPSSKCEQEELEKQKL | SEQ ID NO: 28 |

TABLE 1-continued

Exemplary sequences

| Description | Sequence | Sequence Identifier |
|---|---|---|
| | ERAPEAADEGDAQKGDKK | |
| HA-ER-Hoxb8 fusion protein | MGYPYDVPDYATRSAGDMRAANLWPSPLMIK RSKKNSLALSLTADQMVSALLDAEPPILYSEYDPTRPFSE ASMMGLLTNLADRELVHMINWAKRVPGFVDLTLHDQV HLLECAWLEILMIGLVWRSMEHPVKLLFAPNLLLDRNQ GKCVEGMVEIFDMLLATSSRFRMMNLQGEEFVCLKSIIL LNSGVYTFLSSTLKSLEEKDHIHRVLDKITDTLIHLMAK AGLTLQQQHQRLAQLLLILSHIRHMSNKGMEHLYSMKC KNVVPLYDLLLEMLDAHRLHAPTSRGGASVEETDQSHL ATAGSTSSHSLQKYYITGEAEGFPATVTRGSSYFVNSLFS KYKTGESLRPNYYDCGFAQDLGGRPTVVYGPSSGGSFQ HPSQIQEFYHGPSSLSTAPYQQNPCAVACHGDPGNFYG YDPLQRQSLFGAQDPDLVQYADCKLAAASGLGEEAEGS EQSPSPTQLFPWMRPQAAGRRRGRQTYSRYQTLELEKE FLFNPYLNRKRRIEVSHALGLTERQVKIWFQNRRMKWK KENNKDKFPSSKCEQEELEKEKLXRAPETAEQGDAQKG DKXVVTR | SEQ ID NO: 29 |

Primary murine bone marrow cells transduced with an ER-Hoxb8 fusion construct described herein (e.g., a tagged ER-Hoxb8 fusion construct encoded by a a nucleic acid sequence having at least 80% sequence identity to the nucleic acid sequence of SEQ ID NO: 1 or 2, or an untagged sequence, optionally comprising a sequence that is at least 80% identical to amino acids 14-75 of SEQ ID NO: 29 (lacking the HA or FLAG tag)) and maintained in the presence of an estrogen agonist, self-renew indefinitely as GMPs. These GMPs can be isolated by single cell sorting and propagated as clones in the presence of beta-estradiol (estrogen). Withdrawal of estrogen inactivates the ER-Hoxb8 protein and allows for terminal myeloid differentiation of GMP clones into either monocytes or neutrophils over the course of approximately 5 days, confirmed by their cell surface markers and morphology. In some embodiments, the ER-Hoxb8 fusion construct stably integrates into the genome of the GMPs and remains present in subsequent generations including within terminally differentiated monocytes of the disclosure. Accordingly, the present disclosure provides GMPs and subsequent generations thereof (including, e.g., terminally differentiated monocytes) that have exogenous nucleic acid sequences recombined into their genomic DNA. Such exogenous nucleic acid sequences may encode ER-Hoxb8 and comprise nucleic acid sequences having at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) sequence identity to the nucleic acid sequence of SEQ ID NO: 1 or 2.

Alternatively, the ER-Hoxb8 fusion construct can be transiently expressed from exogenous nucleic acid sequences. In some embodiments, the primary murine bone marrow cells can be stably or transiently transduced with alternative or additional transcription factors, such as HoxA9, or epigenetic modifiers whose expression can induce hematopoietic stem and progenitor cell self-renewal prior to terminal myeloid differentiation of GMP clones.

Each of the four monocyte subsets express cell surface markers Cd49f, Cd54, and Cd11b. Cd49f (Genbank Accn No. NG_008853.1) is an integrin known for cell surface adhesion and signaling. Cd11b (Genbank Accn No. NG_011719.1) is a myeloid cell integrin receptor for complement, fibrinogen, and endothelial cell ICAM-1. Cd54 (Genbank Accn No. NG_012083.1) is intercellular adhesion molecule 1 (ICAM1) known to bind to Cd11a and Cd11b. Isolation of the monocyte subsets of the invention can additionally be achieved by selecting for cells within the bone marrow that exhibit Cd49f and Cd54 expression. Antibodies directed against the gene products of Cd49f and Cd54 can be used in FACS analysis to purify the cells from among other populations of cells within the bone marrow, as well as other mixed populations of cells comprising the monocyte subsets of the invention. The purified population of Cd49f and Cd54 expressing monocytic cells can be about 50 to about 55%, about 55 to about 60%, about 65 to about 70%, about 70 to about 75%, about 75 to about 80%, about 80 to about 85%, about 85 to about 90%, about 90 to about 95% or about 95 to about 100% of the cells in the composition.

iPS cells are adult cells that have been genetically reprogrammed to an embryonic stem cell-like state by being forced to express genes and factors important for maintaining the defining properties of embryonic stem cells. Established protocols can be used to differentiate iPS cells into monocytes (Cui, D. et al. High-Yield Human Induced Pluripotent Stem Cell-Derived Monocytes and Macrophages are Functionally Comparable with Primary Cells. Cell Dev Biol. 2021 Apr. 13; 9:656867). Cd49f and Cd54 positive monocytes of the invention can be identified from within a population of differentiated monocytes by FACs cell sorting and further characterized, as needed, by the methods described below for analyzing gene expression and other functional properties.

In some embodiments, Cd49f and Cd54 positive monocytes of the invention can be genetically altered to express desired nucleic acids according to methods known in the art, including all methods known to introduce transient and stable changes of the cellular genetic material. Genetic alteration includes the addition of exogenous genetic material. Exogenous genetic material includes nucleic acids or oligonucleotides, either natural or synthetic that are introduced into the cells.

Gene editing systems can be used to achieve genetic alteration of mesenchymal stromal cells, stem or progenitor cells. For example, the CRISPR/Cas system can be used to inactivate one or more nucleic acids (Wiedenheft et al. (2012) Nature 482: 331-8). The CRISPR/Cas system has been modified for use in gene editing (silencing, enhancing or changing specific genes) in eukaryotes such as mice or primates. This is accomplished by, for example, introducing into the eukaryotic cell a plasmid containing a specifically designed CRISPR and one or more appropriate Cas. CRISPR/Cas systems for gene editing in eukaryotic cells typically involve (1) a guide RNA molecule (gRNA) comprising a targeting sequence (which is capable of hybridizing to the genomic DNA target sequence), and sequence which is capable of binding to a Cas, e.g., Cas9 enzyme, and (2) a Cas, e.g., Cas9, protein. The targeting sequence and the sequence which is capable of binding to a Cas, e.g., Cas9 enzyme, may be disposed on the same or different molecules. If disposed on different molecules, each includes a hybridization domain which allows the molecules to associate, e.g., through hybridization.

The CRISPR sequence, sometimes called a CRISPR locus, comprises alternating repeats and spacers. RNA from the CRISPR locus is constitutively expressed and processed into small RNAs. These comprise a spacer flanked by a repeat sequence. The RNAs guide other Cas proteins to silence exogenous genetic elements at the RNA or DNA level. Horvath et al. (2010) Science 327: 167-170; Makarova et al. (2006) Biology Direct 1: 7. The spacers thus serve as templates for RNA molecules, analogously to siRNAs. Pennisi (2013) Science 341: 833-836.

The CRISPR/Cas system can thus be used to modify, e.g., delete one or more nucleic acids, e.g., CD248 or a gene regulatory element of CD248, or introduce a premature stop which thus decreases expression of a functional CD248. The CRISPR/Cas system can alternatively be used like RNA interference, turning off the CD248 in a reversible fashion. In a mammalian cell, for example, the RNA can guide the Cas protein to a promoter of CD248 or Cdh11, sterically blocking RNA polymerases.

In other embodiments, the exogenous genetic material may also include a naturally occurring gene which has been placed under operable control of a promoter in an expression vector construct. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that can incorporate and deliver the recombinant polynucleotide.

The present invention provides methods of treating infectious disease and/or disorders or symptoms thereof (e.g., sepsis) which comprise administering a therapeutically effective amount of a composition comprising the Cd49f and Cd54 positive monocytes described herein to a subject (e.g., a mammal, such as a human). Thus, one embodiment is a method of treating a subject having a disease characterized by a *S. aureus* or *E. coli* infection. The method includes the step of administering to the subject an effective amount of Cd49f and Cd54 positive monocytes or a mixture comprising such cell types, in an amount sufficient to treat a disease or disorder or symptom thereof, under conditions such that the disease or disorder is treated. Identifying a subject in need of such treatment can be in the judgment of a subject or a health care professional and can be subjective (e.g. opinion) or objective (e.g. measurable by a test or diagnostic method).

A composition comprising Cd49f and Cd54 positive monocytes can be administered according to methods known in the art. Such compositions may be administered by any conventional route, including injection or by gradual infusion over time. The administration may, depending on the composition being administered, for example, be, intrathymic, pulmonary, intravenous, intraperitoneal, intramuscular, intracavity, subcutaneous, or transdermal. The Cd49f and Cd54 positive monocytes are administered in "effective amounts", or the amounts that either alone or together with further doses produces the desired therapeutic response. Administered cells of the invention can be autologous ("self") or non-autologous ("non-self," e.g., allogeneic, syngeneic or xenogeneic). Generally, administration of the cells can occur within a short period of time following treatment (e.g. 1, 2, 5, 10, 24 or 48 hours after treatment) and according to the requirements of each desired treatment regimen.

Cd49f and Cd54 positive monocytes can be combined with pharmaceutical excipients known in the art to enhance preservation and maintenance of the cells prior to administration. In some embodiments, cell compositions of the invention can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the cells utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

A method to potentially increase cell survival when introducing the cells into a subject in need thereof is to incorporate cells of interest into a biopolymer or synthetic polymer. Depending on the subject's condition, the site of injection might prove inhospitable for cell seeding and growth because of scarring or other impediments. Examples of biopolymer include, but are not limited to, cells mixed with fibronectin, fibrin, fibrinogen, thrombin, collagen, and proteoglycans. This could be constructed with or without included expansion or differentiation factors. Additionally, these could be in suspension, but residence time at sites subjected to flow would be nominal. Another alternative is a three-dimensional gel with cells entrapped within the interstices of the cell biopolymer admixture. Again, expansion or differentiation factors could be included with the cells. These could be deployed by injection via various routes described herein.

Those skilled in the art will recognize that the components of the compositions should be selected to be chemically inert and will not affect the viability or efficacy of the stem cells or their progenitors as described in the present invention. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of cells is the quantity of cells necessary to achieve an optimal effect. Different scenarios may require optimization of the amount of cells injected into a tissue of interest. Thus, the quantity of cells to be administered will vary for the subject being treated. The precise determination of what would be considered an effective dose may be based on factors individual to each patient, including their size, age, sex, weight, and condition of the particular patient. As few as 100-1000 cells can be administered for certain desired applications among selected patients. Therefore, dosages can be readily ascertained by those skilled in the art from this disclosure and the knowledge in the art.

The skilled artisan can readily determine the amount of cells and optional additives, vehicles, and/or carrier in compositions and to be administered in methods of the invention. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

The present invention is additionally described by way of the following illustrative, non-limiting Examples that provide a better understanding of the present invention and of its many advantages.

EXAMPLES

The following Examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following Examples do not in any way limit the invention.

To address the issue of monocyte heterogeneity, plasticity, and whether the functional monocytes are due to induction or selection, a model system that allowed expansion and control of the differentiation of individual GMPs ex vivo was utilized. It was then determined whether GMP clones with molecular and immunophenotypic distinctions differentiated into monocytes with specialized functions. Functional, transcriptomic and epigenomic analyses of GMP clones and their monocyte descendants revealed four GMP differentiation trajectories that yield functionally distinct monocytes. Notably these groups were evident at the GMP level based on unsupervised clustering of chromatin configuration data. The differentiation fate of the monocyte descendants was epigenetically scripted in their progenitors and this fate had little flexibility once differentiation had begun. Testing cells under in vitro and in vivo homeostasis and stress conditions suggests that the cells maintain their differentiation path and do not transition from one state to another. These data imply a model whereby monocyte stimulus-specific selection may occur and may contribute to an innate immune memory that resembles adaptive immune memory.

The Materials and Methods used to conduct the assays in the following Examples are described in detail herein below.

Data and code availability: All sequencing data including RNA-seq and ATAC-seq data that support the findings of this study have been deposited in NCBI GEO with the accession codes GSE 176050.

Generation of ER-Hoxb8 GMP cell lines: Primary murine bone marrow was harvested from a mouse by crushing the femur and tibia bones. The cells were filtered through a 40-μm filter and layered over a Ficoll-Paque PLUS gradient to collect live cells. Cells were cultured for 48 hours in RPMI medium supplemented with 10% FBS, penicillin/streptomycin, stem cell factor (SCF; 10 ng/ml), interleukin (IL)-3 (10 ng/ml), and IL-6 (10 ng/ml). Tissue-culture-treated 6-well plates were pre-coated with human plasma fibronectin for overnight at 37° C. (10 μg/ml). Fibronectin was aspirated prior to the addition of cells. At 48 hours, $2.5 \times 10^5$ cells were transferred to each well. Polybrene was added, and the cells were transduced with ectopic retrovirus (MSCVneo-EE-ER-HoxB8) via spinoculation (1,000×g, 90 min, 22° C.). Following transduction, fresh media was added to each well to dilute the polybrene to a less toxic concentration.

ER-HoxB8 cells were maintained in RPMI medium supplemented with 10% FBS, penicillin/streptomycin, and SCF. The source of SCF was conditioned media generated from a Chinese hamster ovary (CHO) cell line. Conditioned medium was added at a final concentration of 1%-2% (depending on the batch, the final concentration of SCF was approximately 100 ng/ml as measured by ELISA). Beta-estradiol (E2, Sigma, E2758) was added to a final concentration of 0.5 μM from a 10-mM stock dissolved in 100% ethanol. After 10 days of maintenance, the cells were FACs sorted into 96 well plates with culture media, for further analysis.

Injection of ER-Hoxb8 cell lines into mice: 20 million live cells were injected into recipient mice (conditioned with 4.5 Gy or 6.0 Gy or 9.5 Gy 24 hours prior to injection of cells) intravenously or intraperitoneally.

Cytospins and Wright-Giemsa staining: Cells were prepared in PBS at a concentration of approximately 2 million cells/ml. Cytospin (Thermo Scientific Shandon) preparations were made (1,000 RPM, 60 sec), and the cells were air dried. Cells were stained in 100% Wright-Giemsa (Siemens) for 2 min, and in 20% Wright-Giemsa diluted in buffer for 12 min. Stained cells were rinsed in deionized water, and coverslips were affixed with Permount prior to microscopy.

Flow cytometry and FACS: Cells were suspended in FACS buffer (PBS+2% FBS) with appropriate antibodies and stained for 30 min at 4° C. in the dark. For mouse and human primary cells, incubation with FcBlock for 10 min at 4° C. prior to antibody staining was required. For intracellular staining (TNFalpha, IL6, Annexin, and Ki67), the cells were fixed and performed for intracellular staining after antibody staining using Fixation/Permeabilization solution kit (554714, BD Biosciences). 7-AAD or DAPI was included as a viability dye when applicable. Flow cytometry data was collected on either a BD Aria or BD LSR2 flow cytometer and analyzed using FlowJo software.

Quantitative gene expression analysis: For RT-qPCR, total RNA was isolated using the RNeasy Plus Mini Kit (Qiagen). 500 ng total RNA was then used to synthesize RT-qPCR was performed using One-Step RT-qPCR reagents (BioRad). Using Primer 3 (Koressaar and Remm, 2007) RT-qPCR primers were designed to amplify an ~100 bp region containing the junction between two exons if applicable. The Ct values obtained from qPCR were normalized against Gapdh for gene expression.

TABLE 2

Primer sequences for qPCR

| Gene | Primer F | Primer R |
|---|---|---|
| Adgre1 | GCACCATGTTAGCTGCTCTTC (SEQ ID NO: 8) | TGGACTCATTCTCCTTGCACT (SEQ ID NO: 9) |
| Itgax | TGGGGTTTGTTTCTTGTCTTG (SEQ ID NO: 10) | AACCACCACCCAGGAACTATC (SEQ ID NO: 11) |
| Itgam | CTTCACGGCTTCAGAGATGAC (SEQ ID NO: 12) | TTGATCTGAACAGGGATCCAG (SEQ ID NO: 13) |
| Fcgr1 | ACAGTGGCGAATACAGGTGTC (SEQ ID NO: 14) | GGGTTCTCCTTCTGTGAGGAC (SEQ ID NO: 15) |
| Csf1r | ATCACCCAAAGGGCCATATAC (SEQ ID NO: 16) | ATTATTCCAGCCTGCCTTGTT (SEQ ID NO: 17) |
| H2-Ab1 | GAAAGGCATTTCGTGTACCAG (SEQ ID NO: 18) | ACTCCTCCCGGTTGTAGATGT (SEQ ID NO: 19) |
| Icam1 | CTTGGTAGAGGTGACTGAGGAGTT (SEQ ID NO: 20) | GTTGTAGACTGTTAAGGTCCTCTGC (SEQ ID NO: 21) |
| Itga6 | CTGAATTCAAATGAAGCCAAAAC (SEQ ID NO: 22) | TCCTTCTCGGGTACCAAATTTAT (SEQ ID NO: 23) |
| Gapdh | AAATTCAACGGCACAGTCAAG (SEQ ID NO: 24) | CACCCCATTTGATGTTAGTGG (SEQ ID NO: 25) |

Phagocytosis assay: For ER-Hoxb8 cells, the cells were differentiated in culture media without E2 for 5 days. For primary monocytes, the cells were sorted from mouse bone marrow. The cells were resuspended in fresh media along with fluorescein-labeled heat-killed $E.\ coli$ or $S.\ aureus$ BioParticles (Molecular Probes). For in vitro assays, the cells and bioparticles were agitated gently at 37° C. for 60 min (with or without LPS), followed by FACS analysis. For in vivo assays, the cells were injected into lethally irradiated (9.5Gy) mice with bioparticles intravenously or interperitoneally. Blood of the mice were collected 60 min post injection, followed by FACS analysis. For human in vitro assays, sorted human peripheral blood cells and bioparticles were mixed together at 37° C. for 60 min, followed by FACS analysis.

Bacterial killing assay: For ER-Hoxb8 cells, the cells were differentiated in culture media without E2 for 5 days. For primary monocytes, the cells were sorted from mouse bone marrow. The cells were resuspended in fresh media along with live $E.\ coli$ or $S.\ aureus$ (ATCC) that were grown in tryptic soy broth. For in vitro assays, the monocytes and bacterial cells ($1\times10^4$ CFU in 200 ul) were incubated at 37° C. for 60 min. The cells are then plated onto tryptic soy plates in a serial dilution. Bacterial colonies on the plates were counted the following day. For in vivo assays, the monocytes were injected intraperitoneally into lethally irradiated mice with live bacteria ($1\times10^8$ CFU in 200 ul). After 60 min of bacterial infection, the cells were collected from peritoneum cavity followed by plating onto tryptic soy plates as in vitro assays. For human in vitro assays, sorted human peripheral blood cells and live bacteria were mixed together at 37° C. for 60 min, followed by plating onto tryptic soy plates.

Bacterial infection: Primary mouse monocytes were collected followed by infection similar to the bacterial killing assays. Instead of plating the cells onto tryptic soy plates, flow cytometry of the cells was used to examine their immunophenotype.

Chemotaxis: Chemotaxis assay kit (Cell Biolabs) was used for chemotaxis analysis. 5 μm pore size was used, and the manufacturer's instructions were followed.

Cytokine ELISA: Mouse ELISA kits from R&D Systems were used to measure both TNFα and IL-6 cytokine secretion. The manufacturer's instructions were followed.

Reactive Oxygen Species (ROS) assay: H2DCFDA (H2-DCF, DCF) from ThermoFisher Scientific (D399) was used according to the manufacturer's instructions. The cells were incubated with H2DCFDA at 37° C. for 30 min in culture media, followed by addition of LPS at 37° C. for 30 min. Then, flow cytometry was used to collect the data.

Cytokine intracellular staining: Cells were fixed using fixation buffer (BioLegend) in the dark for 20 min at room temperatures. The cells were centrifuged at 500×g for 5 min, and the supernatant was aspirated. Fixed cells were washed in Intracellular Staining Perm Wash Buffer (BioLegend) and resuspended with antibody of interest in the dark at room temperature for 60 min. The cells were washed in Intracellular Staining Perm Wash Buffer and resuspended in FACS buffer followed by FACS analysis.

Proliferation assay: The Cell Counting Kit-8 from Dojindo (CK04-11) was used to measure proliferation rates over the course of 4 days of culture in media without E2.

Mice tissue analysis: Blood cells were collected retroorbitally using two capillary tubes while mice were anesthetizing with isoflurane, or by bleeding tail veins directly into EDTA coated tubes. Bone marrow cells were harvested by crushing the femur, tibia, and spines, and cell suspensions were filtered through a 40-μm filter. Peritoneal cavity cells were collected using 21 gauge needles after injection of 7 mL PBS into peritoneum using 25 gauge needles. Other tissues of mice were collected after perfusion of mice with 20 mL of PBS. Spleen, liver, kidney cells were mashed on a 40-μm filter. Lung cells were cut into small pieces using a blade and scissors, followed by digestion with digestion buffer (FACS buffer+2.5 mg/mL dispase+1 mg/mL collagenase type II). The lung cells were incubated at 37° C. for 60 min, and cells were passed through a 40-μm filter. All tissue cells were subjected to ACK lysis buffer for 5 min at room temperature to remove contaminating red blood cells.

Gene-expression analysis: Libraries were prepared with an RNA library preparation kit (E7490, NEB) using 1 µg of RNA for ER-Hoxb8 cells and SMARTer Stranded RNA-seq Kit (634839, Takara) using RNA obtained by the RNeasy Mini Kit (Qiagen). RNA-seq libraries were sequenced with a 1×50-bp strand-specific protocol on a NextSeq (Illumina). RNA-seq reads were mapped to the ENSEMBL annotation of mouse transcriptome (mm9 reference genome) using STAR v2.7.3a (Dobin et al., 2013). Read counts for individual genes were produced using the un-stranded count feature in HTSeq v.0.6.0 (Anders et al., 2015). Differential expression analysis was performed using the EdgeR package (Robinson et al., 2010) after normalizing read counts and including only genes with count per million reads (CPM) >1 for one or more samples (Anders et al., 2013). Differentially expressed genes were defined based on the criteria of >2-fold change in expression value and false discovery rate (FDR)<0.01 unless otherwise specified. Heatmap and PCA plots were created using R packages ComplexHeatmap (Gu et al., 2016) and ggplot2, respectively. Analysis of gene set enrichment was performed using Enrichr (Chen et al., 2013).

Gene Ontology (GO) analysis: DAVID 6.7 (Huang da et al., 2009) was used for analysis of differentially expressed genes obtained from the expression profile data.

Chromatin accessibility analysis: ATAC assays were performed as previously described (Buenrostro et al., 2015). Approximately ~50,000 ER-Hoxb8 GMP and monocytic cells were used. The cells were incubated with transposition reaction mix for 30 min followed by PCR reaction for 18 cycles. ATAC-seq was performed using Illumina NextSeq 2000 instrument resulting in 40-50 million reads per sample. ATAC-seq reads were aligned to mm9 mouse reference genome using BWA v0.7.17 (Li and Durbin, 2009) with command bwa sample. Peaks were called using the HOMER. (Heinz et al., 2010) method with default parameters. ATAC-seq tag density was calculated as reads per kilobase per million (RPKM) using Bedtools v2.27.1 (Quinlan and Hall, 2010) at TSS-proximal promoter regions of all genes (TSS+/−3 Kb) and at enhancer regions defined as ATAC-seq peaks outside of promoter regions. Genes were linked to enhancers based on closest TSS within 1 Mb from the enhancer. Analysis of sequence motif enrichment among enhancer and promoter sets was performed using MEME-ChIP (Bailey et al., 2009). To generate a PCA in FIG. 3B, outlier clones were removed.

Lineage tracing experiment: Primary GMPs from C57BL/6-Tg(UBC-GFP)30Schaa (004353, Jackson) or C57BL/6-CD45.1(STEM) (Mercier et al., 2016) were sorted followed by transduction with a high-complexity barcode library, pRSI9-U6-(sh)-UbiC-TagRFP-2A-Puro (67267, Addgene). The barcoded GMP cells were then transferred into stable, sub-lethally (6Gy), or lethally (9.5Gy) irradiated C57BL/6 mice (000664, Jackson) and allowed to differentiate for 72 hours or 7 days prior to isolation of blood monocytes. The cells were collected from bone marrow, spleen, and/or lung, depending on the experiment settings. The monocytes were sorted into the four different classes of primary monocytes based on the Cd49f and Cd54 analytic schema and GFP+ TagRFP+ or Cd45.1+TagRFP+ Cells in each class were then processed for DNA sequencing. Previous publication methods (Bhang et al., 2015) were followed for DNA sequencing preparation and analysis.

Comparison between RNAseq and ATACseq: Gene expressions and promoter chromatin accessibility at the corresponding genes were used to address relationship between transcriptome and chromatin accessibility.

BrdU incorporation assay: Mice were injected using 250 ul of BrdU (10 mg/mL, 552598, BD Biosciences), followed by analyzing the primary mouse monocytes by flow cytometry.

Cell cultures of primary cells: To culture the primary mouse cells, 1 mL of IMDM medium (10-016-CV, Corning) supplemented with 10% FBS and penicillin/streptomycin was used
in 12 well plates. M-CSF (5 ug, AF-315-02, Peprotech), GM-CSF (50 ug, 315-03, Peprotech), or IL3 (50 ug) was added as a supplement. The cells were cultured for 4 days at 37° C. followed by analysis using flow cytometry.

Peptidoglycan assay: Peptidoglycans (PGN) were purchased from InvivoGen (tlrl-ksspgn and tlrl-sipgn). For in vitro assay, ER-Hoxb8 GMP cells were incubated with 10 ng/mL of PGN during differentiation. For in vivo training assay, mice were exposed with PGN (1 mg in 0.1 mL of saline) intraperitoneally, 72 hours prior to the experiment.

Human peripheral blood preparation: Human peripheral blood was purchased from Stemcell. For each experiment, 40-60 mL of peripheral blood was purchased, 20 mL from each donor. Red blood cells were lysed using ACK lysis buffer for 10 min at 4° C., and analyzed by flow cytometry.

Survival rate assay: The animals were monitored every 12 hours up to 14 days of infection for signs of moribundity and mortality, if any.

List of Antibodies: For mouse, Ly6C (1:100, 128030, Biolegend), Ly6G (1:100, 561236/551461, BD Biosciences), Cd11b (1:100, 564443, BD Biosciences), Cd115 (1:100, 135510/135513, Biolegend), F4/80 (1:100, 123118, Biolegend), Cd49f (1:50, 313622, Biolegend), Cd54 (1:100, 740855, BD Biosciences), cKit (1:100, 564011, BD Biosciences, 105820, Biolegend), Cd45.2 (1:100, 564616, BD Biosciences, 109836, Biolegend, 12-0454-83, Invitrogen), Cd45.1 (1:100, 565212, BD Biosciences, 110731/110741/110722, Biolegend), IL6 (1:100, 504508, Biolegend), TNF-alpha (1:100, 506305/506329, Biolegend), Annexin (1:100, 560566, Biolegend), Fc/Block (1:50, 553141, BD Biosciences), MHCII (1:100, 107620, Biolegend), Lin (1:100, Cd8a, Cd3e, Cd45R/B220, Cd4, Cd11b, Ly6G/C, Ter119, BD Biosciences), Ki67 (1:100, 556027, BD Biosciences), Cx3cr1 (1:100, 149006, Biolegend), Ccr2 (1:100, 747972, BD Biosciences), Cd43 (1:100, 143215, Biolegend), Cd4 (1:100, 17-0041-83, eBioscience), Cd11c (1:100, 117306, Biolegend), Cd123 (1:100, 17-1231-81, eBioscience), Cd16/32 (1:50, 101318, Biolegend), Streptavidin (1:250, 563262, BD Bioscience), Cd34 (1:25, 560230, BD Bioscience), Sca1 (1:100, 1081218, Biolegend), 7-AAD (1:50, 51-68981E, BD Biosciences), DAPI (1:5000, 422801, Biolegend) were used.

For human, CD235 (1:50, 306614, Biolegend), CD45 (1:100, 563792, BD Biosciences), CD11b (1:100, 564443, BD Biosciences), HLA-DR (1:50, 307618, Biolegend), CD15 (1:50, 323034, Biolegend), CD14 (1:25, 301834, Biolegend), CD16 (1:50, 302038, Biolegend), CD49F (1:50, 313622/313616, Biolegend), CD54 (1:100, 740978, BD Biosciences), CD64 (1:50, 305032, Biolegend), Fc/Block (1:50, 564219, BD Biosciences), CD56 (1:25, 318335, Biolegend), CD3 (1:25, 300464, Biolegend), CD19 (1:25, 302246, Biolegend) were used.

Mouse strains: For the experiments in the study, C57BL/6J (000664, Jackson), C57BL/6-Tg(UBC-GFP)30Schaa (004353, Jackson), B6.Cg-Tg(CAG-DsRed*MST)1Nagya (006051, Jackson), B6.129(ICR)-Tg(CAG-ECFP)CK6Nagya (004217, Jackson), C57BL/6-CD45.1(STEM) (Mercier et al., 2016), B6.129S4-Ccr2tm1Ifc/J (004999, Jackson), B6; 129S2-Nr4a1tm1Jmi/J (006187, Jackson) were used. Only females that are 6-16 weeks old were used for the experiments.

Statistical analysis: Two-way ANOVA, non-parametric t tests, or hypergeometric tests were done, depending on the experiments.

Figure 1B:
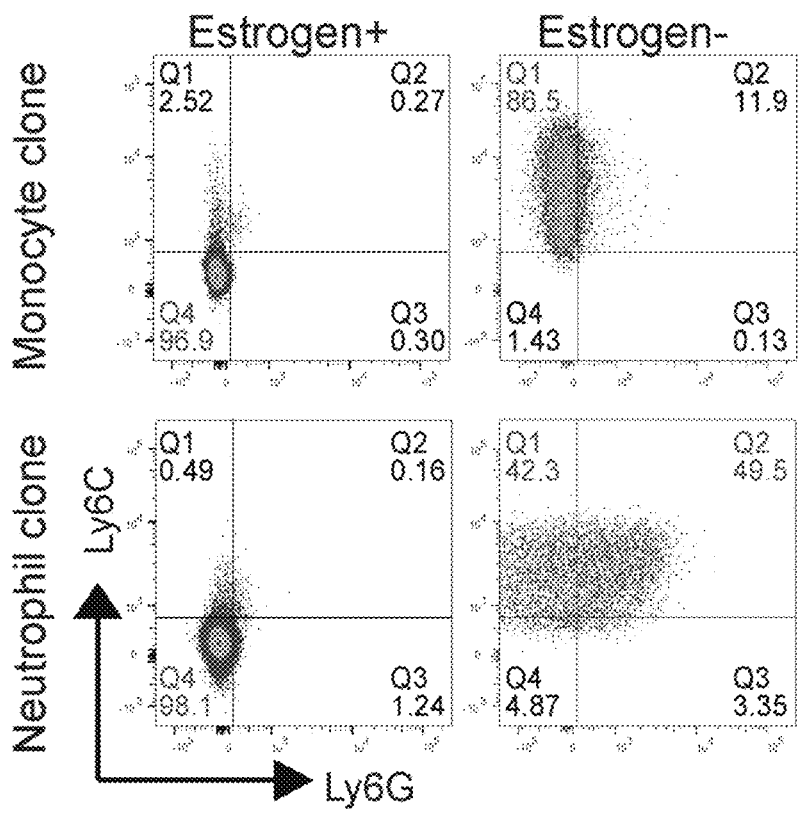
Figure 1C:
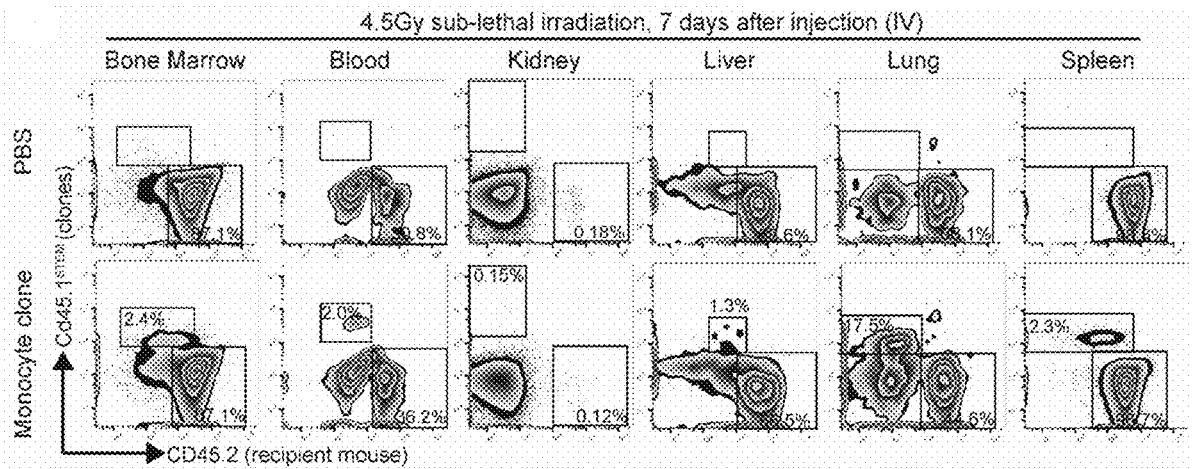
Figure 2A:
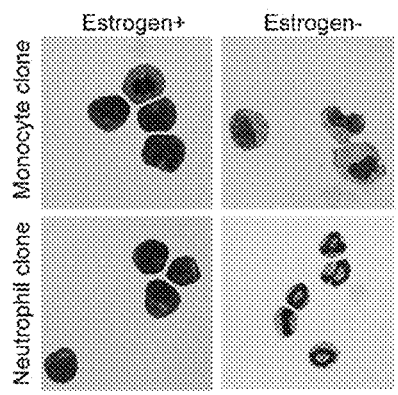
FIGS. 2A-F. Depicts ER-Hoxb8 clones used to study monocytic clonal heterogeneity, related to FIGS. 1A-I. (A) Wright-Giemsa staining of ER-Hoxb8 clones. (B) FACS plots showing Ly6C and Ly6G levels of ER-Hoxb8 clones. (C) Bar graphs showing cell population, related to FIG. 1C. (D) Wright-Giemsa staining of sorted Cd45.1 STEM ER-Hoxb8 clones after the clones emigrate and reside in tissues after injection into the bloodstream. (E) Representative FACS plots showing donor ER-Hoxb8 clones and recipient Cd45.2 mice cells after injection of ER-Hoxb8 clones into the bloodstream (n=3 independent experiments, using 3 mice each experiment). (F) Bar graphs showing expression levels of key monocyte and macrophage markers in donor ER-Hoxb8 cells acquiring different tissue-specific profiles (n=3 independent experiments, using 3 mice each experiment).
Figure 2B:
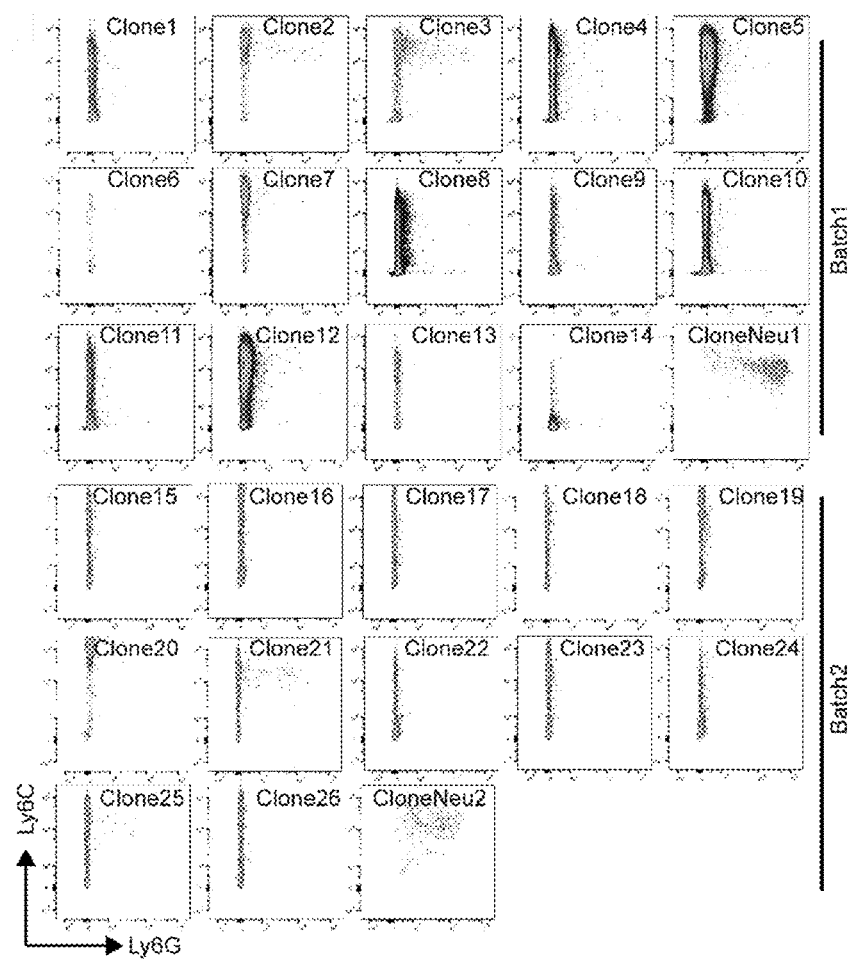
Figure 2C:
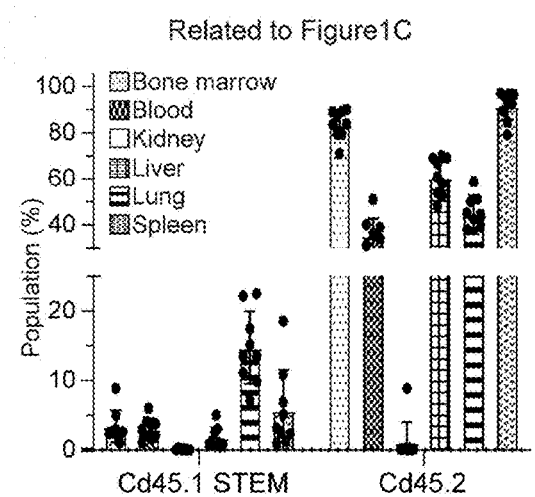
Figure 2D:
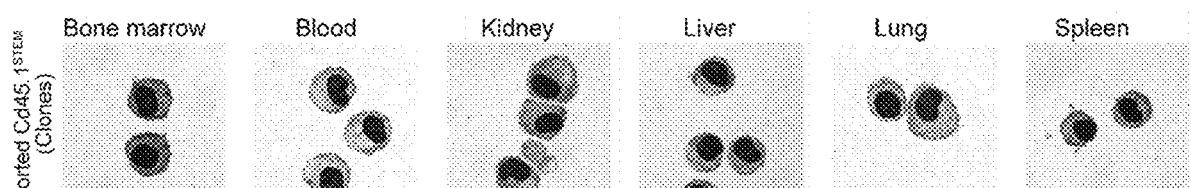
Figure 2E:
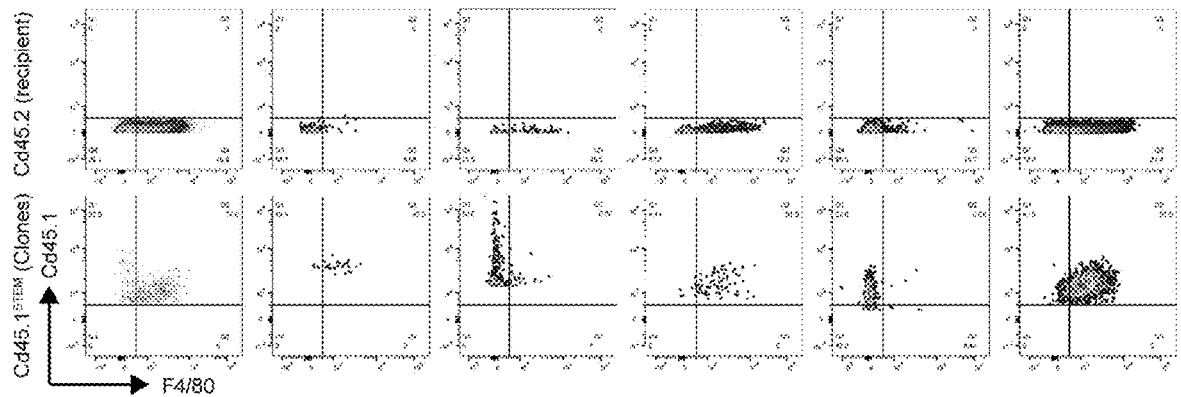
Figure 2F:
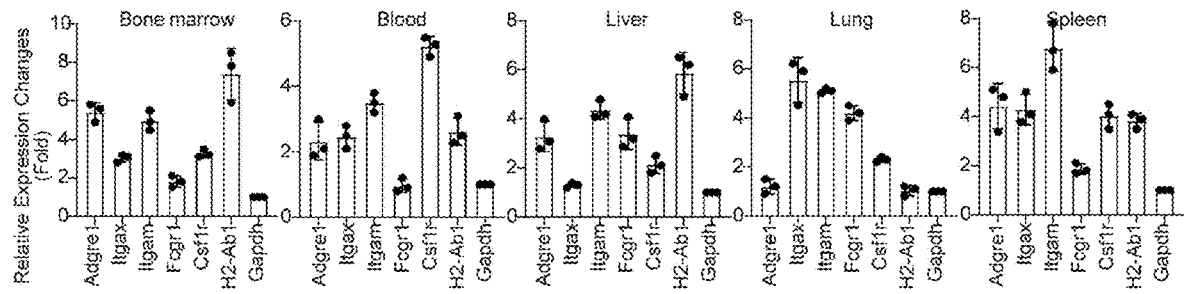

Example 1. Monocytic Cells have GMP Clone-Specific Behaviors that can be Classified into Functional Groups To study the heterogeneity of myeloid progenitors at a clonal level, a system that allows for inducible clonal expansion of primary mouse granulocyte-monocyte progenitors (GMP) capable of differentiating into mature myeloid cells was adapted (Sykes et al., 2016; Wang et al., 2006). Primary murine bone marrow cells transduced with an ER-Hoxb8 fusion construct, and maintained in the presence of an estrogen agonist, self-renew indefinitely as GMPs. These GMPs can be isolated by single cell sorting and propagated as clones in the presence of beta-estradiol (estrogen) (FIG. 1A). Withdrawal of estrogen inactivates the ER-Hoxb8 protein and allows for terminal myeloid differentiation of GMP clones into either monocytes or neutrophils over the course of approximately 5 days, confirmed by their cell surface markers (Cd11b, Lytic, and Ly6G) and morphology (FIGS. 1B and 2A-2B). Undifferentiated GMP clones derived from $Cd45.1^{STEM}$ donor mice were infused into sub-lethally irradiated Cd45.2 recipients and confirmed their ability to undergo in vivo differentiation ($F4/80^{Hi}$) in a variety of tissues after 7 days (FIGS. 1C and 2C-2E). In addition, these injected $Cd45.1^{STEM}$ donor cells were sorted from different tissues followed by performing RT-qPCR to examine if the cells acquired tissue-specific profiles. The donor cells indeed expressed different tissue-specific profiles (Adgre1, Itgax, Itgam, Fcgr1, Csf1r, H2-Ab1) implying that the monocytic clones respond specifically to the tissue environment (FIG. 2F). These data indicate that undifferentiated GMP clones expanded in vitro can differentiate into monocytes both in vitro and in vivo.

Figure 1D:
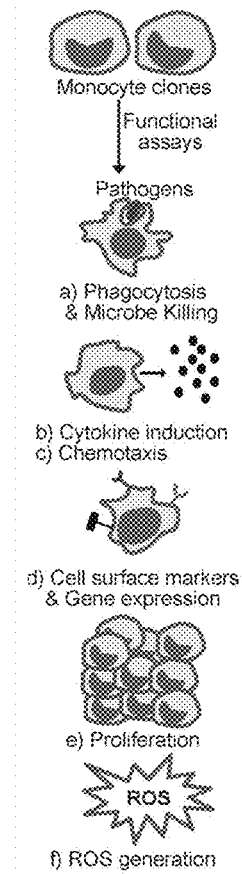

The functional features of cells derived from clonal progenitors were assessed using multiple in vitro assays (FIG. 1D). Monocytes derived from 25 individual GMP clones that yielded only monocytes were first assessed for phagocytosis as measured by intracellular fluorescence of engulfed fluorescently labeled bacteria. This was assessed at baseline and following lipopolysaccharide (LPS) activation. Bactericidal activity was evaluated using bacterial colony forming unit (bCFU) assays. Killing of both gram-negative *Escherichia coli* and gram-positive *Staphylococcus aureus* bacteria was assayed. Intriguingly, there was clone specific capacity for each of the functions and it was regardless of LPS treatment (phagocytosis in FIGS. 3A-3D; bactericidal activity in FIGS. 3E-3F) (Drevets et al., 2015). Clones also varied in their abilities to perform chemotaxis in vitro, a prerequisite for functional blood monocytes to travel from blood into tissues where they transform into macrophages (FIG. 3G). Finally, monocyte production of reactive oxygen species and secretion of TNF-alpha and IL-6 after LPS stimulation were also tested and found to also be clone specific (FIGS. 3H-3J).

Figure 1E:
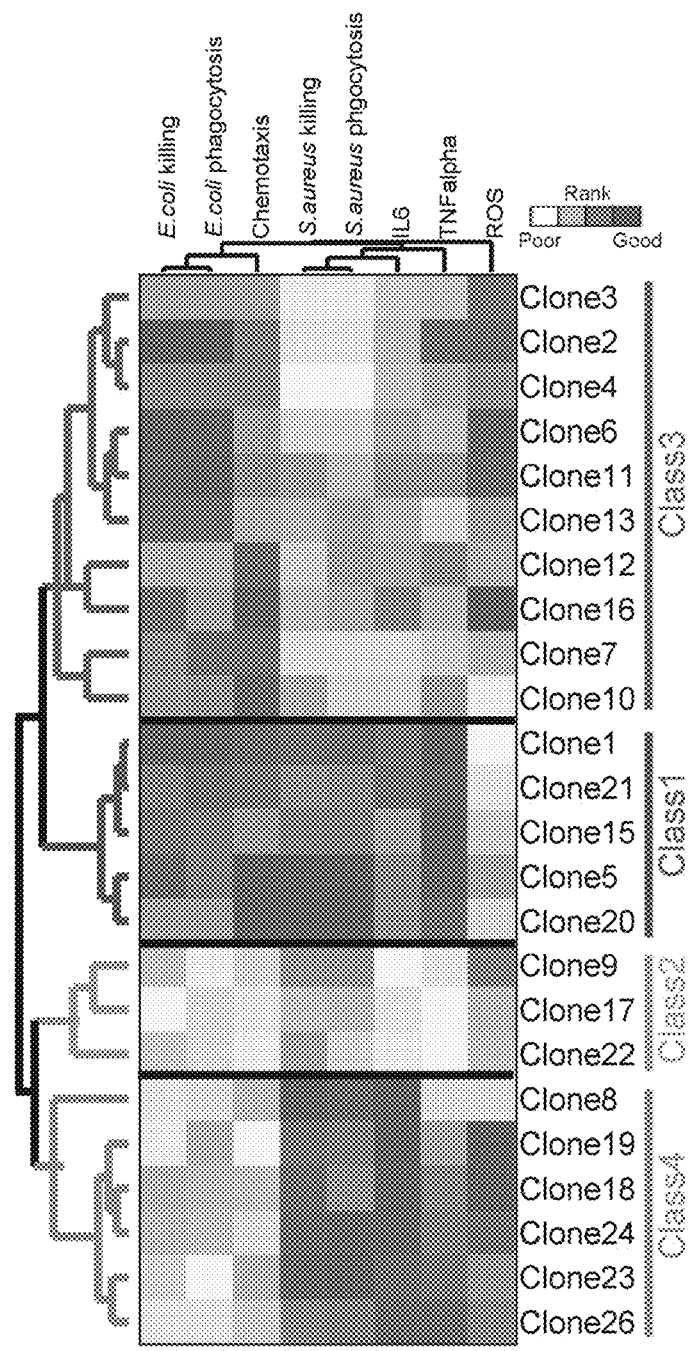
Figure 1F:
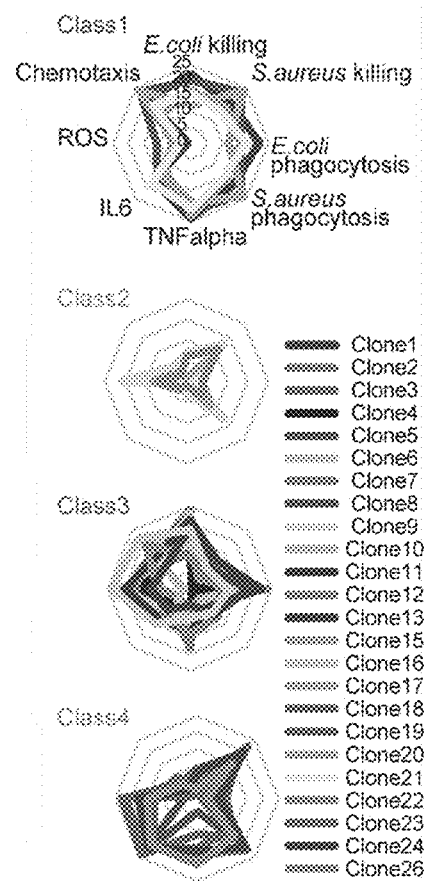
Figure 1G:
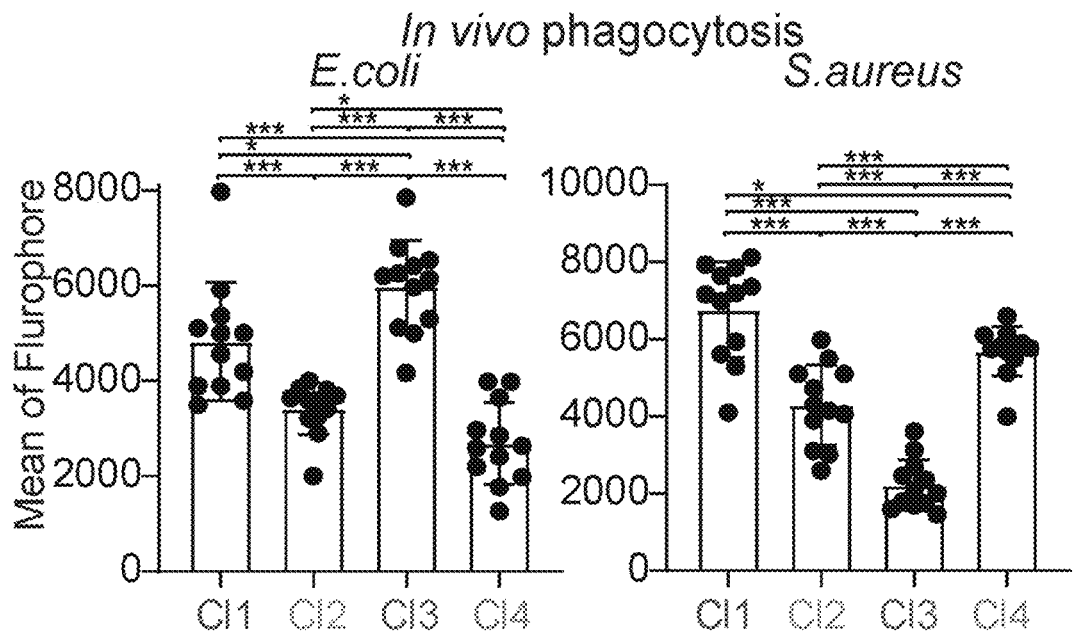
Figure 1H:
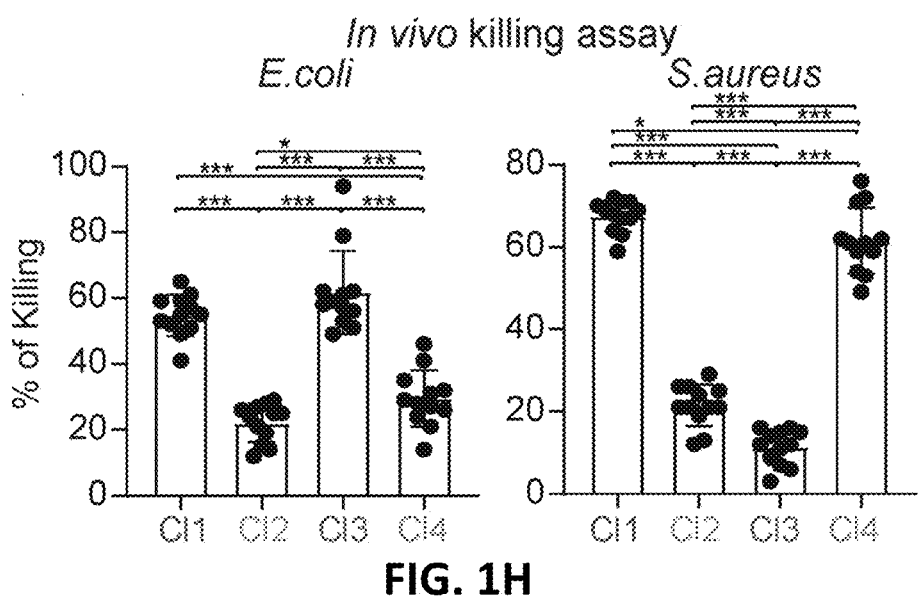
Figure 1I:
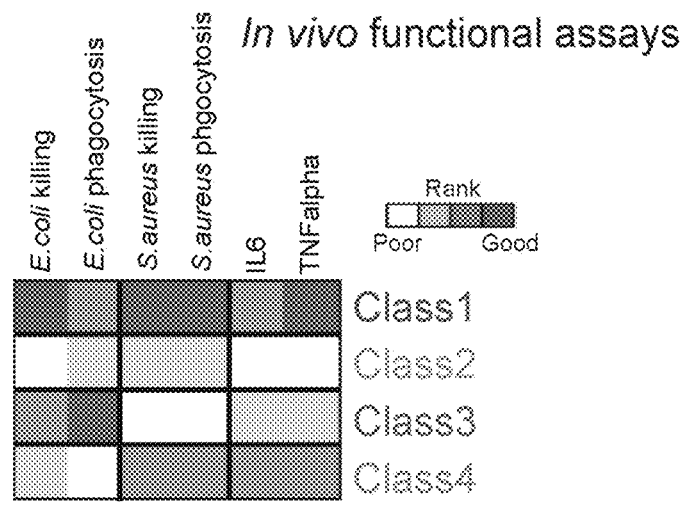
Figure 3K:
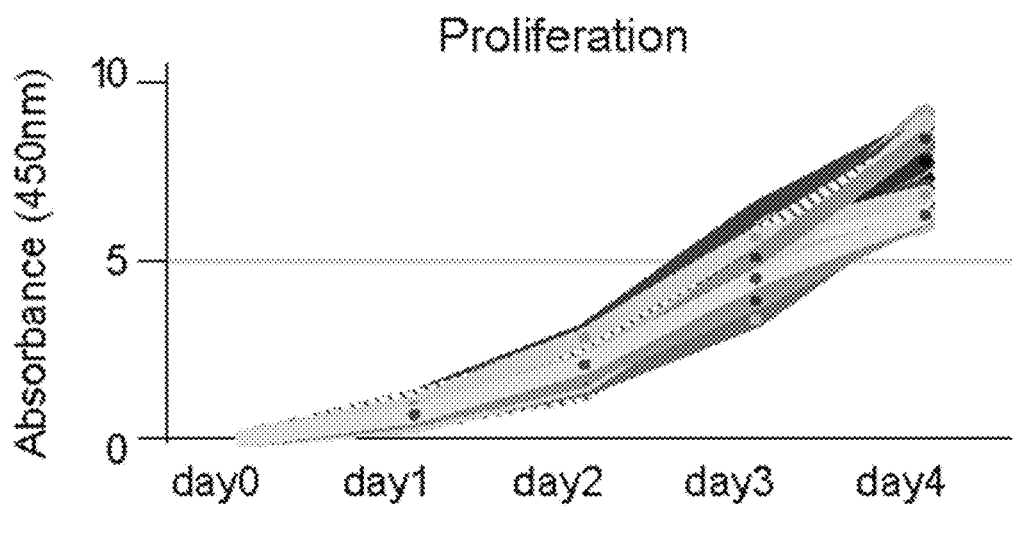
FIGS. 3A-N. Depicts monocytic cells classified into functional groups, related to FIG. 1. (A-D) Bar graphs comparing phagocytosis of E. coli and S. aureus, respectively, by each subclass of ER-Hoxb8 monocytes in vitro. (n=4 independent experiments using 26 clones, in triplicate technical replicates, 1 monocytic clone was removed for presentation due to inconsistency of data). (E,F) Bar graphs comparing the capacity of each subclass of ER-Hoxb8 monocytic clones to kill live E. coli and S. aureus in vitro, respectively (n=6 independent experiments, in triplicate technical replicates). (G) Bar graphs comparing chemotaxis of ER-Hoxb8 clones (n=3 independent experiments, in triplicate technical replicates). (H) Bar graphs showing relative ROS production of ER-Hoxb8 monocytic clones normalized to GMP clones (n=4 independent experiments, in triplicate technical replicates). (I,J) Bar graphs comparing clonal production of TNFα and IL6, respectively, by ELISA (n=4 independent experiments, in triplicate technical replicates). (K) Line graphs comparing the proliferation of ER-Hoxb8 clones over 4 days (n=3 independent experiments, in quadruplicate technical replicates). (L) Bar graphs showing cell cycles of each functional subclass ER-Hoxb8 clones. (M) Bar graphs comparing intracellular cytokine production of each functional subclass ER-Hoxb8 clones after injection in mice (n=3 independent experiments, using 3 mice each experiment). (N) Radar plot showing the in vivo functional abilities of ER-Hoxb8 clones. * P<0.05,  P<0.01, and * P<0.005.
Figure 3L:
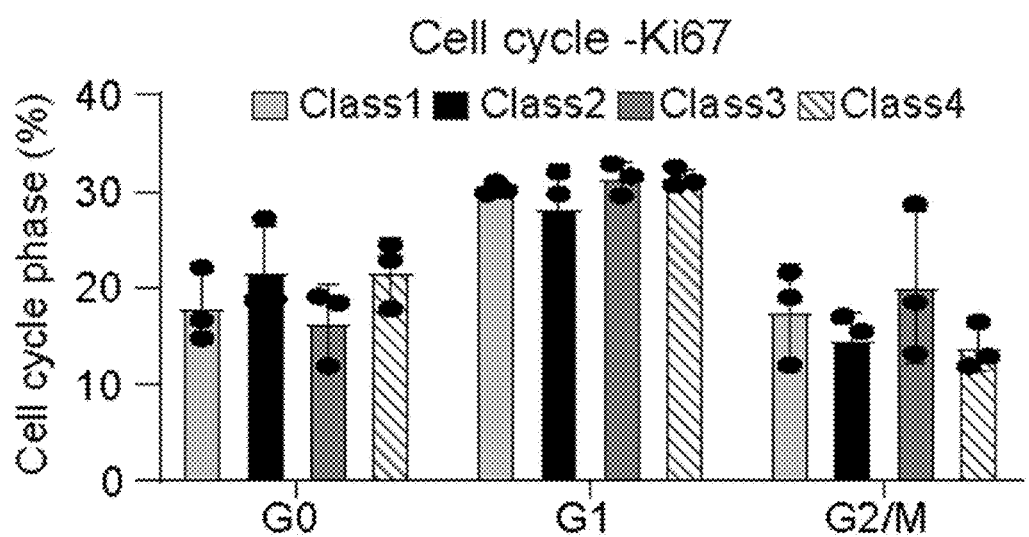
Figure 3M:
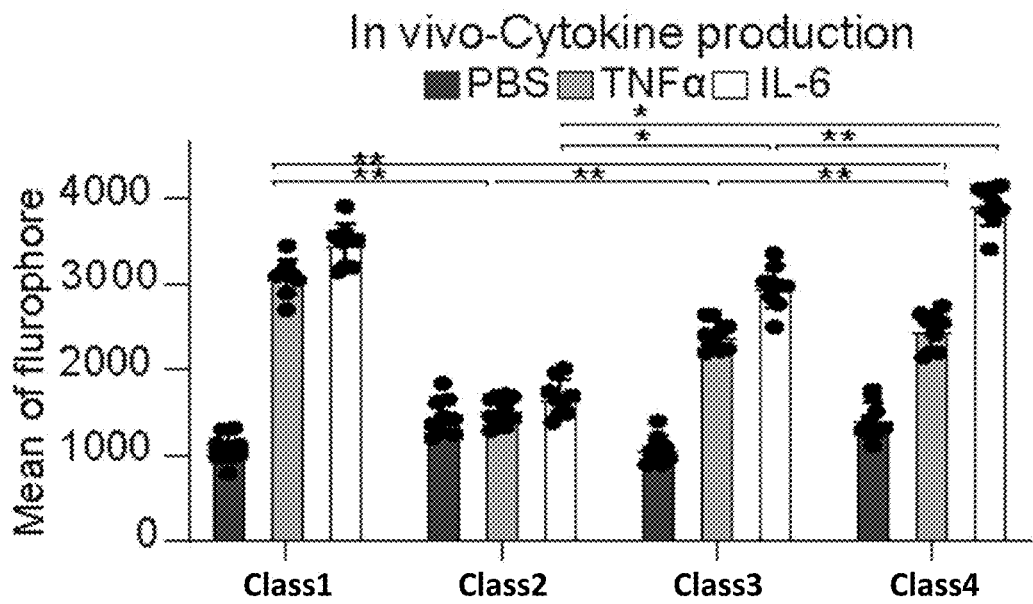
Figure 3N:
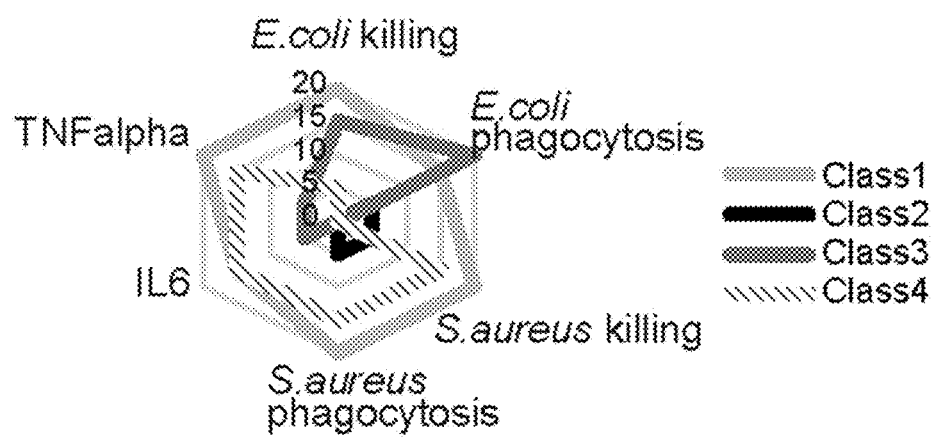

By scoring each of the parameters by ranks between the clones, unsupervised clustering of the aggregated functional data identified four distinct functional groups (FIGS. 1E and 1F). Functional distinctions were not due to differences in differentiation and proliferation rates, which were equivalent between clones (FIG. 3K). In addition, proliferation and cell cycle of ER-Hoxb8 clones were assessed by Ki67 and DAPI staining and no significant differences in cell cycle phase were found in different ER-Hoxb8 monocytic clones (FIG. 3L). These data indicate that GMPs can differentiate into functionally distinctive monocytes. Notably, when separate aliquots of each GMP clone were differentiated, their descendent monocytes performed in a highly similar manner. The biological replicates from different aliquots showed a similar pattern of functional abilities, indicating that the clones differentiated into monocytes that had stereotypic, clone specific behaviors.

This four distinct functional monocyte grouping suggests a subcategorization beyond inflammatory classical and resident non-classical monocytes (Gordon and Taylor, 2005). Importantly, although all clones could perform the functions tested, there were significant differences in how well each class performed. Broadly characterizing each group, Class1 was more adept at both *E. coli* and *S. aureus* bacterial killing, chemotaxis, and cytokine secretion. Class2 did not perform well in most functional assays, but had more ROS production upon LPS stimulation than Class1. Class3 exhibited preferential *E. coli* killing over *S. aureus* and strong ROS production following LPS stimulation. Class4 was more effective at killing *S. aureus* than *E. coli* and vigorously produced cytokines.

To test if these classifications were relevant in vivo, clones from each class of monocyte were intraperitoneally or intravenously injected into lethally irradiated mice with live bacteria or labeled heat-killed bacteria followed by assessing their capacity to clear the infection and produce cytokines. Consistent with our in vitro findings, Class1 phagocytosed and cleared the bacteria most efficiently with the highest secretion of the cytokines IL6 and TNFalpha. Class3 and Class4 were efficient in killing *E. coli* and *S. aureus* respectively in vivo, whereas Class2 was inefficient in the monocyte functions tested (FIGS. 1G-1I and 3M-3N). Collectively, monocytes from the ER-Hoxb8 system can be functionally distinguished into four classes with distinctive and defined functional behaviors in vitro and in vivo.

Example 2. Subgroups of Monocytes Exhibit Distinct Gene Expression Signatures

Figure 4A:
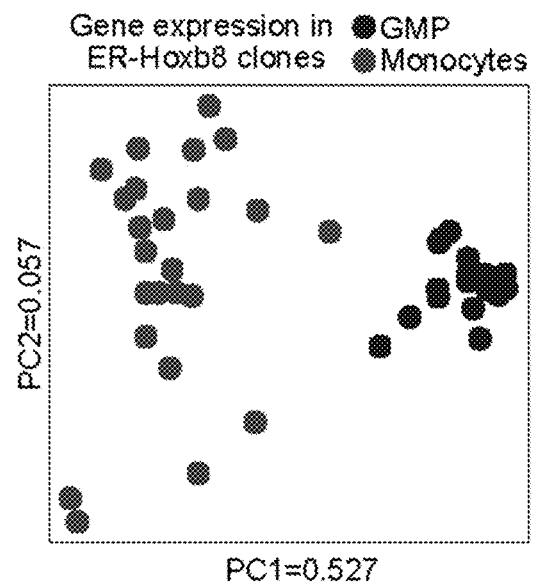
FIGS. 4A-I. Depicts monocyte subsets having distinct gene expression signatures. (A) PCA plot of gene expression patterns in ER-Hoxb8 progenitors and monocytes. (B,C) UMAP plot of GMP and monocytes clones with expression of known monocytic markers. (D) Correlation heatmap of gene expression patterns in both GMP and monocytic clones. Functional classes are highlighted by boxes. (E) PCA of global gene expression patterns reveals distinct subgroups of monocytic clones. Points are grouped by functional class. (F) Heatmap of class-specific gene expression levels in monocytic clones. (G) Combined PCA of expression patterns in ER-Hoxb8 monocytes and primary mouse monocytes with previously defined classification. Points are grouped by monocyte classification. (H) Heatmap of gene expression levels in ER-Hoxb8 monocytes together with previously published primary mouse blood monocytes, for the genes differentially expressed between any two classes in ER-Hoxb8 monocytic clones. The levels are shown as Z-scores based on the expression of a given gene across all samples. (I) Gene enrichment analysis of class-specific differentiation signatures between a GMP clone and the corresponding monocyte clone. See FIGS. 5A-F.
Figure 4B:
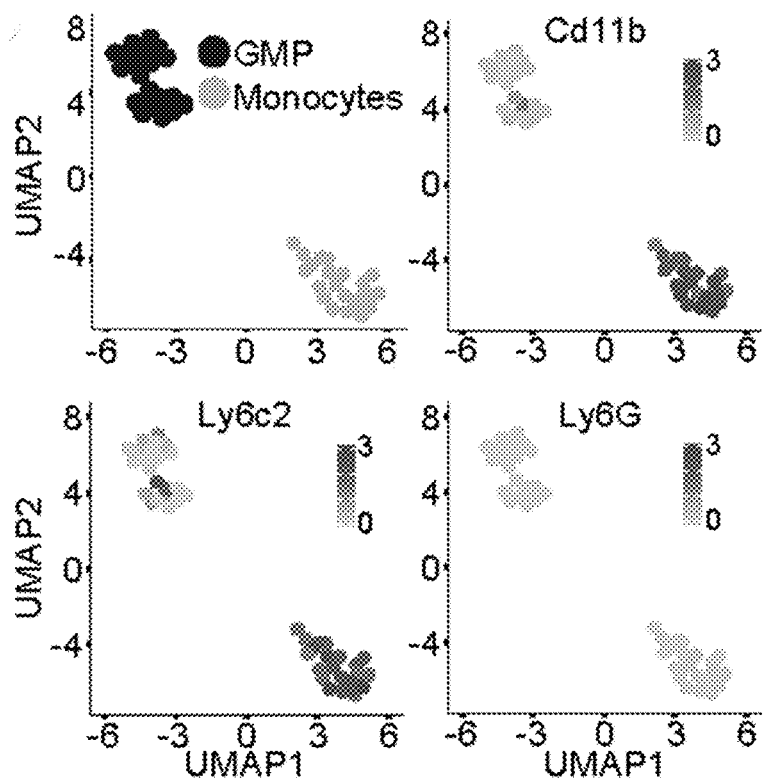
Figure 4C:
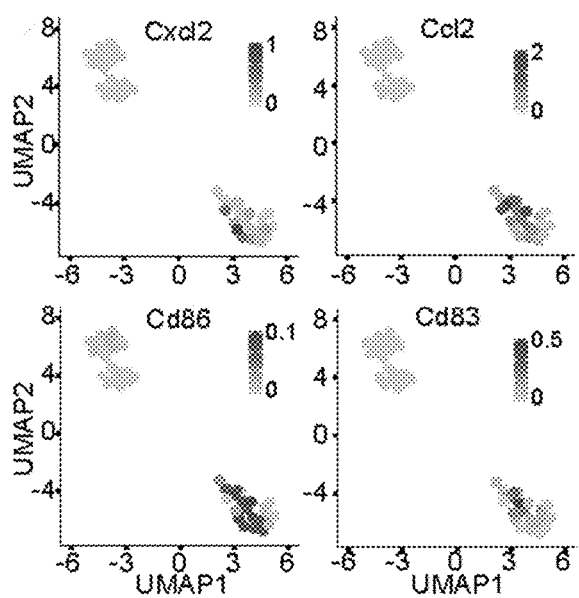
Figure 4D:
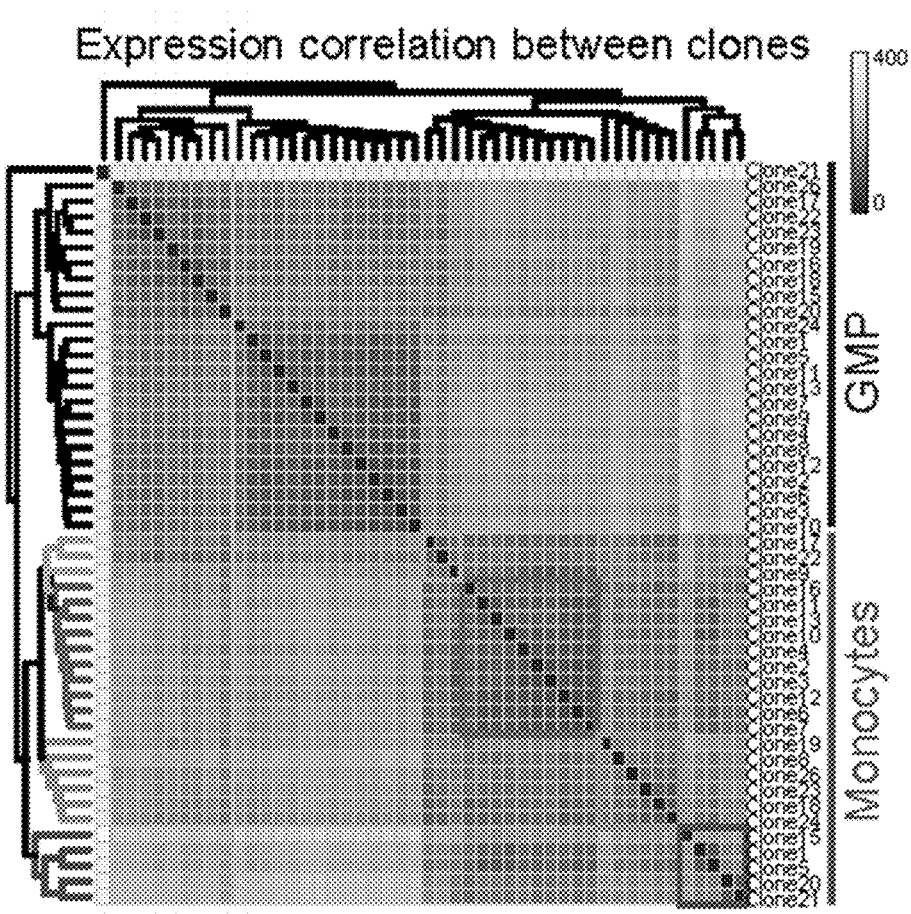
Figure 4E:
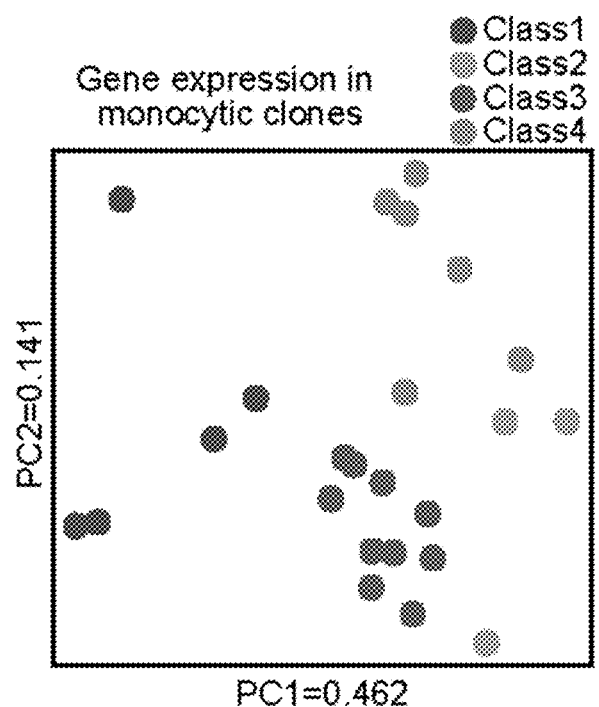
Figure 5A:
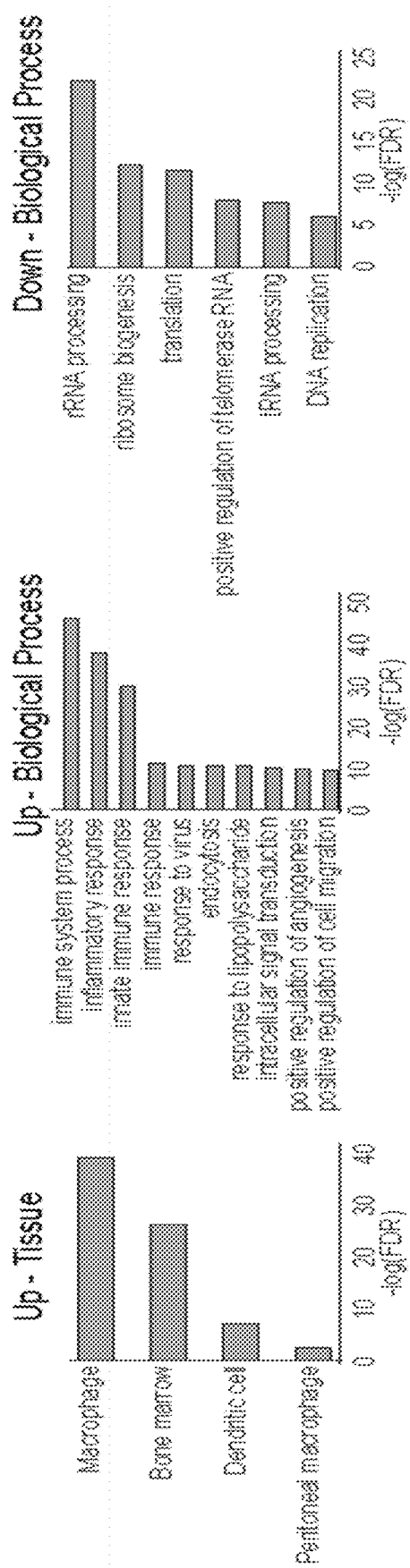
FIGS. 5A-F. Depicts subgroups of monocytes exhibiting distinct gene expression signatures, related to FIGS. 4 and 6. (A) Bar graphs showing enriched GO terms of differentially expressed genes in ER-Hoxb8 monocyte clones. (B) Bar graphs showing enriched GO terms of monocyte class-specific genes. (C) Scatter plot of RNA expression against chromatin accessibility in Clone1 as a representative example. (D) RNA-seq of ER-Hoxb8 monocytic clones showing Cd49f and Cd54 are differentially expressed in each class. (E,F) Scatter plots of RNA expression differences against chromatin accessibility differences between progenitor classes and monocyte classes, respectively.

To assess if the functional distinctions between monocytes were reflected in their transcriptional signatures, RNA-sequencing on both clonally paired GMP ER-Hoxb8 progenitors and mature monocytes were performed. Expression profiles of GMP and monocytes clustered distinctly from each other as expected (FIGS. 4A-D). Monocytes derived from ER-Hoxb8 clones had innate immune response related genes and macrophage markers up-regulated and rRNA processing and ribosome biogenesis related genes down-regulated compared with GMP (FIG. 5A). They were transcriptionally similar to murine naïve primary monocytes, including the expression of key monocytic genes such as Ly6c2 and Cd11b, but not in the key neutrophil gene Ly6G (FIG. 4B). Notably, whereas all GMP clones had similar transcriptomes (FIG. 4A), unsupervised correlation analyses and PCA revealed four distinct monocyte classes that corresponded with their functional classifications (FIGS. 4D and 4E). Clustering was not biased or trained by known monocyte markers.

Figure 4F:
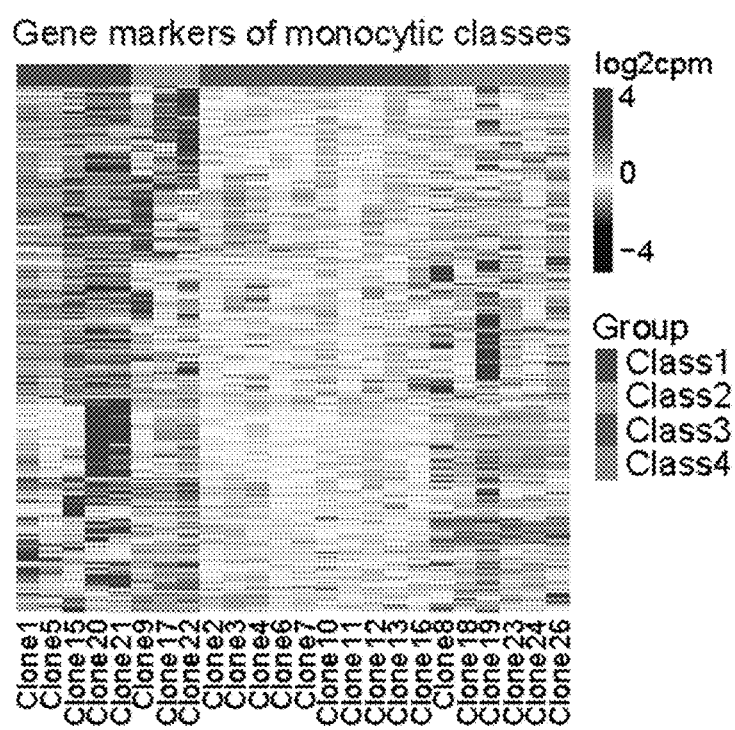
Figure 5B:
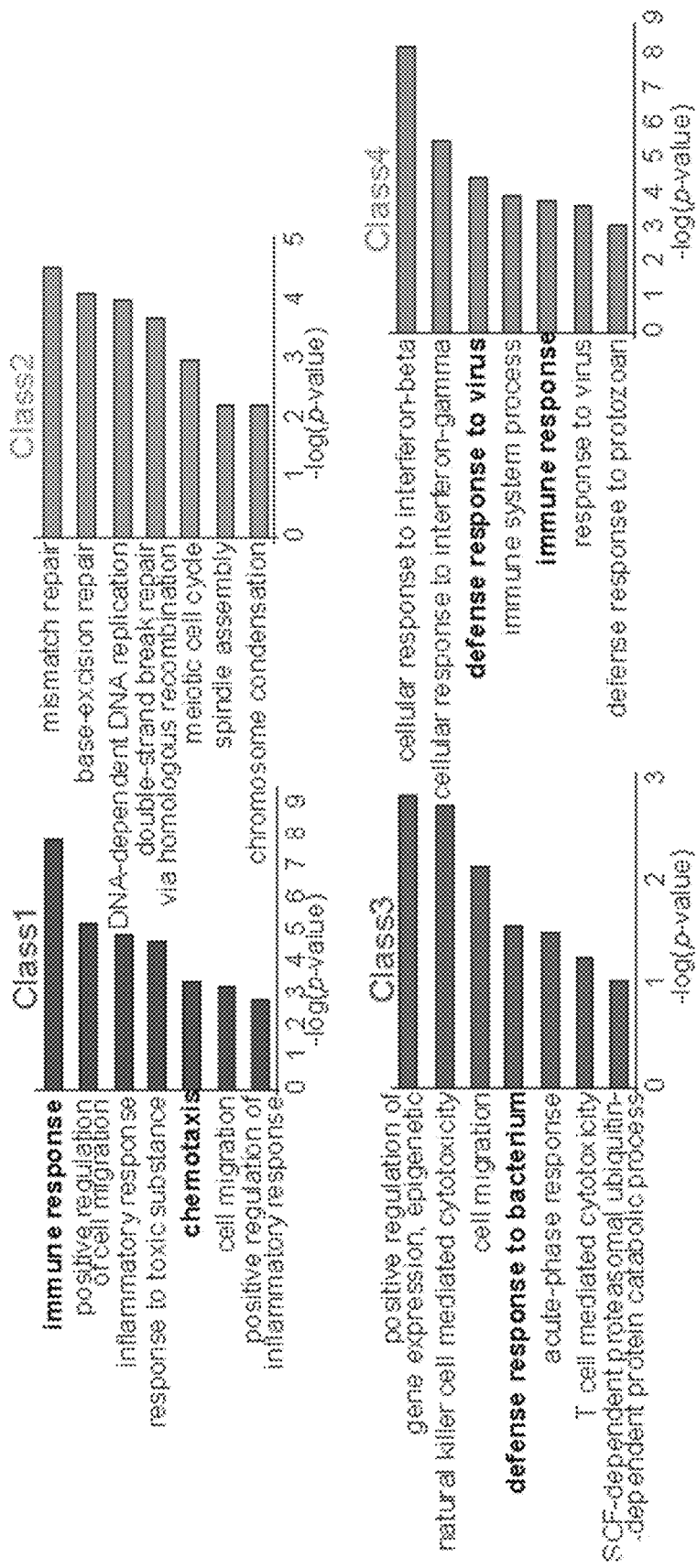

Differential expression gene (DEG) analyses of each class of clones against all other clones were used to define gene markers of each class, shown in the expression heatmap along with the class-specific enrichment of functional gene sets (FIGS. 4F and 5B). Class1 monocytes were enriched in general immune response genes including inflammatory response and response to toxic substances, whereas Class3 monocytes were enriched in defense response to bacteria and acute-phase response genes. Class4 monocytes were specifically enriched in genes for immune response and viral defense. Interestingly, genes that were highly expressed in Class2 were not enriched in monocyte-associated functional terms, but rather associated with terms such as DNA repair.

Figure 4G:
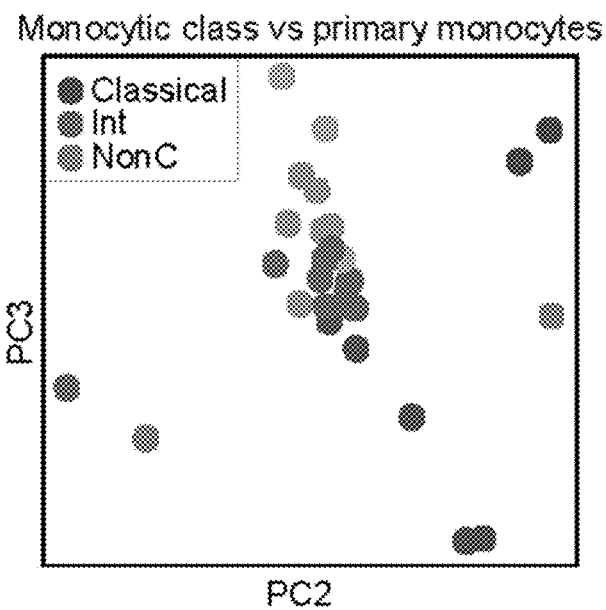
Figure 4H:
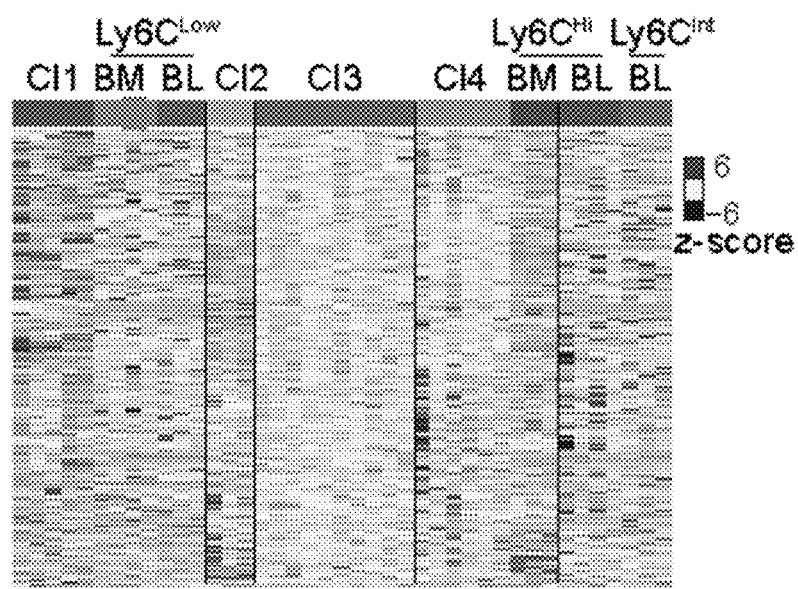
Figure 4I:
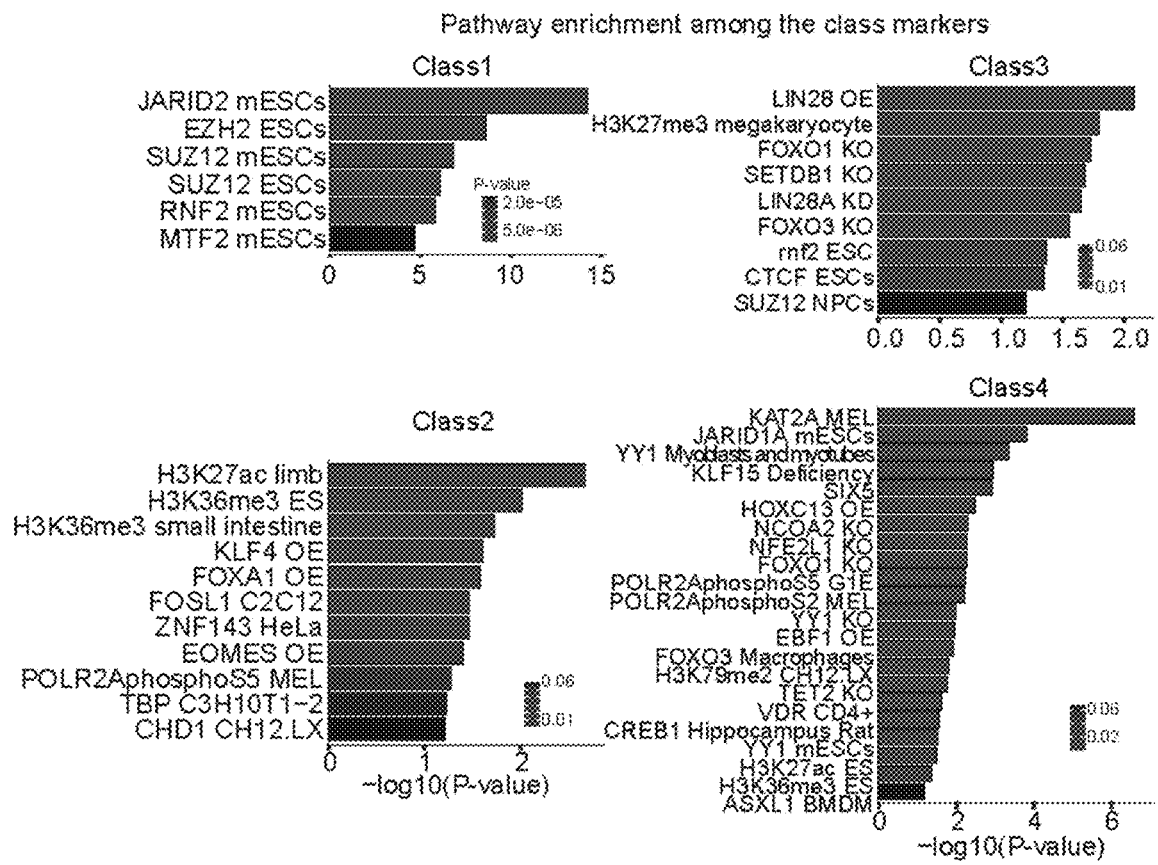

Next, the transcriptomic relationship of functionally defined monocyte groups was assessed in comparison to previously described classes of murine primary monocytes (classical, intermediate, and non-classical). Clear global transcriptomic correlations between previously described monocytic classes and these defined classes were not observed (FIG. 4G). However, when using DEG only, Class1 and Class4 transcriptionally resemble non-classical and classical monocytes, respectively (FIG. 4H). These data suggest that our functionally defined monocyte classes further recapitulate the heterogeneity of primary monocytes at the transcriptomic-level.

Gene expression signatures of clones differentiated from GMP to monocytes was analyzed using DEG between the monocyte and GMP stage for clones within each class and assessing functional enrichment among these genes by EnrichR (Chen et al., 2013; Xie et al., 2021). Interestingly, differentiation signatures for each class were enriched in distinct gene sets associated with key chromatin regulators and transcription factors (FIG. 2I). For example, whereas DEG of Class1 were strongly enriched in the binding targets of Polycomb complexes PRC1 and 2, DEG of Class3 were enriched in the targets of Polycomb and the related H3K27me3 histone mark, but also in the targets of H3K9 methyltransferase SETDB1, transcription factors LIN28, FOXO1 and 3, and a key regulator of chromatin interactions CTCF. Differentiation in Class2 was associated with PolII, TBP, transcription-related chromatin factor CHD1 and histone marks H3K36me3 and H3K27ac, as well as stem cell differentiation factors, whereas Class4 was associated with similar transcriptional machinery but a different group of chromatin regulators and differentiation factors (for example, KAT2A, Tet2, Yy1, Jarid1A, Ebf1, Hoxc13, Asx11). Taken together, these signatures suggest that monocyte classes may have distinct differentiation mechanisms and trajectories.

Example 3. Epigenetic Patterns Pre-Exist in GMP Presaging Monocyte Subgroups

Figure 5C:
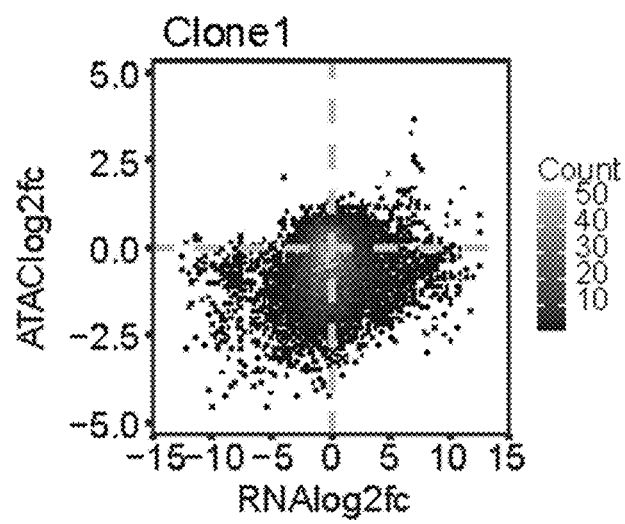
Figure 5D:
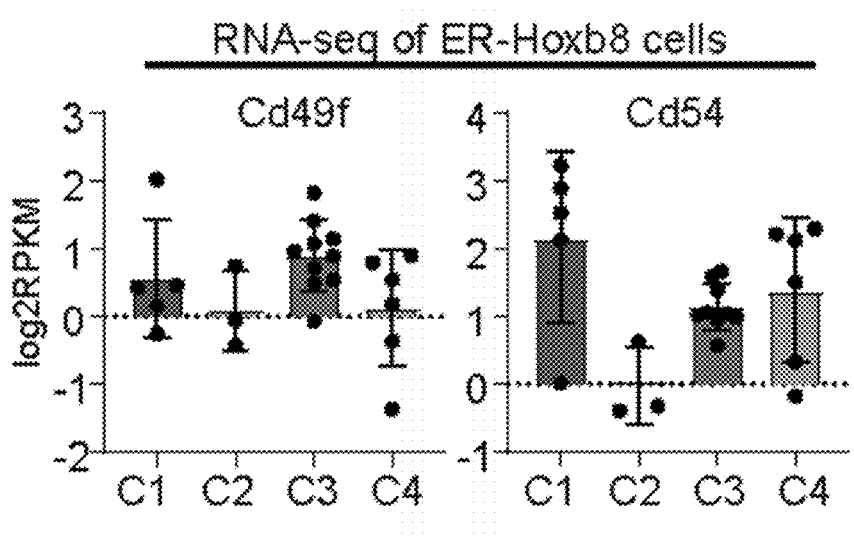
Figure 6A:
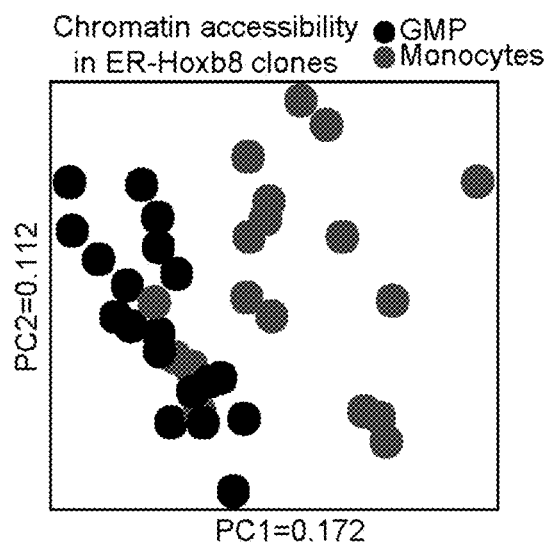
Figure 6B:
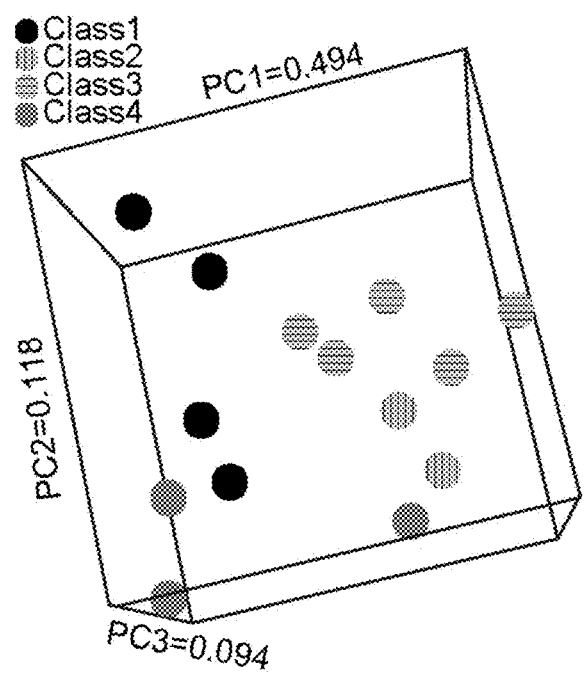
Figure 6C:
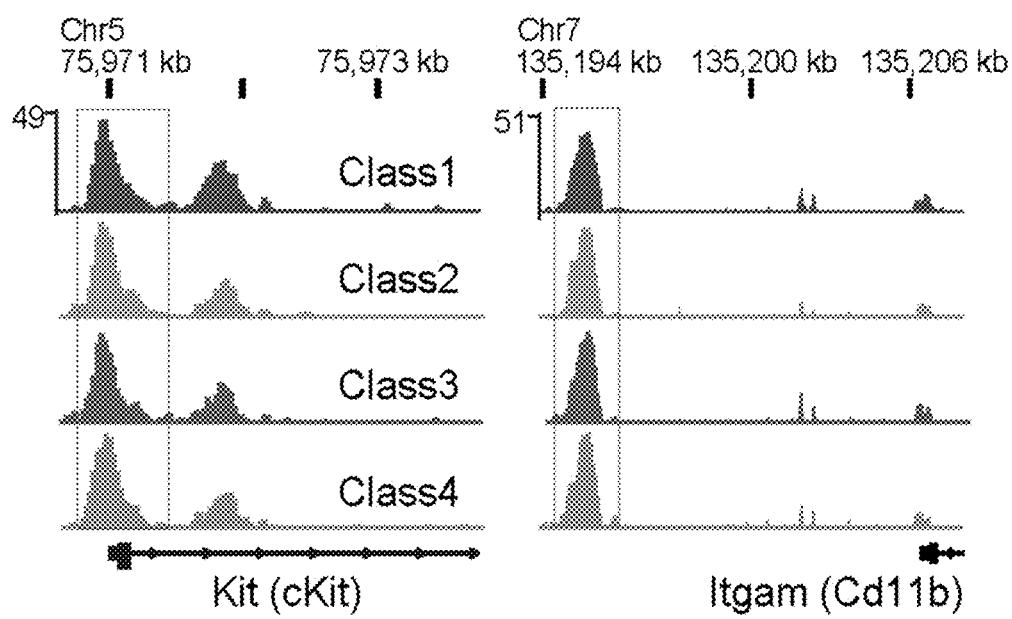
Figure 6D:
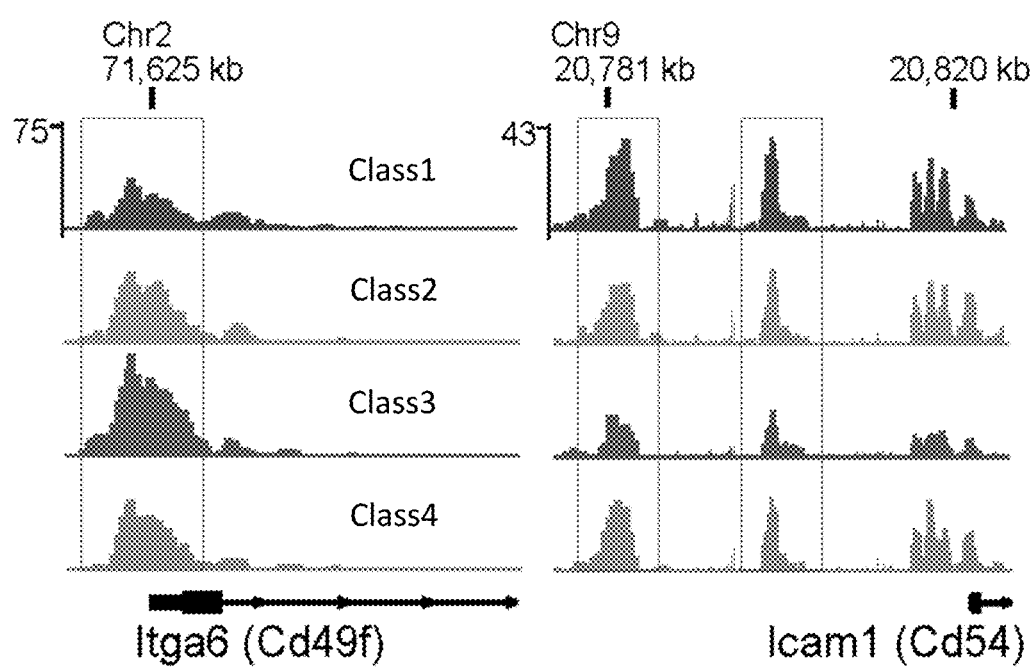

To assess the relationship of transcriptional differences among monocytes with epigenetic signatures of their progenitors, ATAC-seq was performed on both GMP clones and their differentiated monocytic progeny (FIG. 5C). Surprisingly, GMPs had heterogeneous patterns of chromatin accessibility largely different from monocytes (FIG. 6A) and the four clone groups of GMP had distinct chromatin accessibility corresponding to their functional classification (FIG. 6B). For example, the regulatory regions of the key marker genes such as cKit and Cd11b had a similar chromatin openness between GMP subsets (FIG. 6C). In contrast, cell surface markers such as Cd49f and Cd54 that were differentially expressed in monocytes (FIG. 5D), had differential chromatin openness between the subsets (FIG. 6D). The chromatin configuration in the GMP was reflected in the gene expression in the descendant monocytic subsets.

Figure 5E:
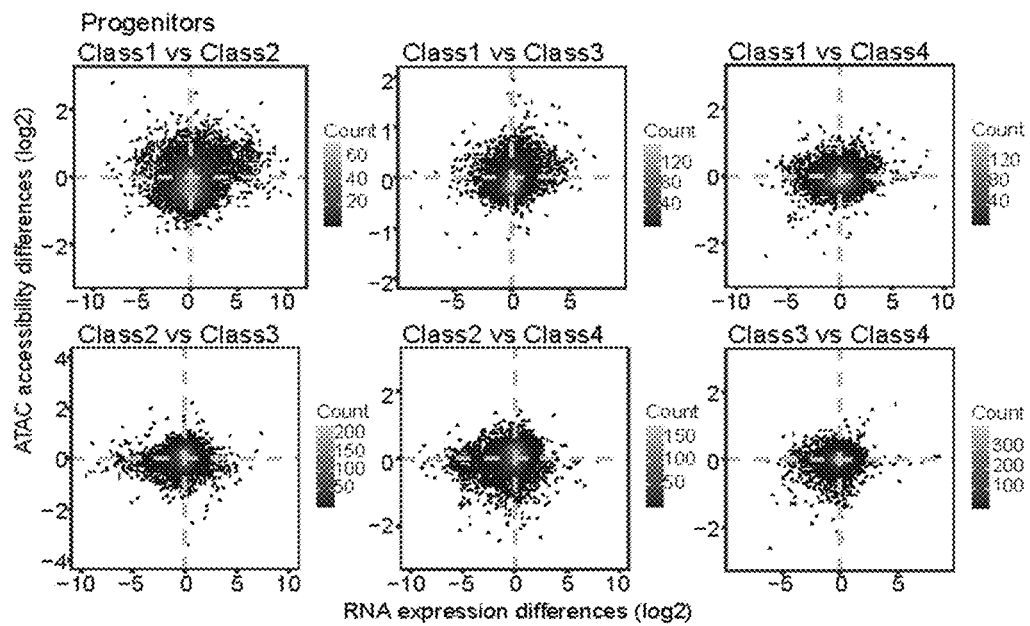
Figure 5F:
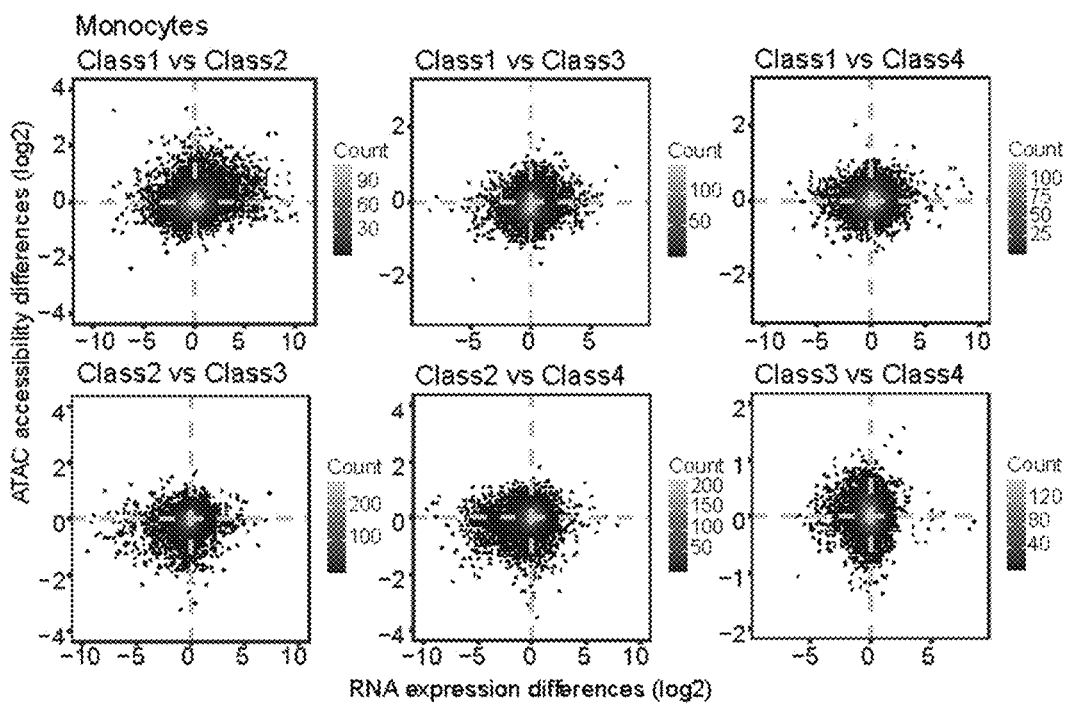
Figure 6E:
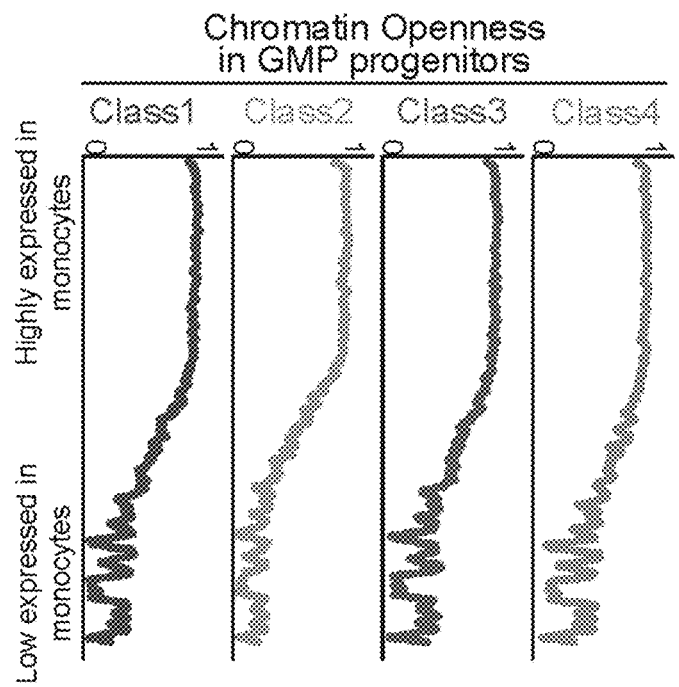
Figure 6F:
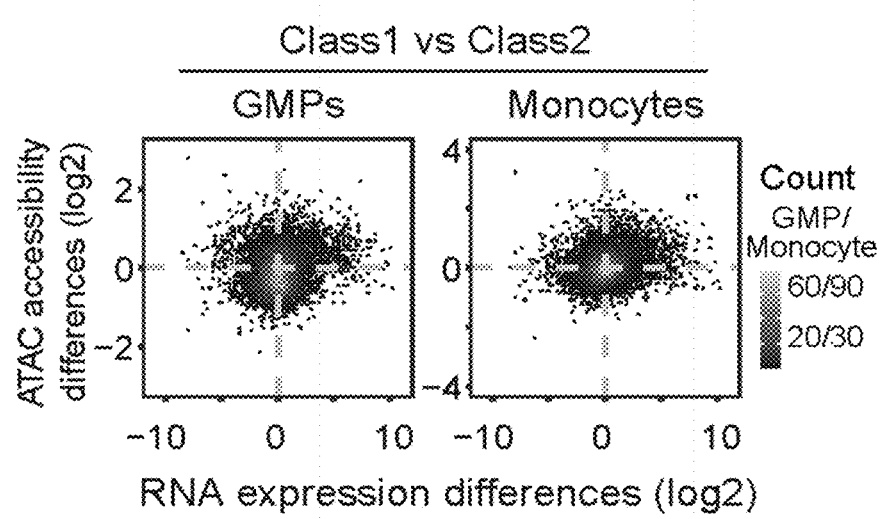
Figure 6G:
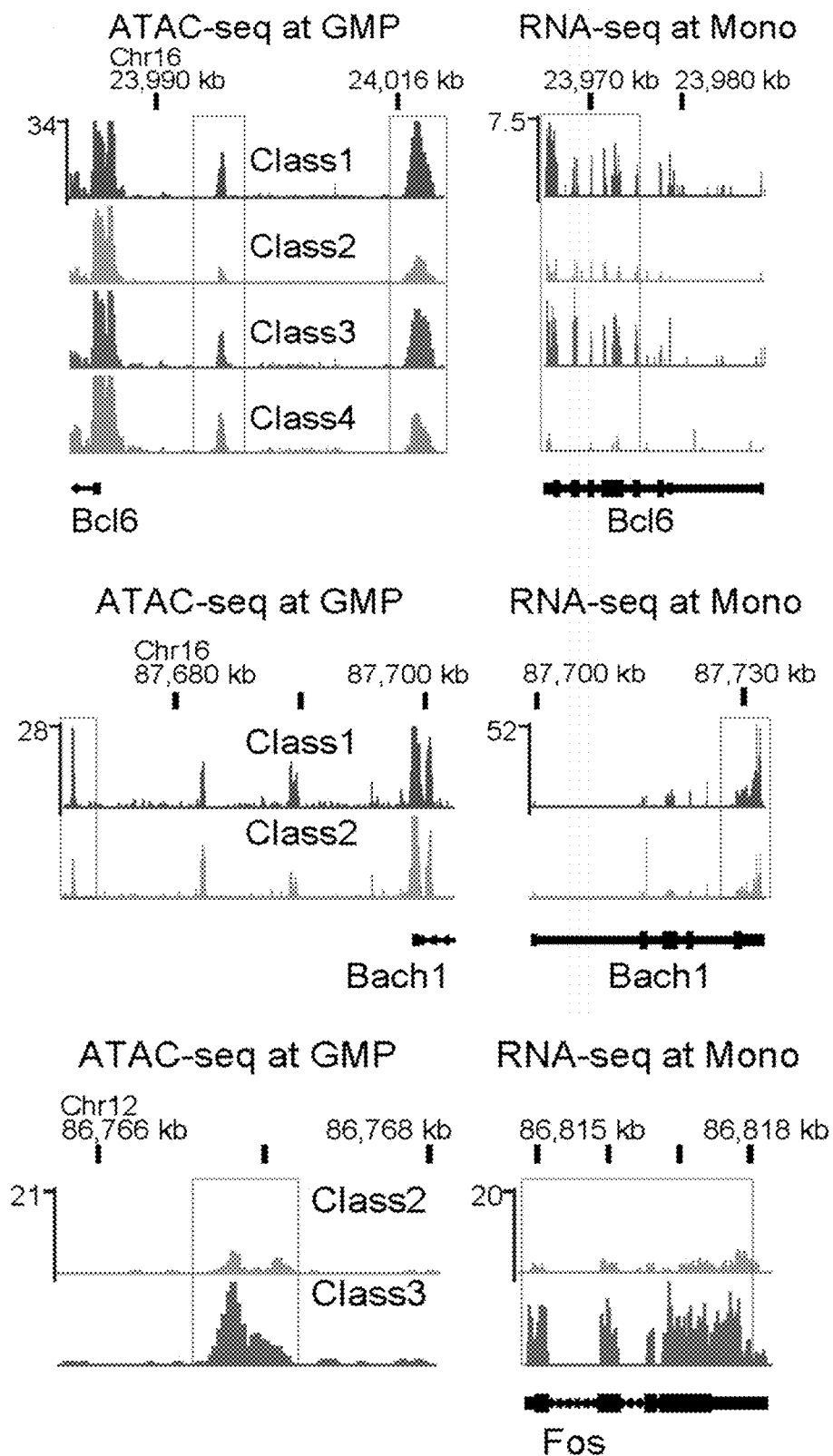
Figure 6H:
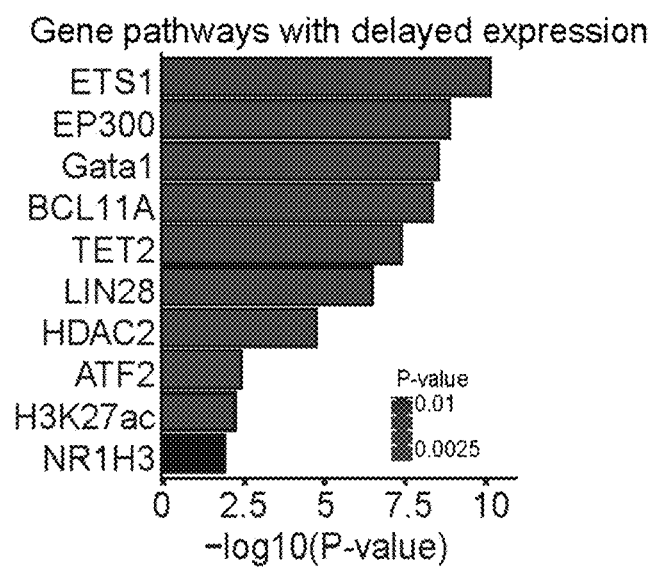

Furthermore, global analysis of genes highly expressed in the monocyte classes had evidence of chromatin openness in the respective GMP clone (FIG. 6E). This implies that monocytic subsets might be primed epigenetically at the level of progenitor cells. Genome-wide, quantitative differences of promoter chromatin accessibility between GMP classes had a modest correlation with quantitative transcriptional differences between monocyte classes (FIGS. 6F and 5E-5F). However, a considerable group of genes in GMPs showed class-specific differences of enhancer chromatin accessibility that preceded corresponding differences of gene expression in monocytes, but were not transcriptionally manifested in GMPs themselves. For instance, genes that are important in myeloid lineages such as Bcl6, Bach1, and Fos, had differential chromatin accessibility at nearby ATAC-seq peaks in the progenitors, but their expression levels were affected only in the descendent monocytes (FIG. 6G). As a whole, this group of genes was enriched in the targets of key differentiation-related transcription factors and chromatin modifiers, including P300 and associated histone mark H3K27ac, Gata1, Bcl11a, Tet2, Lin28, and HDAC2 (FIG. 6H). Furthermore, sequence motif analysis of the corresponding enhancer ATAC-seq peaks revealed binding motifs of key myeloid lineage markers (FIG. 6I). Altogether, these data suggest that the class-specific epigenetic signatures in the vicinity of key differentiation genes in GMPs may serve as a blueprint of class-specific gene expression in the descendent mature cells.

Figure 7A:
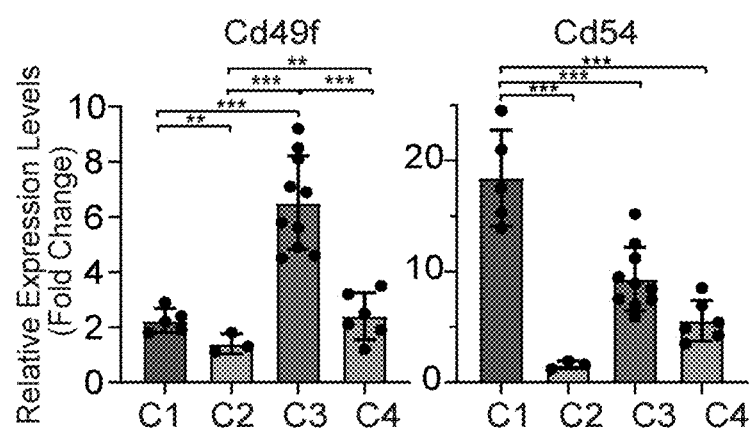
FIGS. 7A-I. Depicts Cd49f and Cd54 as class-specific markers of monocytic cells in mouse and human blood. (A) RT-qPCR of ER-Hoxb8 monocytic clones showing Cd49f and Cd54 are differentially expressed in each class. (B) Representative FACS plots showing Cd49f and Cd54 reveal distinct subgroups of murine primary bone marrow monocytes (n>10 independent experiments). (C) Histograms showing Cd49f and Cd54 expression in ER-Hoxb8 monocytic clones, during steady conditions (n=3 independent experiments, in triplicate technical replicates). (D) Representative FACS plots showing Ly6C levels in each class of primary mouse monocytes (n>10 independent experiments). (E) Representative FACS plots showing Cd49f and Cd54 can distinguish subgroups of monocytes in multiple murine tissues (n=3 independent experiments, using 3 mice each experiment). (F) Wright-Giemsa staining of sorted murine cells confirming monocytic morphologies of sorted monocytes. (G) Bar graphs showing sorted Class1-4 primary monocytes cultured in M-CSF, GM-CSF, and IL-3. (H) Representative FACS plots showing CD49F and CD54 can distinguish subgroups of human primary monocytes from peripheral blood (n=2 independent experiments, using 2-3 donors each experiment). (I) Wright-Giemsa staining of sorted human monocytic cells. *P<0.05, P<0.01, and *P<0.005. See FIGS. 8A-H and 9A-F.
Figure 7B:
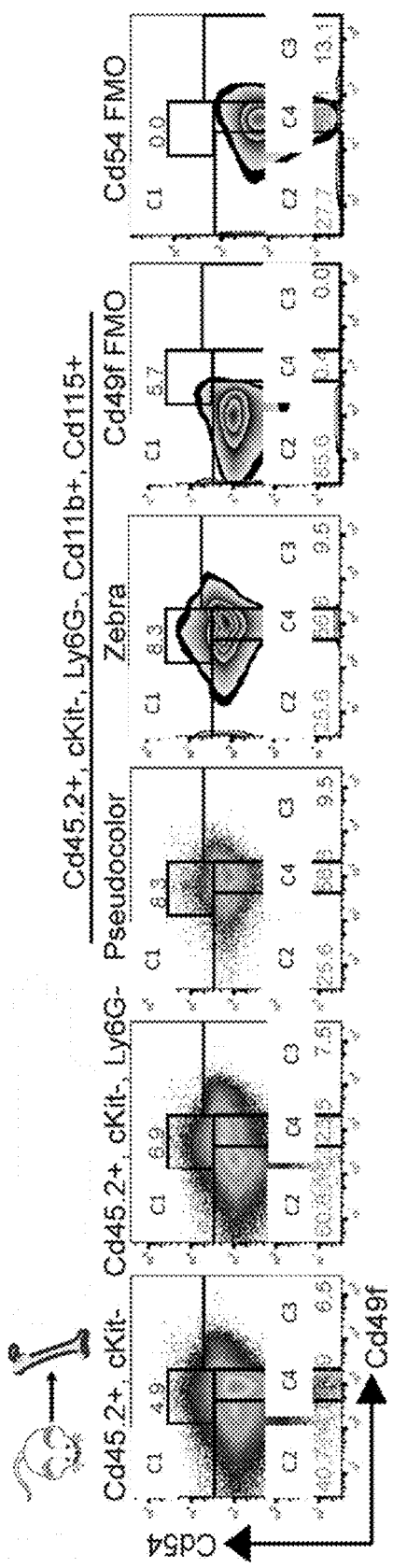
Figure 7C:
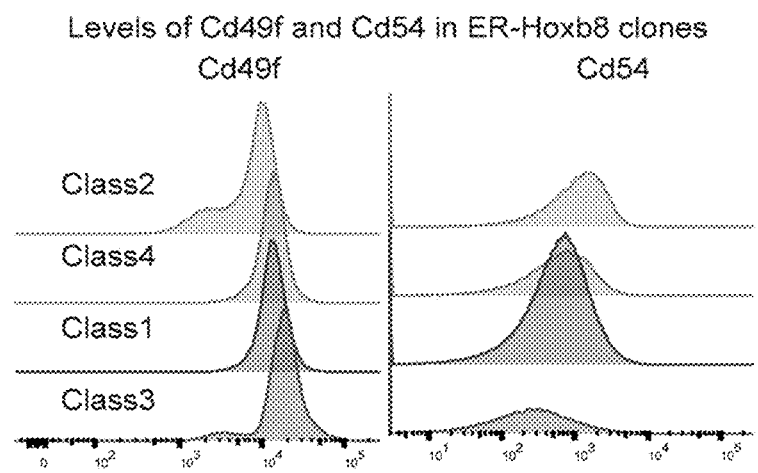
Figure 7D:
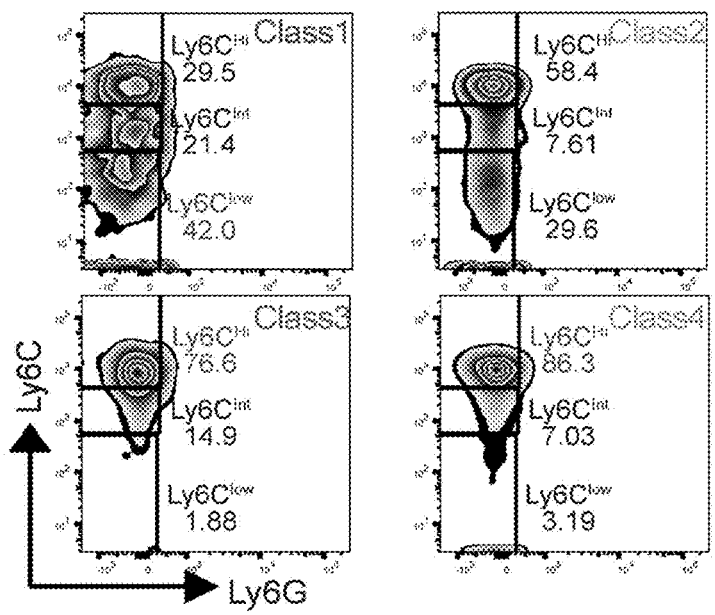
Figure 8A:
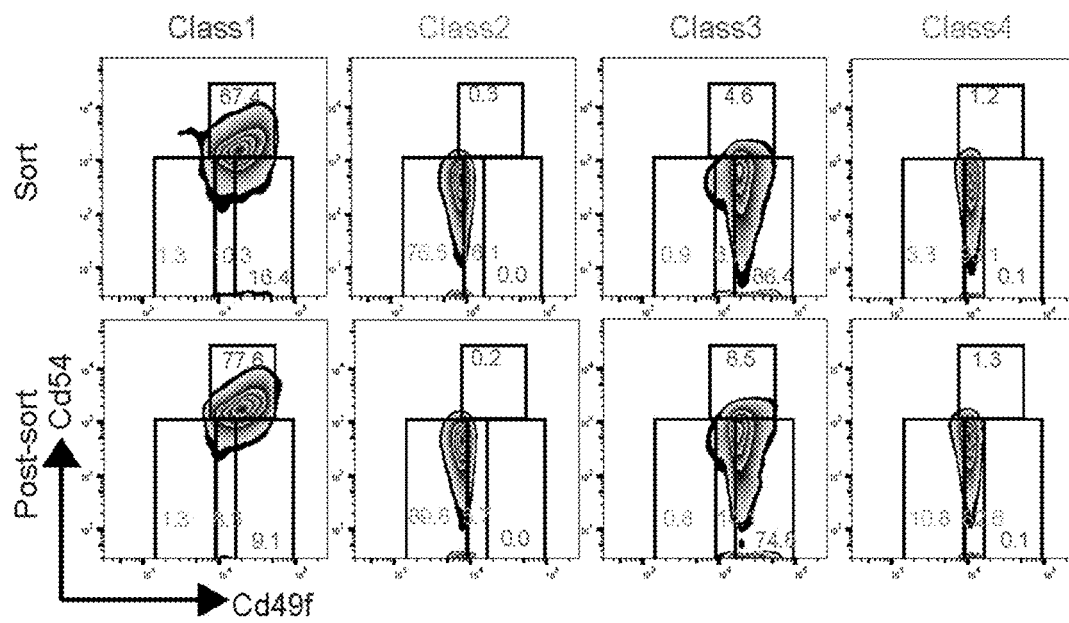
FIGS. 8A-H. Depicts Cd49f and Cd54 as class-specific markers of monocytic cells, related to FIGS. 7A-H. (A) Representative FACS plots of pre- and post-sorted mouse bone marrow monocytes that confirms sorting efficiency is accurate (n=3 independent experiments, using 3 mice each experiment). (B) Histograms showing pre-sorted and post-sorted ER-Hoxb8 clones (n=3 independent experiments, using 3 mice each experiment). (C,D) Bar graphs showing cell population, related to FIGS. 7B and 7D, respectively. (E) Representative FACS plots showing immunophenotypes of primary monocyte classes with previously known monocytic markers. (F) Heatmap of class-specific gene expression levels in primary monocytes. (G) Bar graphs showing BrdU incorporation of primary murine monocytes. (H) Bar graphs showing cell population, related to FIG. 7E.
Figure 8B:
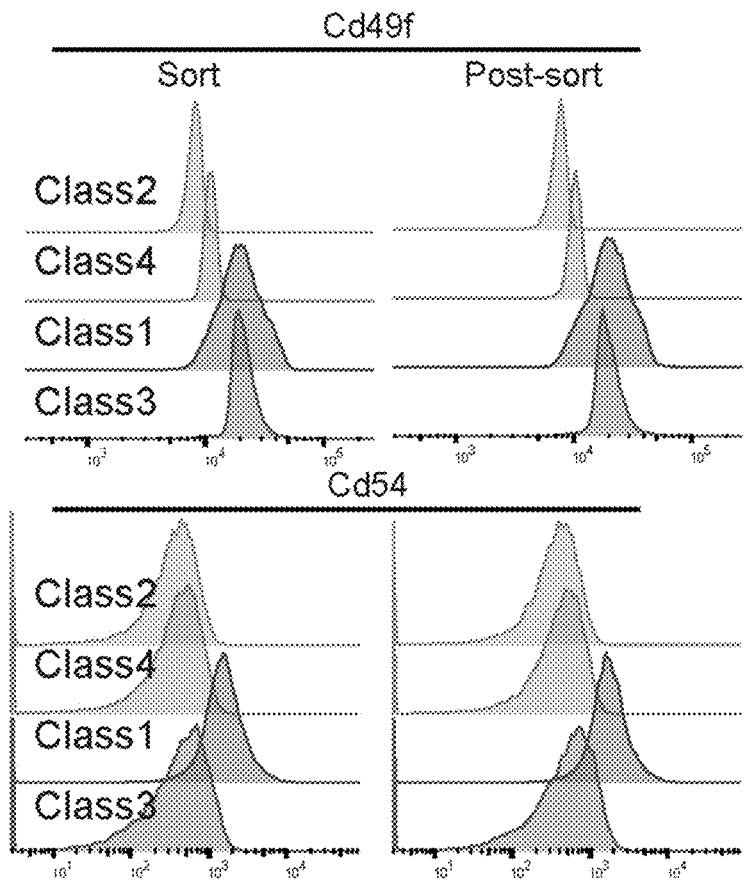
Figure 8C:
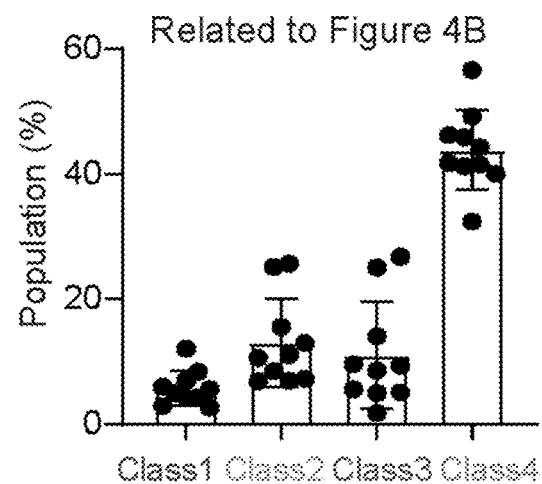
Figure 8D:
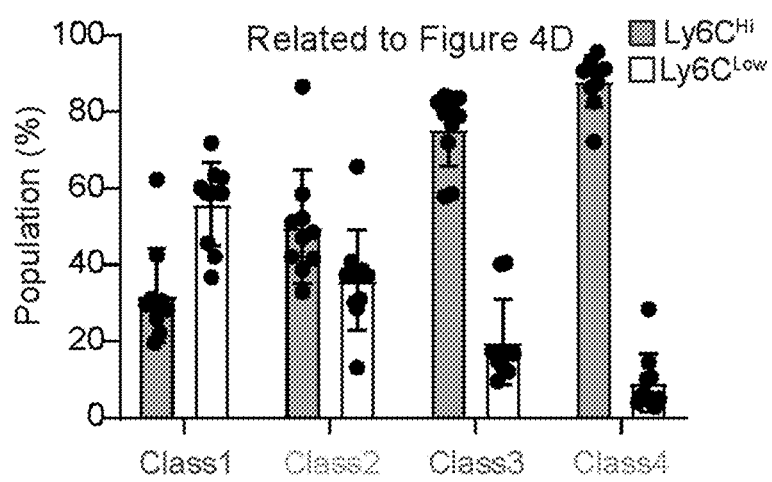
Figure 8E:
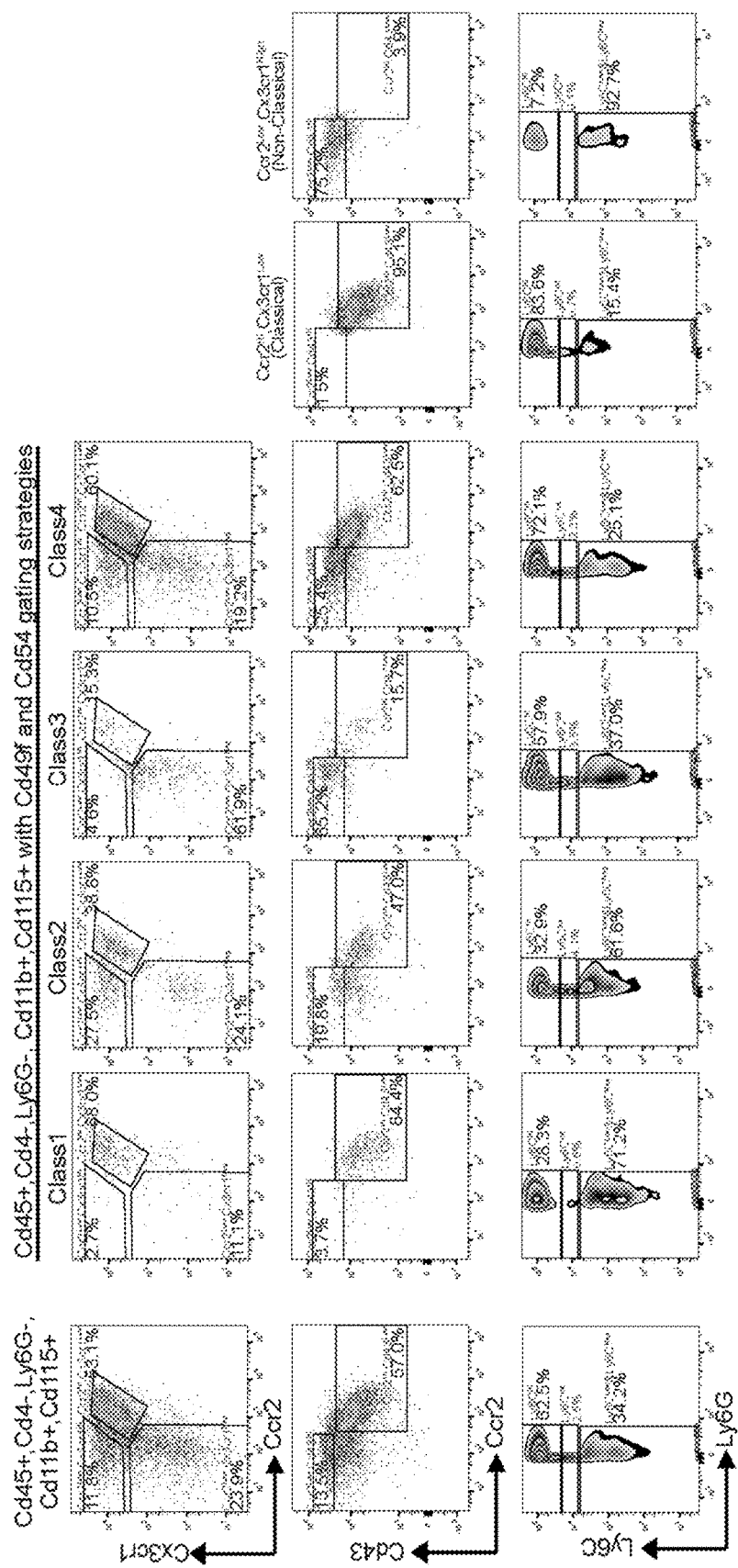
Figure 8F:
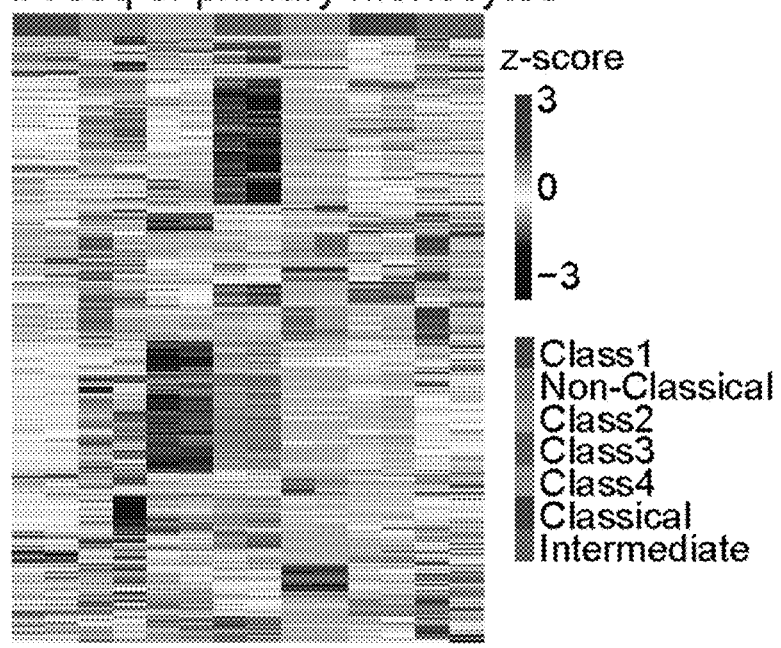

Example 4. Cd49f and Cd54 are Markers that Distinguish Monocytic Classes in Mouse and Human Blood To determine whether the four monocytic classes identified in the ER-Hoxb8 systems could be identified in primary monocytes, the RNA-seq data was used to identify cell surface markers that are differentially expressed in each class. Among these, Cd49f and Cd54 were candidates with associated antibodies against their gene products. The expressions of these genes in each monocytic classes were validated by RT-qPCR (FIG. 7A). Cd49f is an integrin known for cell surface adhesion and signaling. Cd54 is intercellular adhesion molecule 1 (ICAM1) known to bind to Cd11a and Cd11b. GMP clones that give rise to Class1 and Class3 monocytes had open chromatin at Cd54 and Cd49f in GMP, respectively (FIG. 6D) and had high expression of these genes in descendent monocytes. Cd49f and Cd54 were used to isolate each class of monocyte from primary mouse bone marrow (FIGS. 7B and 8A-8C). At steady-state, Class4 monocytes were most prevalent, whereas Class1 cells were least. ER-Hoxb8 monocytic clones express Cd49f and Cd54 according to class (FIG. 7C). Similar to transcriptomic profiling, sorted primary monocytes resemble classical, intermediate, and non-classical monocytes regarding Ly6C levels (FIGS. 7D and 8D). However, unexpectedly, the levels of Cx3cr1, Ccr2, and Cd43 of the monocytic subsets do not correlate with previously known monocytic classes (FIG. 8E). To better understand the correlation between our defined monocytic subsets to previously known classification, RNA-seq of primary murine monocytes was performed using our Cd49f and Cd54 sorting schema and the Classical and Non-Classical schema. Although similarities were observed between Class1/Class2 with Non-Classical and Class3/Class4 with Classical primary monocytes (FIG. 8F), they did not correlate by gene expression suggesting that the functionally defined classification schema groups cells distinctively from the classical and non-classical monocyte categories.

Figure 7E:
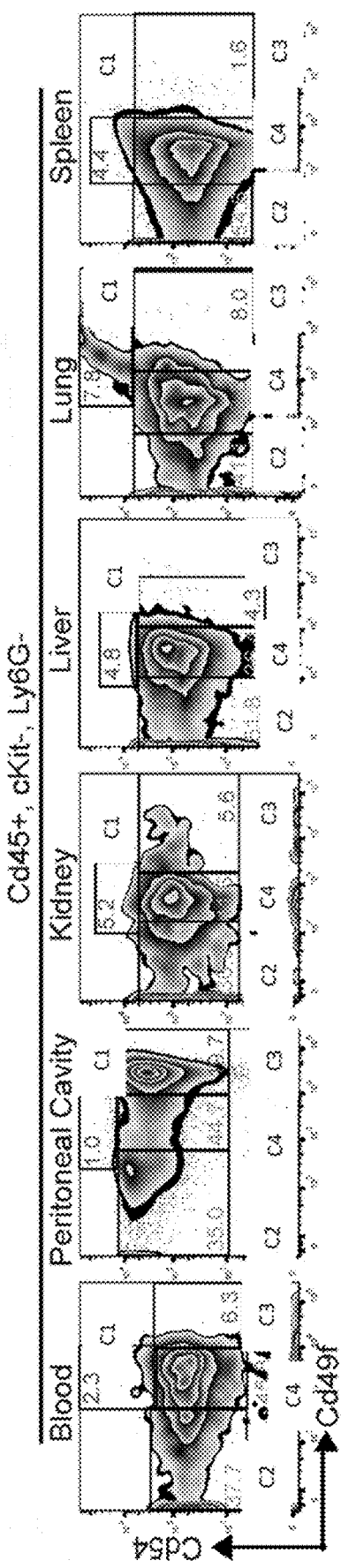
Figure 7F:
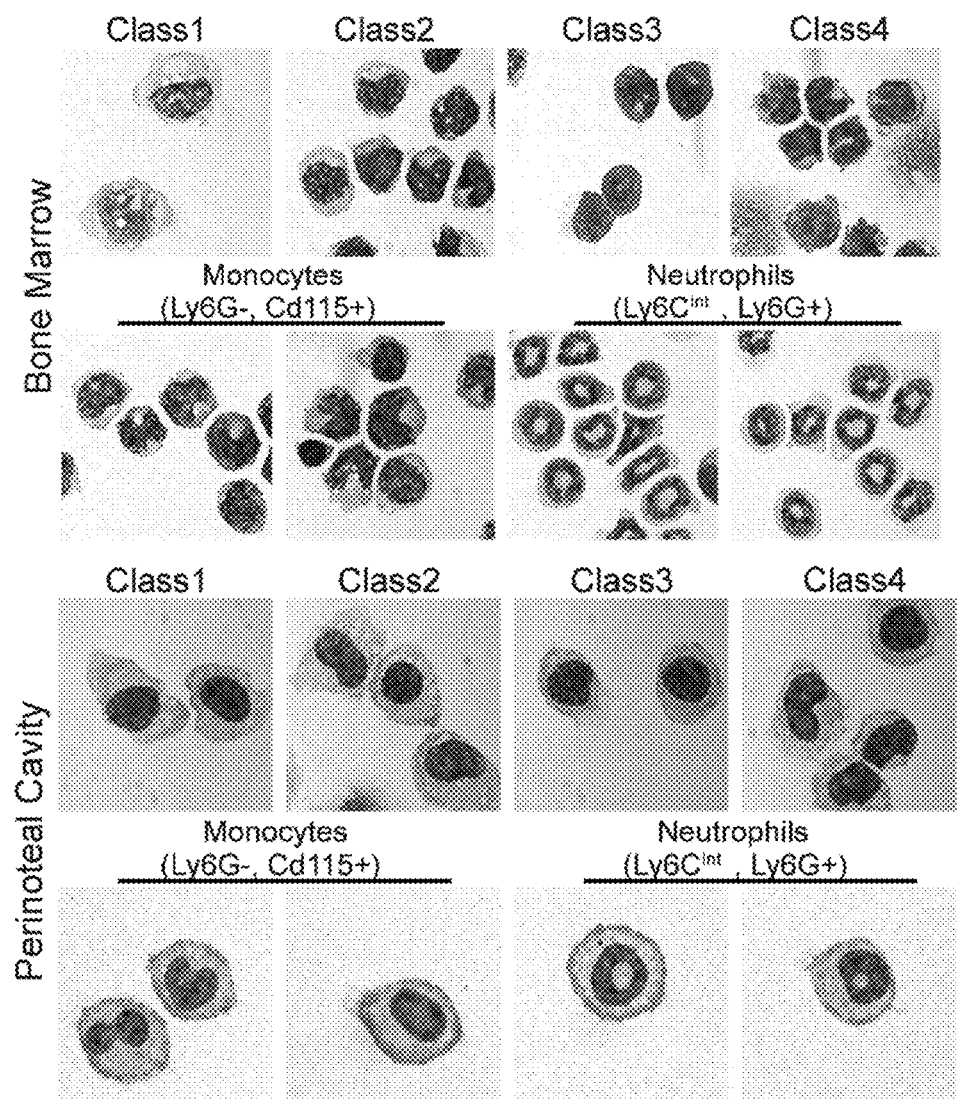
Figure 7G:
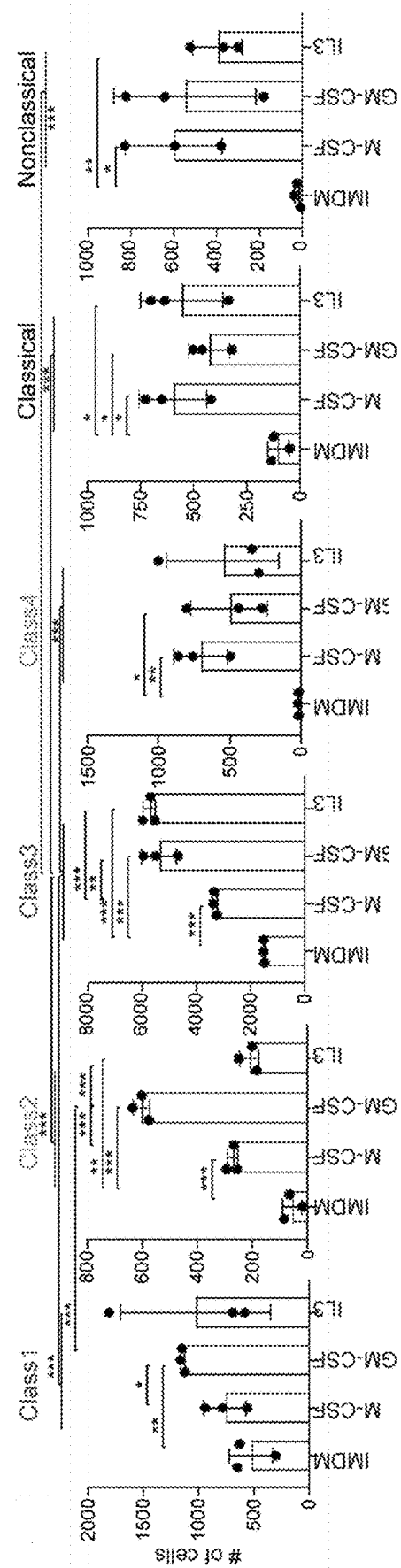
Figure 8G:
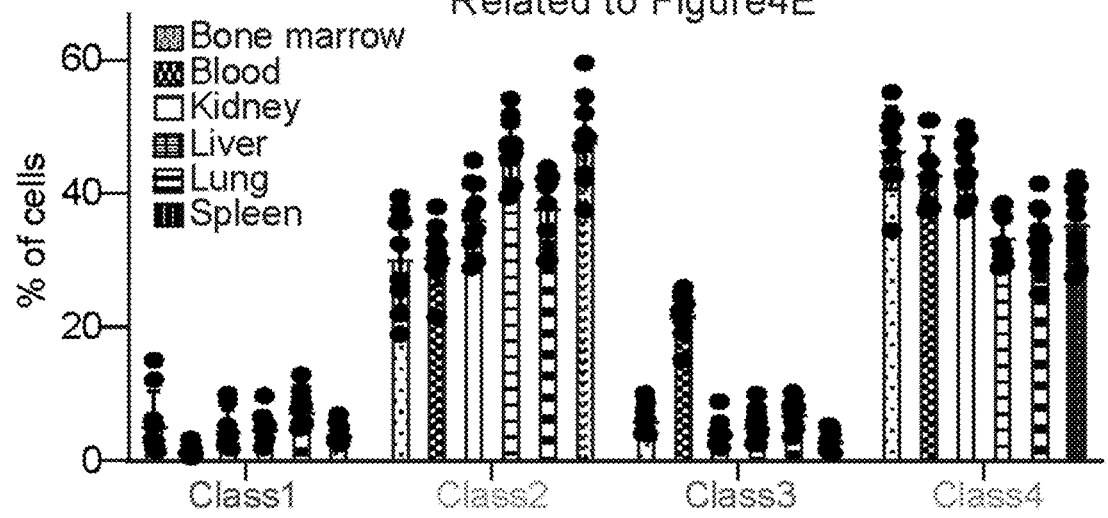
Figure 8H:
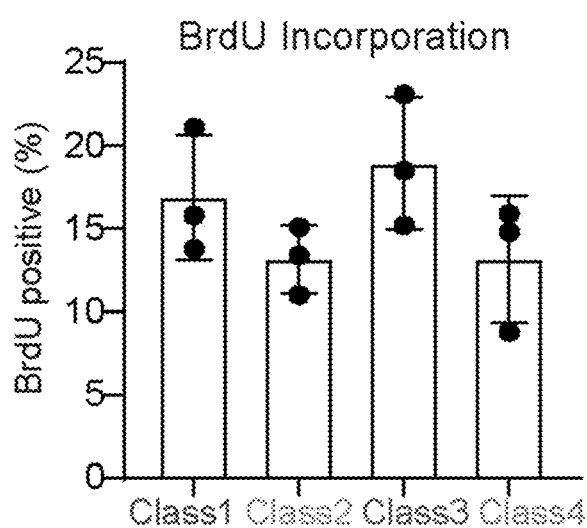

Using Cd49f and Cd54 as markers, four primary monocyte subsets were able to be sorted from different tissues (FIG. 7E). Fluorescence minus one controls for each tissue were used to gate each monocytic subset. Similar proportions of blood monocyte classes in multiple tissues were observed (FIG. 8G). The sorted cells had morphologic features of monocytes in all subsets after Wright-Giemsa staining (FIG. 7F). In addition, BrdU incorporation showed that Class1 through Class4 primary monocytes had similar proliferation rates in C57/B16 mice (FIG. 8H).

Next, whether these primary monocytic subsets have different preferential expansion in response to growth factors such as M-CSF, GM-CSF, or IL3 was examined. To examine the response to these growth factors, the sorted Class1-4 primary monocytes were cultured in M-CSF, GM-CSF, and IL-3 (FIGS. 7G and 9A-9C). Interestingly, Class1-4 monocytes have different preferential expansion in response to growth factors in vitro. For example, sorted Class2 primary monocytes preferentially respond to GM-CSF and Class3 monocytes have a more robust response to GM-CSF, M-CSF and IL-3 compared to the other Classes. Of note, monocytes isolated based on Classical and Non-classical immunophenotype have no such selective response, indicating that our monocyte Class schema provides biologically distinctive groups.

Figure 9A:
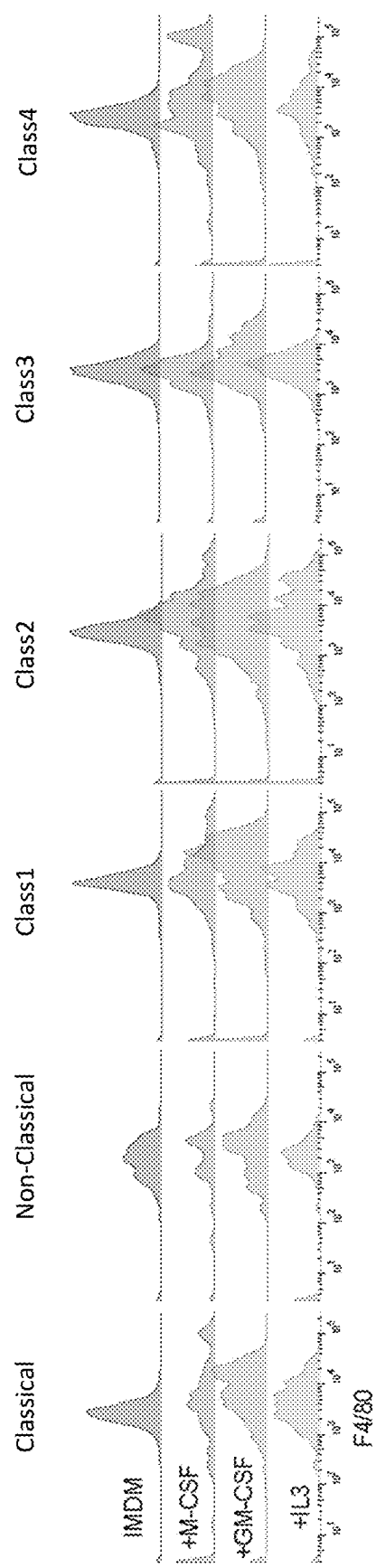
FIGS. 9A-F. Depicts four functional monocytes that can be classified in mouse and human, related to FIG. 7. (A-C) Histograms showing expression of maturation markers when culturing primary monocytes in growth factor supplemented media. (D) Bar graphs comparing cell population between monocyte classes from bone marrow of Nr4a1 KO mice. (E) Bar graphs showing the absolute number of monocytic cells in Nr4a1KO cells. (F) Bar graphs representing cell population of human blood monocyte classes, related to FIG. 4G (n=2 independent experiments, using 2-3 donors each experiment).
Figure 9B:
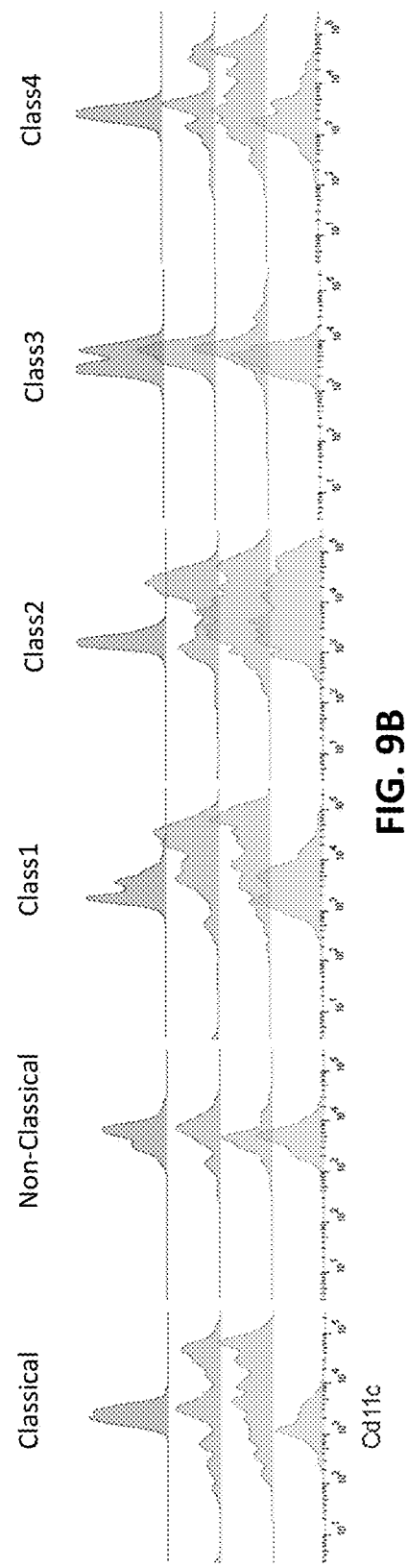
Figure 9C:
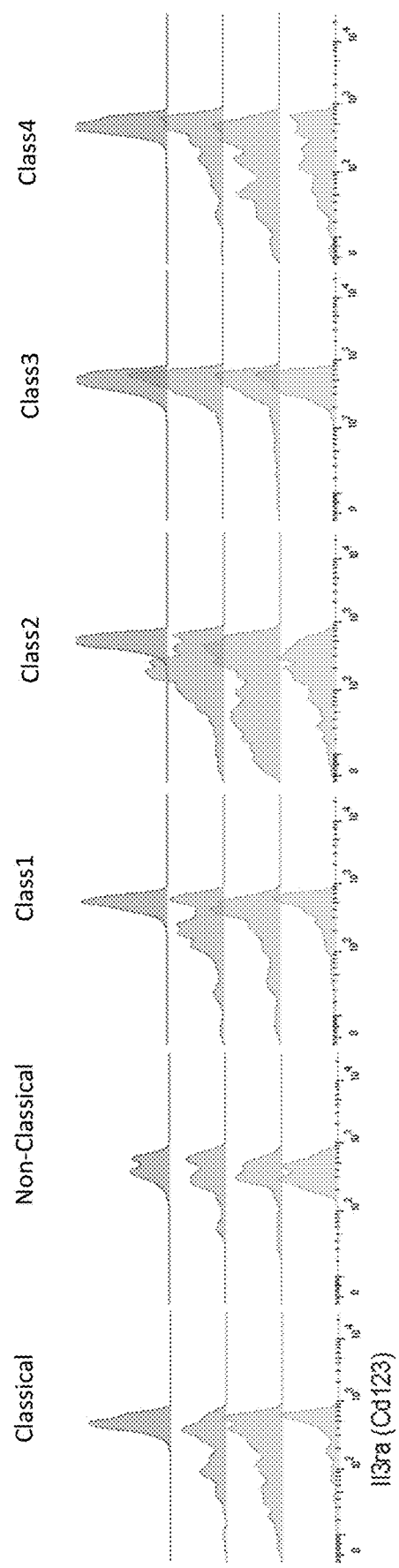
Figure 9D:
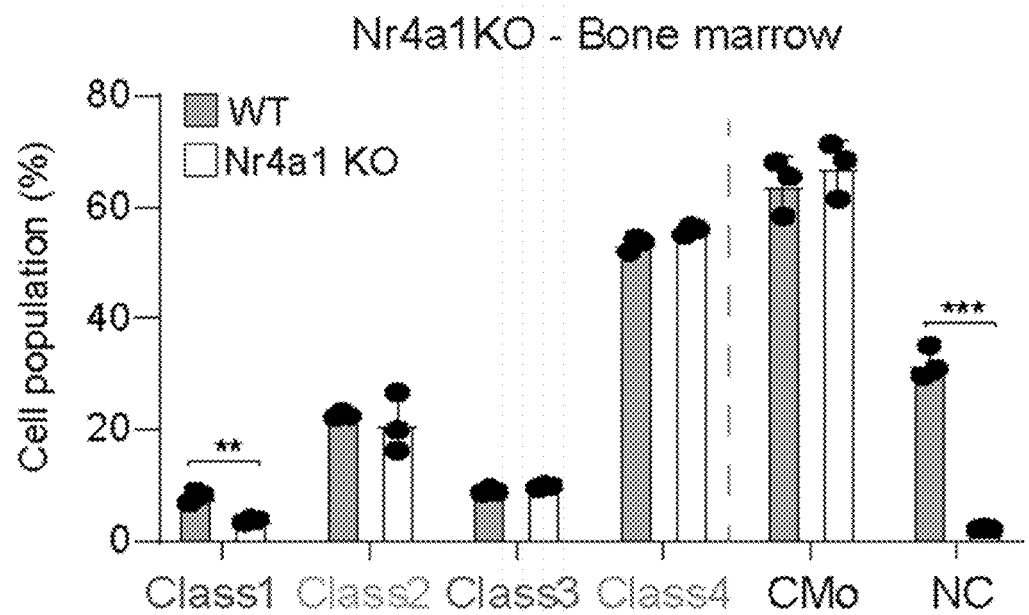
Figure 9E:
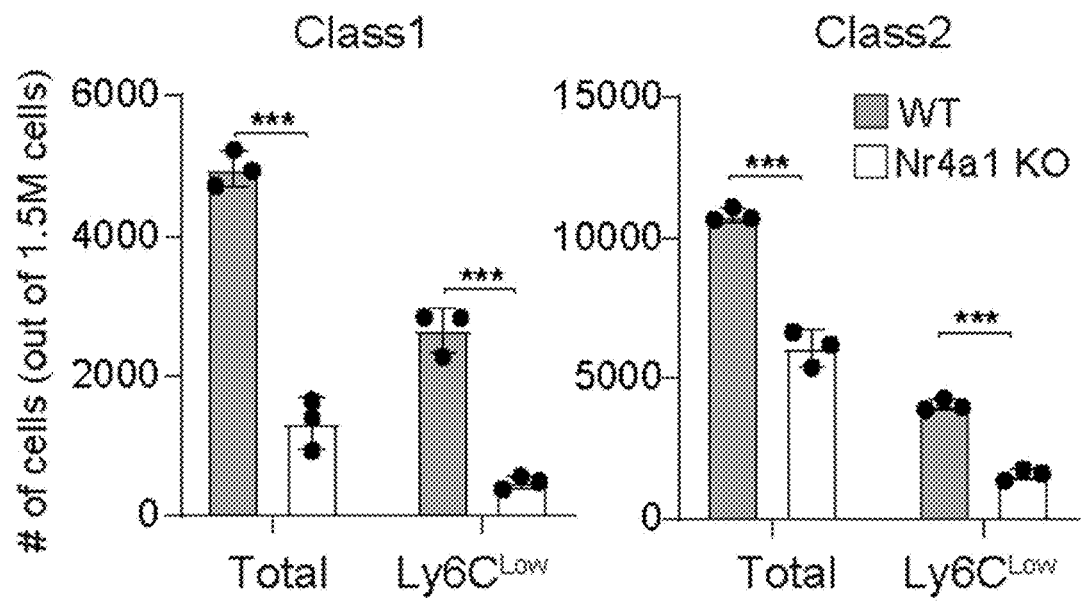

To further analyze our defined monocytic classes, Nr4a KO mice were used. Nr4a1 is a master transcriptional regulator for Ly6C$^{low}$ monocytes. The proportion of Class1 and Class2 monocytes was significantly less in Nr4a1KO bone marrow compared with WT mice (FIGS. 9D-9E). The degree of reduction in each class reflected the abundance of Ly6C$^{low}$ cells. Nr4a1 affects the generation of Ly6C$^{low}$ cells across the classes of monocytes.

Figure 7H:
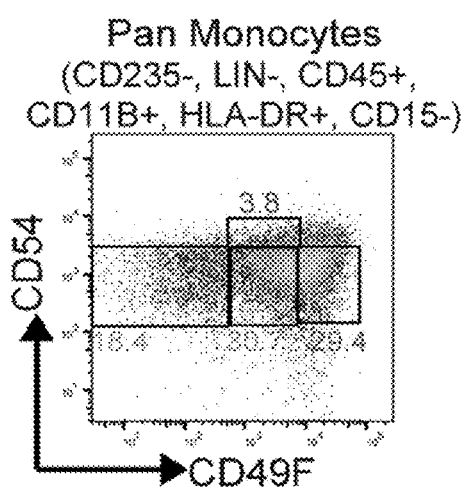
Figure 7I:
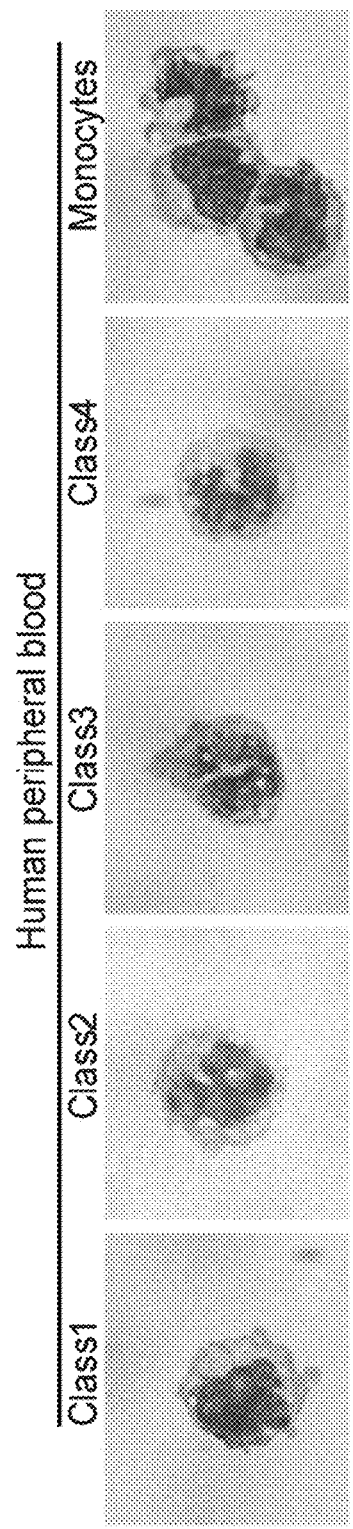
Figure 9F:
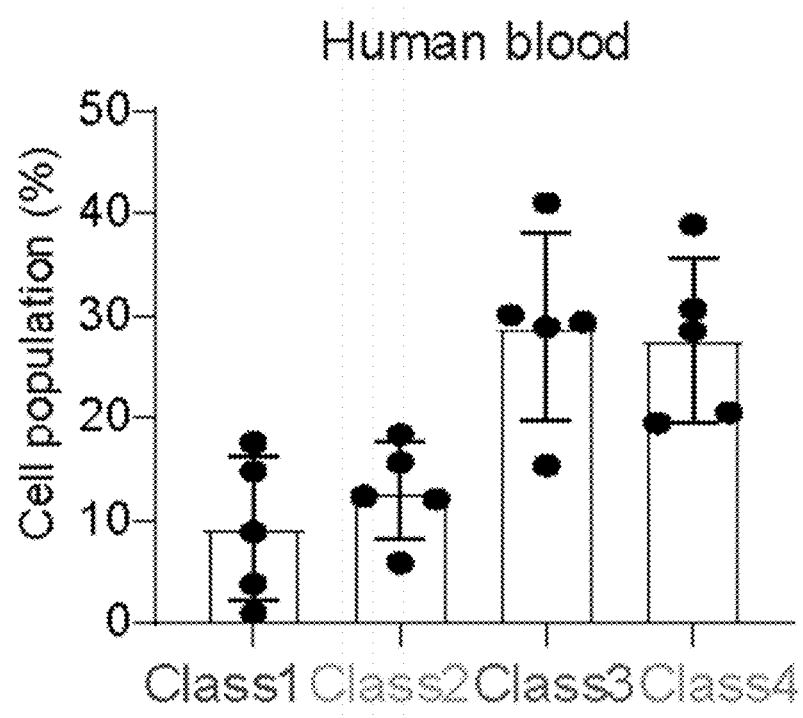

Whether these monocytic classes identified in mouse also exist in human peripheral blood was examined. CD49F and CD54 could again be used as markers to discriminate the four classes of monocytes in human blood (FIGS. 7H-7I and 9F). The marker genes identified in the ER-Hoxb8 system can be used to isolate subsets of both mouse and human primary monocytes.

Figure 10A:
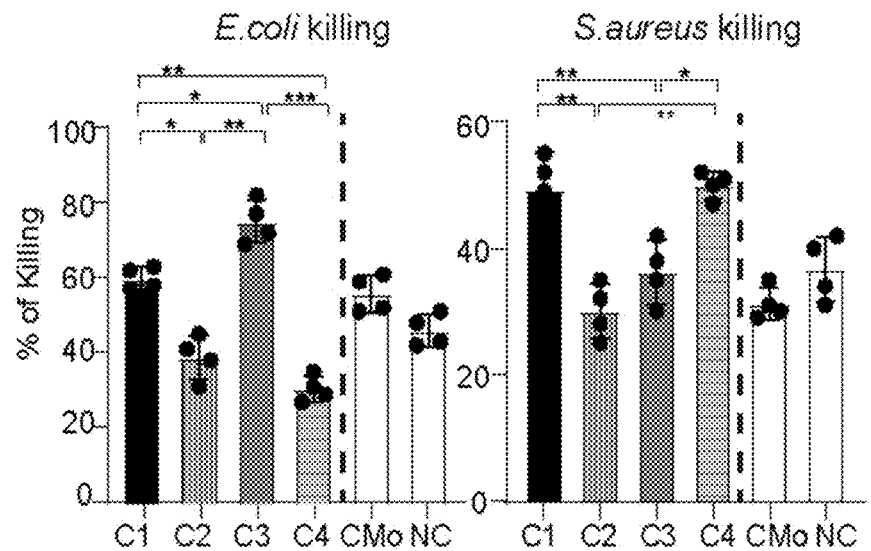
FIGS. 10A-I depicts each monocytic class exhibiting distinct phenotypes upon bacterial infection. (A-F) Bar graphs showing each class of primary murine monocytes have varying capacities to perform monocytic functions (n=4 independent experiments, in triplicate technical replicates). Killing assays, cytokine production ELISA, and ROS assays were done in vitro. Bacterial uptake and phagocytosis were done in vivo. (G) Heatmap summarizing in vitro and in vivo functional assays of primary murine monocytes. (H, I) Bar graphs showing each class of human peripheral blood monocytes have varying capacities to phagocytose in vitro (n=2 independent experiments, using 2-3 donors each experiment, in duplicate technical replicates). *P<0.05, P<0.01, and *P<0.005.
Figure 10B:
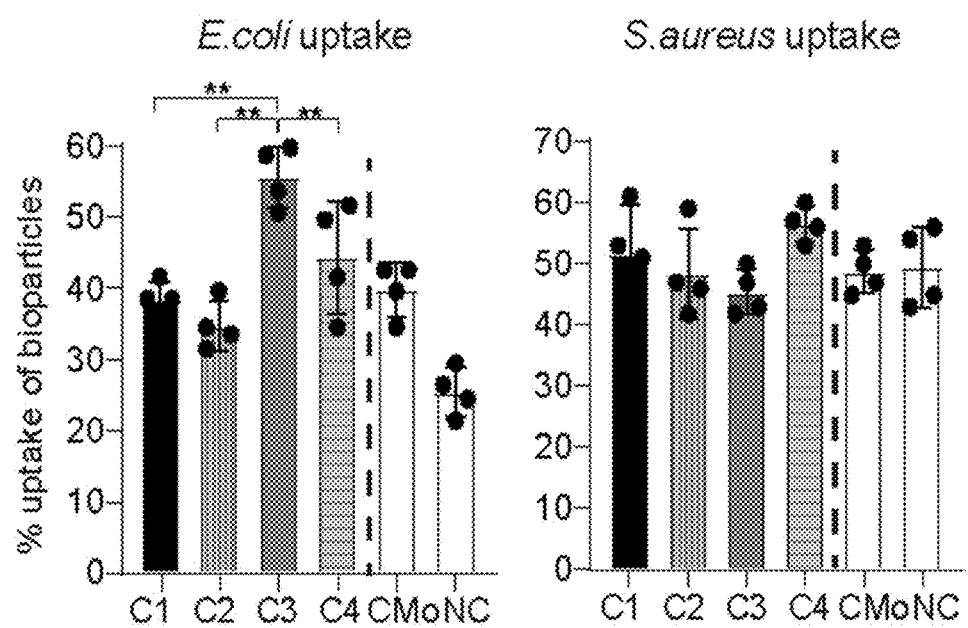
Figure 10C:
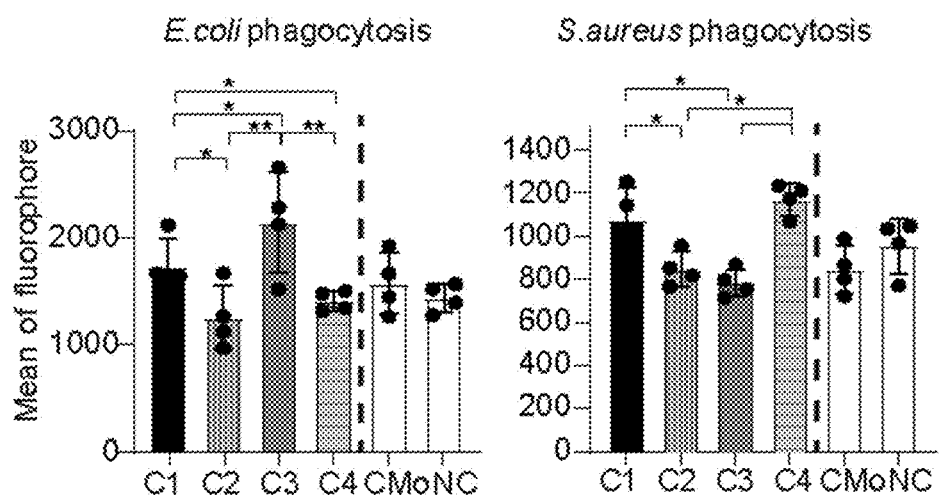
Figure 10D:
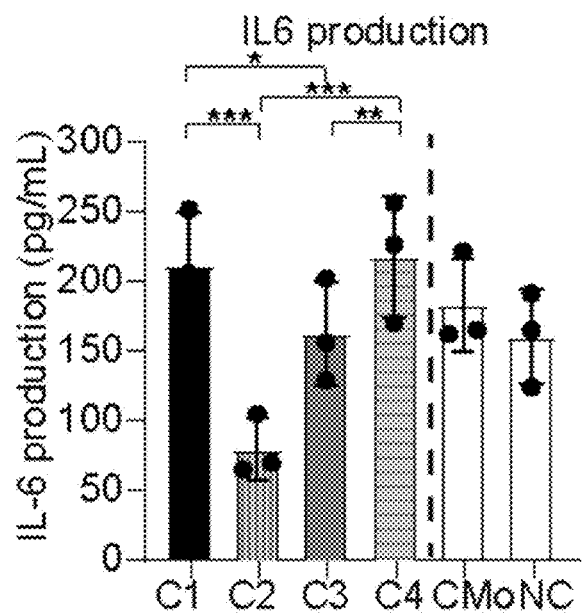
Figure 10E:
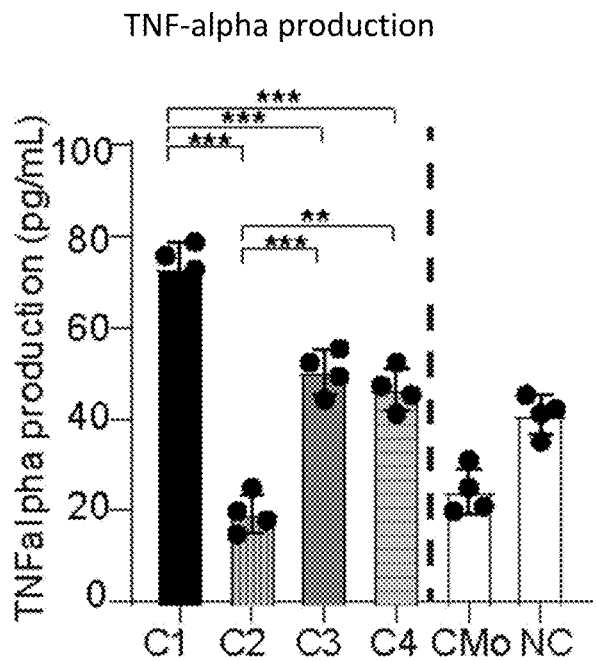
Figure 10F:
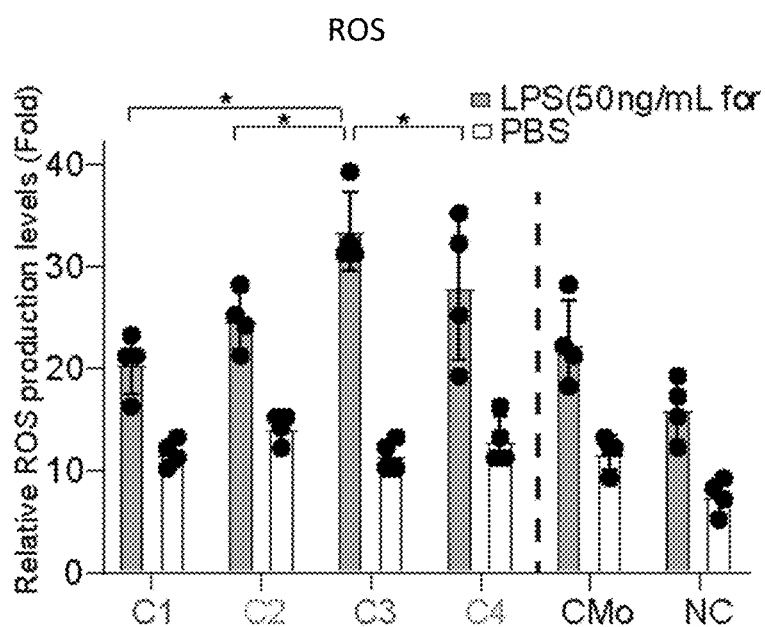
Figure 10G:
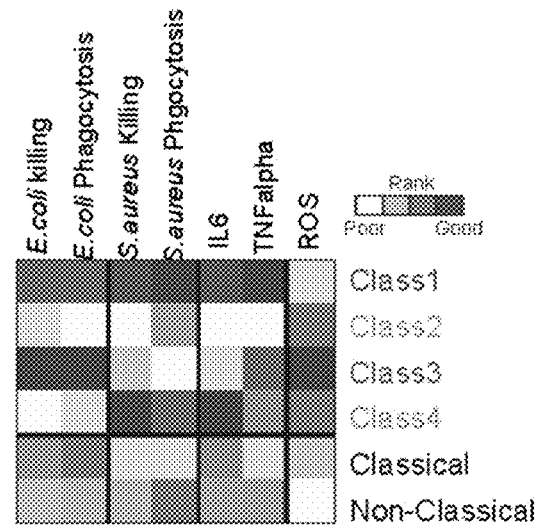

Example 5. Each Primary Monocyte Class Exhibits a Distinct Phenotype Upon Bacterial Infection The same in vitro and in vivo functional assays were performed that were used with ER-Hoxb8 derived monocytes on primary mouse monocytes sorted based on Cd49f and Cd54 expression. Similar to ER-Hoxb8 monocytic clones, the primary monocytes showed distinct functional patterns (FIGS. 9A-F). Class3 monocytes were efficient at killing E. coli and ROS generation whereas Class4 monocytes preferentially cleared S. aureus over E. coli in addition to Class1 being efficient at killing both bacteria and TNFalpha production. Notably, the most efficient functional monocytes from our defined subgroups were more robust in the tested functions than cells isolated using traditional Classical and Non-Classical monocyte isolation methods (FIG. 10G).

Figure 10H:
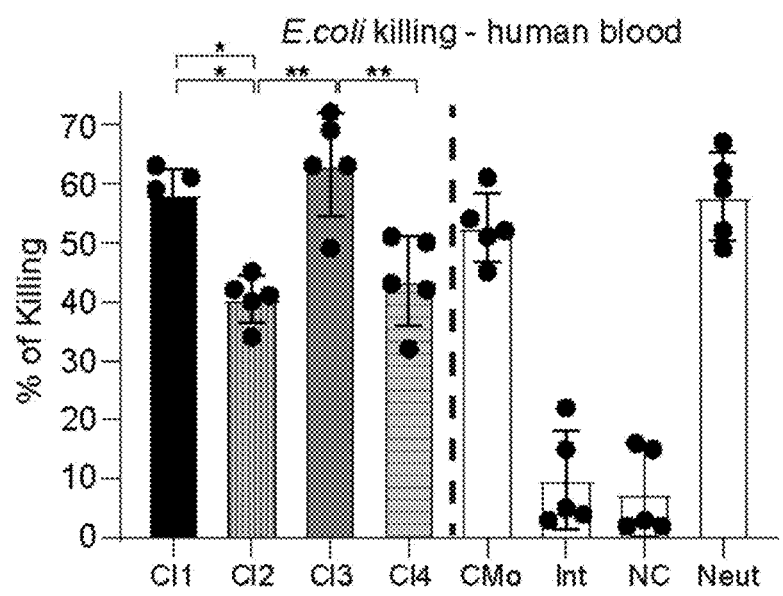
Figure 10I:
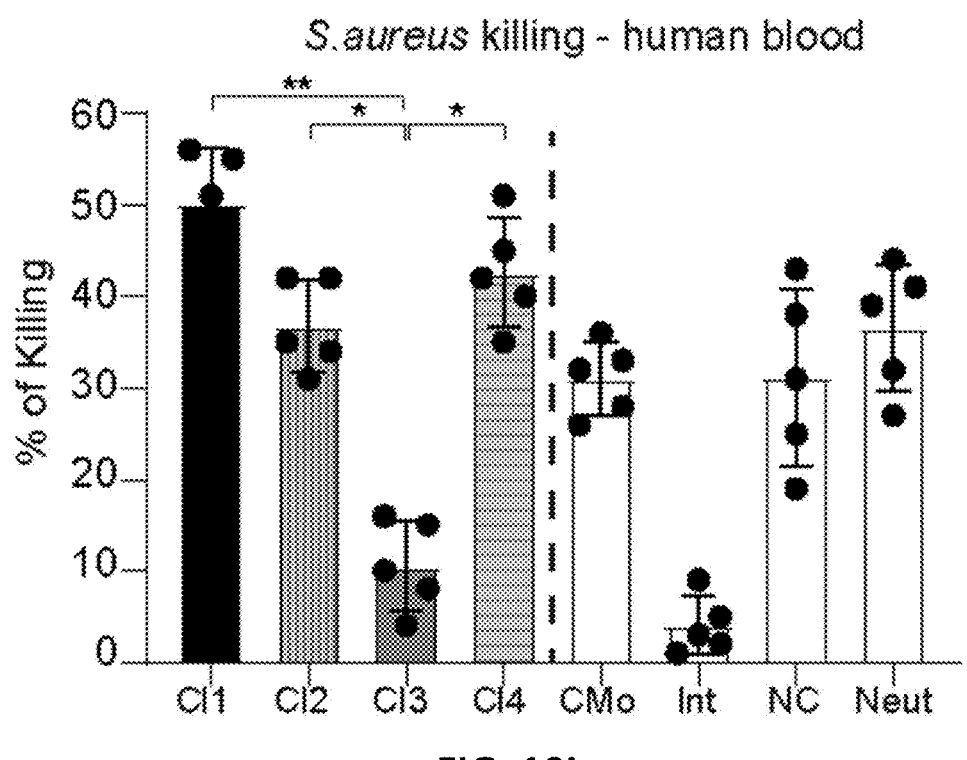

Next, whether the functional phenotypes of sorted monocytic classes found in mouse also occur in human was examined. Indeed, similar functional distinction was observed in capacity of each class to conduct bacterial killing (FIGS. 10H and 10I). These resolve the functional attributes of monocytes in more than traditional Classical and Non-Classical categories.

Example 6. Limited Plasticity of Functional Blood Monocyte Subsets was Observed

Figure 11A:
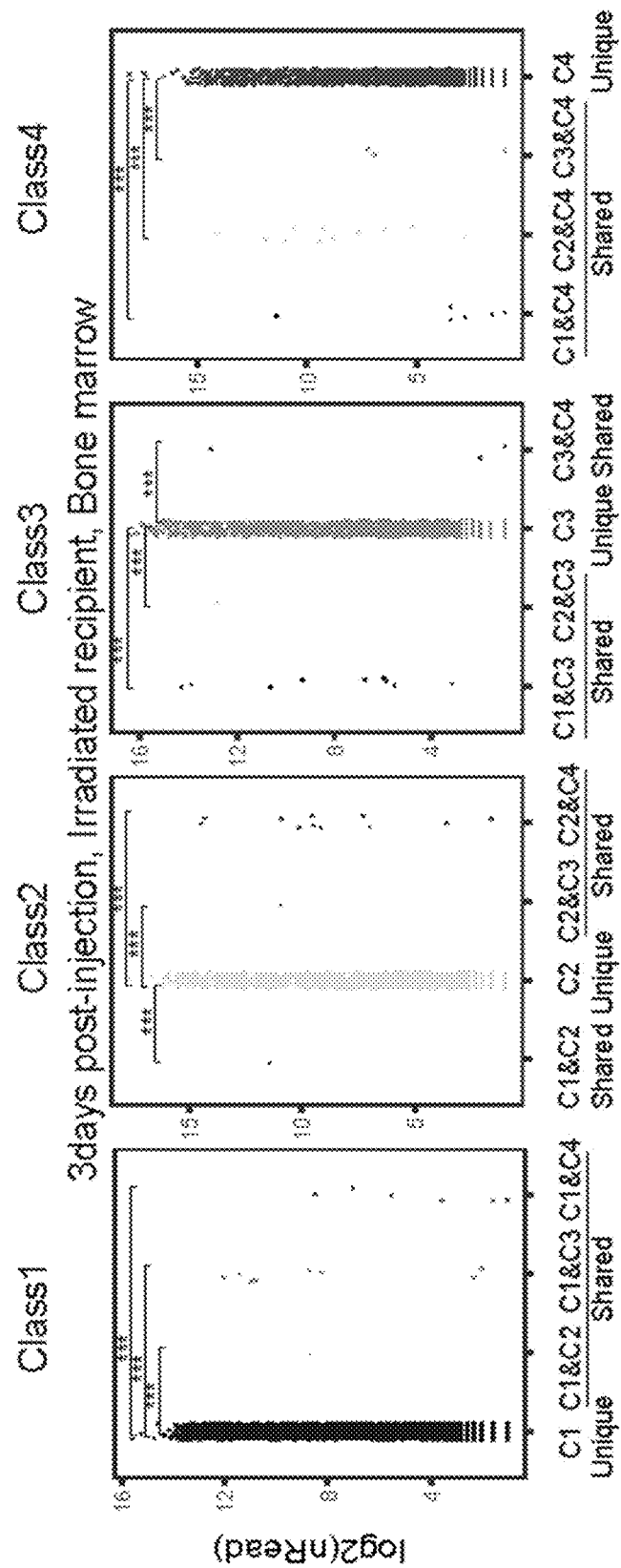
FIGS. 11A-I. Depicts limited plasticity of functional blood monocyte subsets. (A) Representative violin plots displaying the log 2 number of reads for barcodes in each monocytic class of irradiated recipient bone marrow (n=5 mice). (B) A Venn diagram showing the number of overlapping and unique barcodes that are derived from GMPs found in monocytic classes of irradiated recipient bone marrow (n=5 mice). (C) Representative violin plots of non-irradiated recipient bone marrow (n=4 mice). (D) A Venn diagram of non-irradiated recipient bone marrow (n=4 mice). (E) Representative violin plots of non-irradiated recipient spleen (n=2 mice). (F) A Venn diagram of non-irradiated recipient spleen (n=2 mice). (G) Representative violin plots of sub-lethally irradiated recipient bone marrow at 7 days post-injection (n=2 mice). (H) A Venn diagram of sub-lethally irradiated recipient bone marrow at 7 days post-injection (n=2 mice). Hypergeometric test shows P<0.005 on the significance of overlapping barcodes. (I) A graph showing changes in Ly6C levels of each class primary monocytes upon different amounts of bacterial infection in vivo. See FIGS. 12A-J.
Figure 11B:
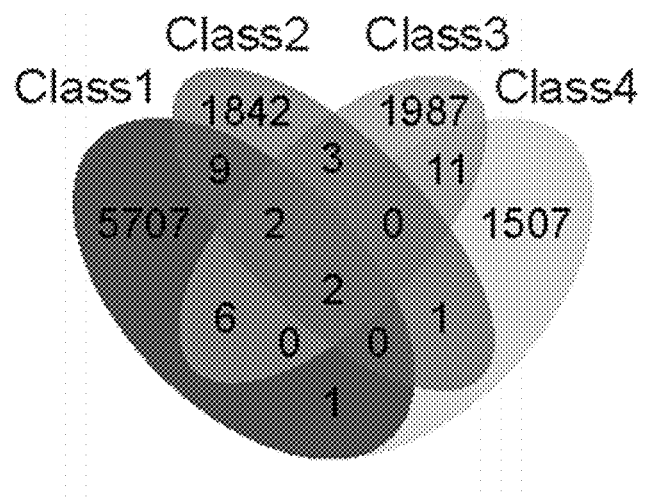

It was next determined whether there was evidence for interconversion between cell classes or shifts in fate under homeostasis, primary GMPs were transduced with a high-complexity barcode library, pRSI9-U6-(sh)-UbiC-TagRFP-2A-Puro, which enables the high-resolution clonal tracing. These barcoded GMP cells were transferred into lethally irradiated mice and allowed to differentiate for 72 hours prior to isolation of blood monocytes. The monocytes were sorted into the four different classes of primary monocytes based on the Cd49f and Cd54 analytic schema. Cells in each class were then analyzed by DNA sequencing to define if individually labeled GMP yielded monocytes restricted to a particular class or randomly contributed to all four subsets. Strikingly, barcodes were restricted to a particular monocyte subclass (FIG. 11A) often with multiple cells in the Class bearing the same barcode. While barcodes overlapping subsets were found, they were significantly under-represented with small numbers of reads compared with hundreds to thousands of reads within a Class (FIG. 11B) indicating that they are most likely from contamination during sorting.

Figure 11C:
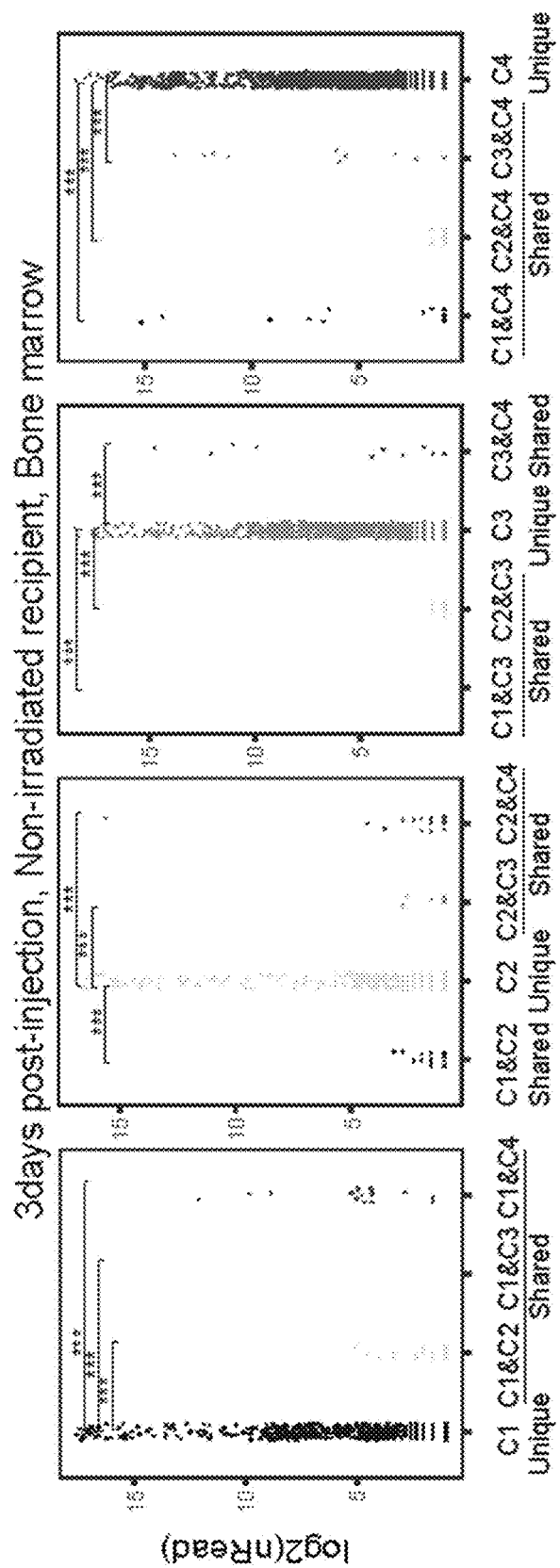
Figure 11D:
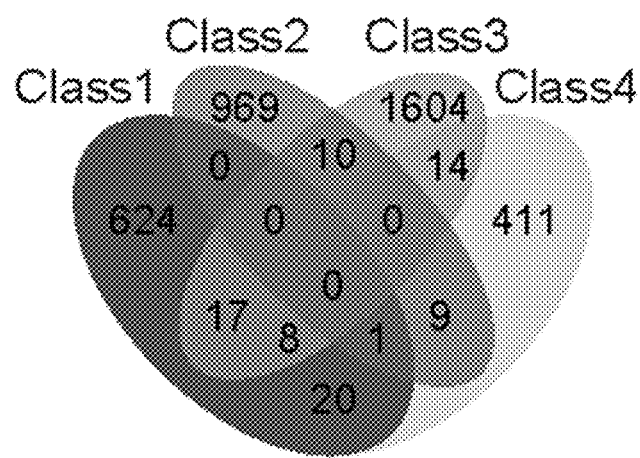
Figure 11E:
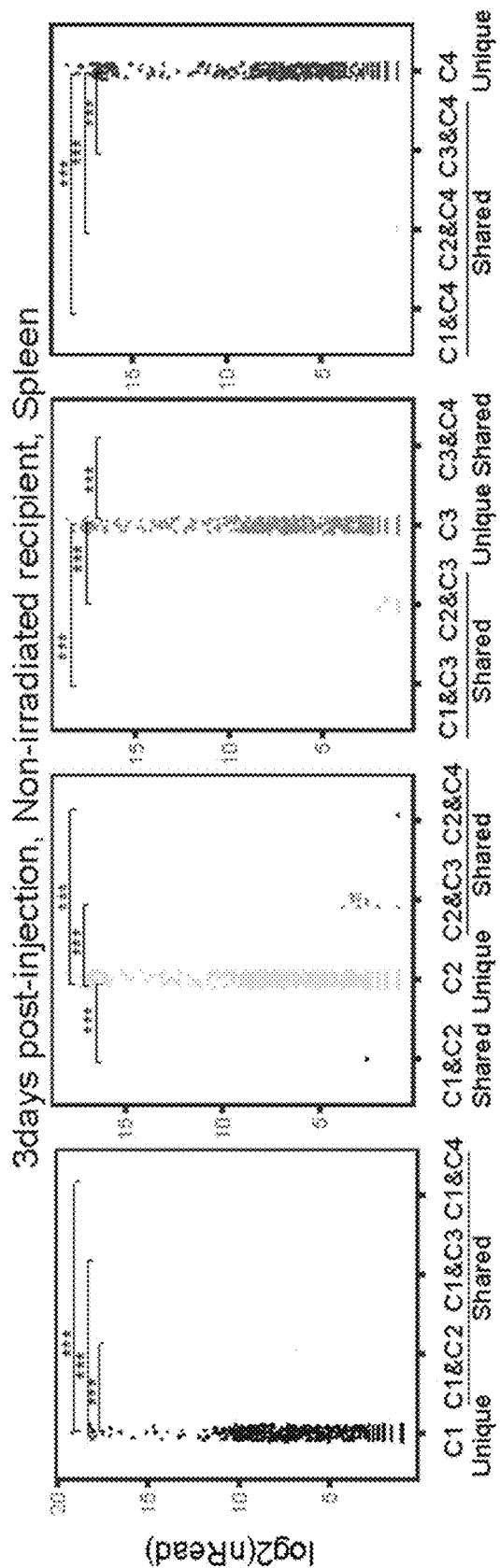
Figure 11F:
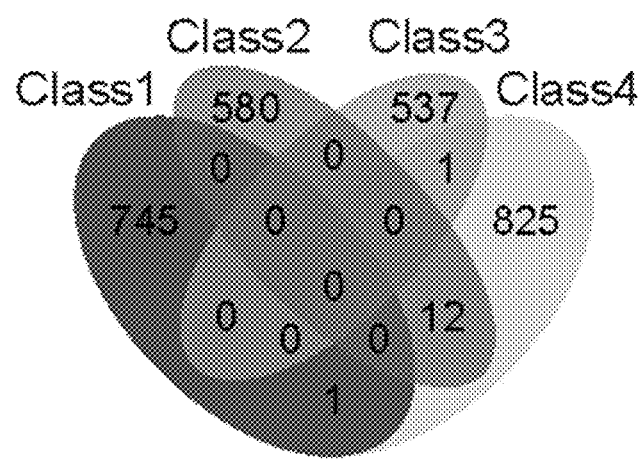
Figure 11G:
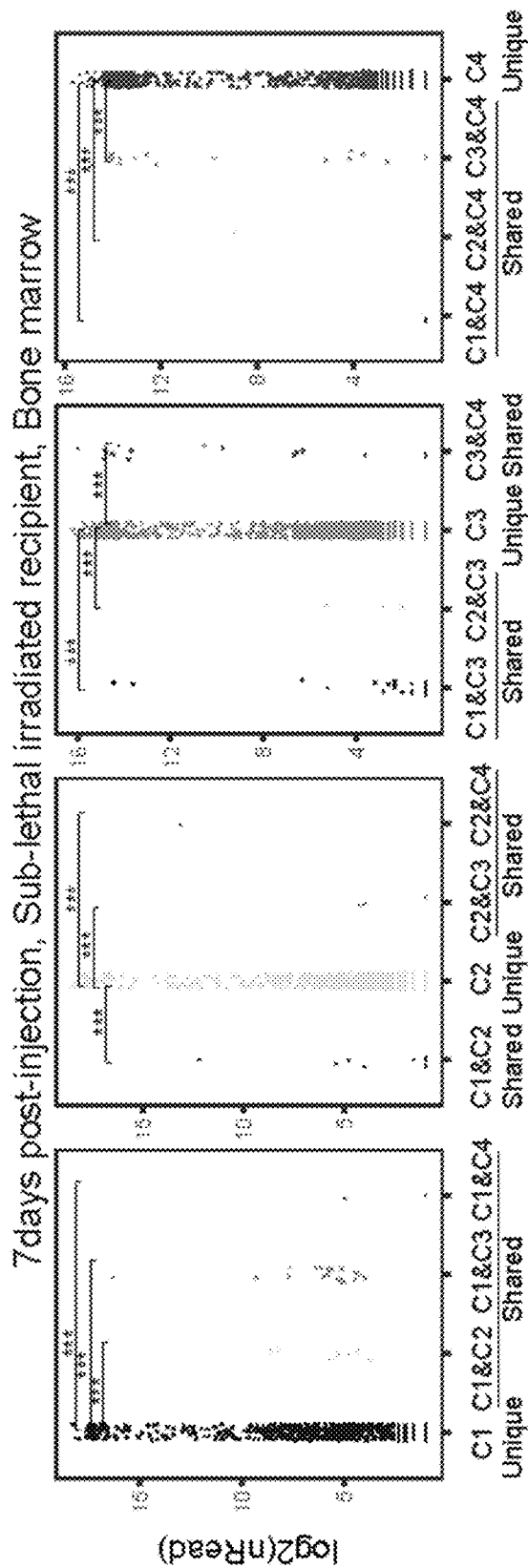
Figure 11H:
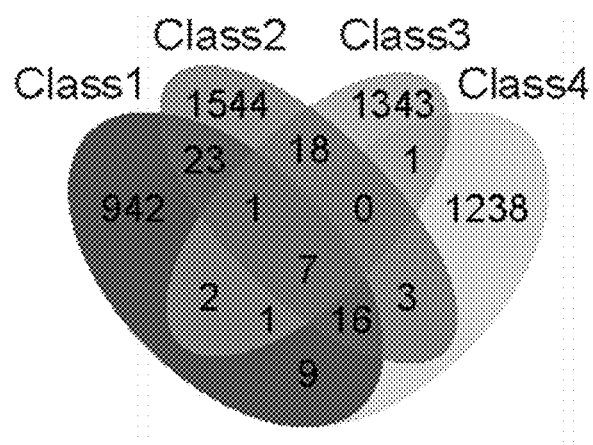

In addition, the in vivo steady-state context using the recipient mice without any irradiation was used. Consistently, no interconversion was observed between cell classes under homeostasis not only in bone marrow (FIGS. 11C-11D), but also in other tissues such as spleen and lung (FIGS. 11E-11F). Additionally the plasticity of monocyte subsets was examined at a longer time point. Barcodes were restricted to a particular monocyte subclass even after one week post injection (FIGS. 11G-11H). These data demonstrate that GMPs are rigidly programmed to become specific functional monocytes with limited plasticity to contribute to multiple classes, at least under homeostasis or post-irradiation.

Whether limited plasticity also exists under conditions of stress was evaluated. Peptidoglycans of gram-negative E. coli or gram-positive S. aureus bacteria were added into the culture media during class specific GMP differentiation over 5 days. No changes were observed in surface expression of the indicator proteins, Cd49f and Cd54, and other key distinctively expressed monocyte markers, Ly6C, Cd115, F4/80, and MHCII (FIGS. 12A-12D). Similarly, expression levels of indicator proteins did not vary following bacterial infection both in vitro and in vivo (FIGS. 12E-12H).

Figure 11I:
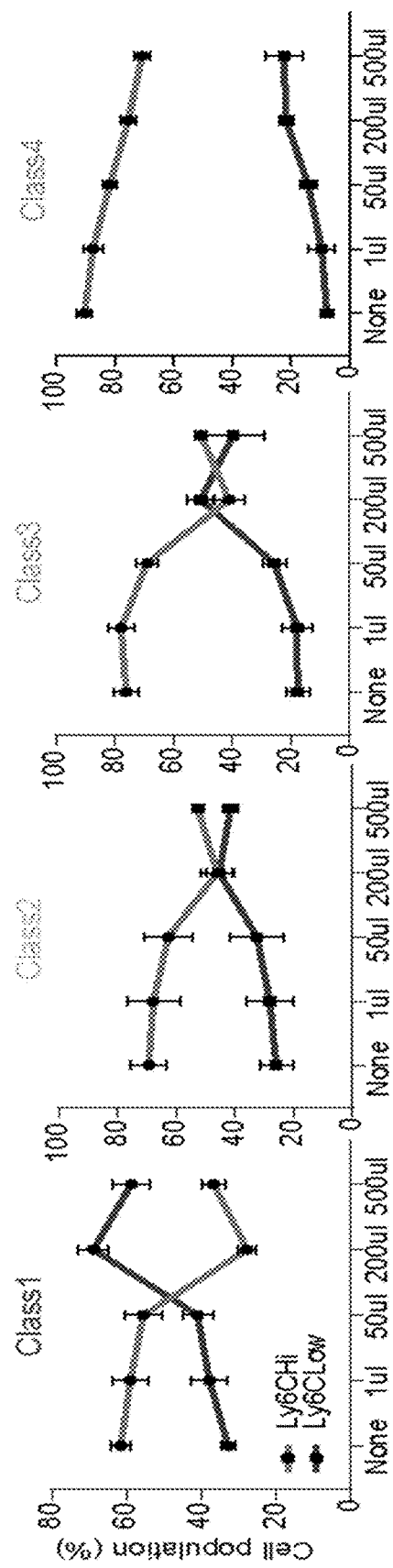
Figure 12A:
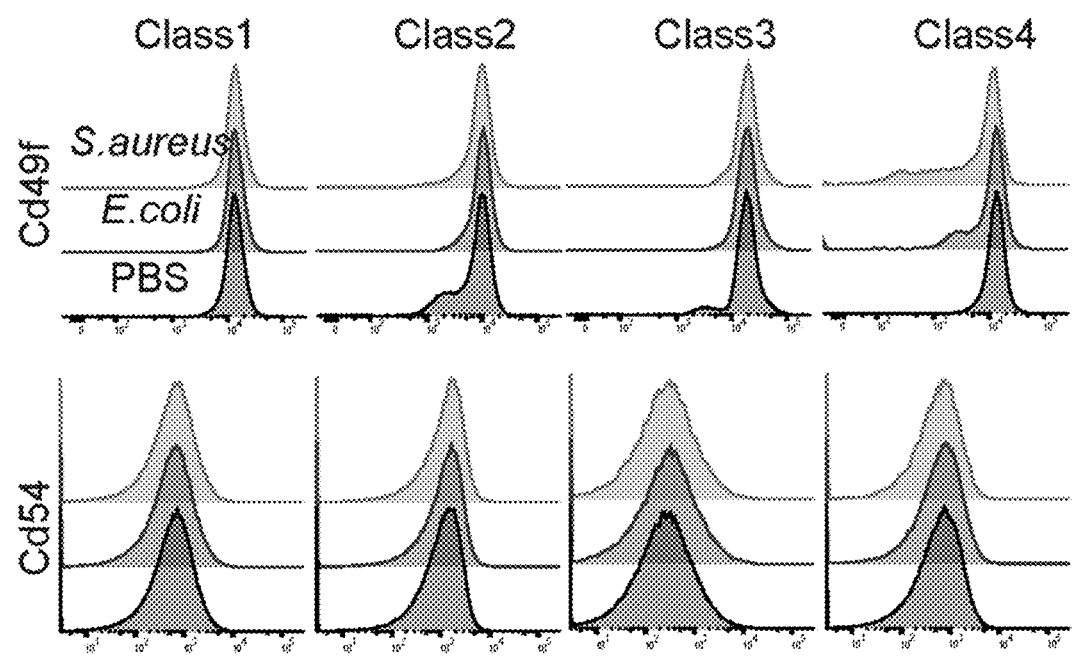
FIGS. 12A-J. Depicts limited plasticity of functional monocytes upon bacterial infection, related to FIG. 11. (A) Representative histograms showing no changes in Cd49f and Cd54 of Er-Hoxb8 clones before and after inflammatory conditions. (B) Representative FACS plots showing no changes in macrophage markers of ER-Hoxb8 clones before and after inflammatory conditions. (C) Bar graphs showing cell population of most representative quadrant, related to FIG. 12B (n=3 independent experiments, using 3 mice each experiment) (D) Representative FACS plots showing no changes in monocyte markers of ER-Hoxb8 clones before and after inflammatory conditions. (E,F) Representative FACS plots showing no changes in Cd49f and Cd54 expression of sorted mouse bone marrow monocytes after bacterial infection in vitro and in vivo, respectively (n=3 independent experiments, using 3 mice each experiment). (G,H) Bar graphs showing cell population of relevant monocyte classes, related to FIGS. 12E and 12F, respectively. (I,J) Bar graphs showing Ly6C$^{Low}$ cell population before and 3 hours after bacterial infection. Primary monocytes of each class were intravenously injected into WT and Ccr2 KO mice, respectively (n=3 independent experiments, using 2 mice each experiment).
Figure 12B:
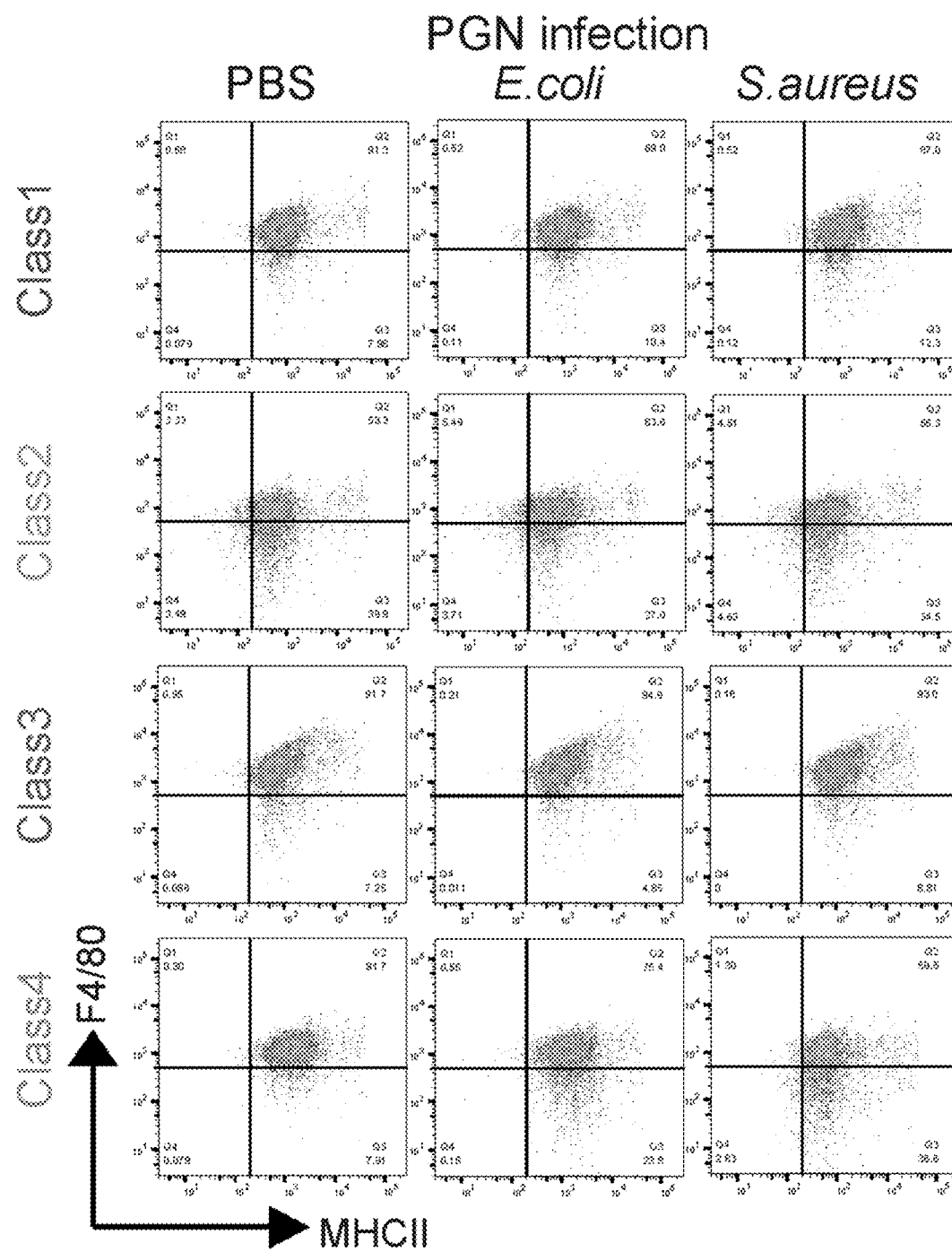
Figure 12C:
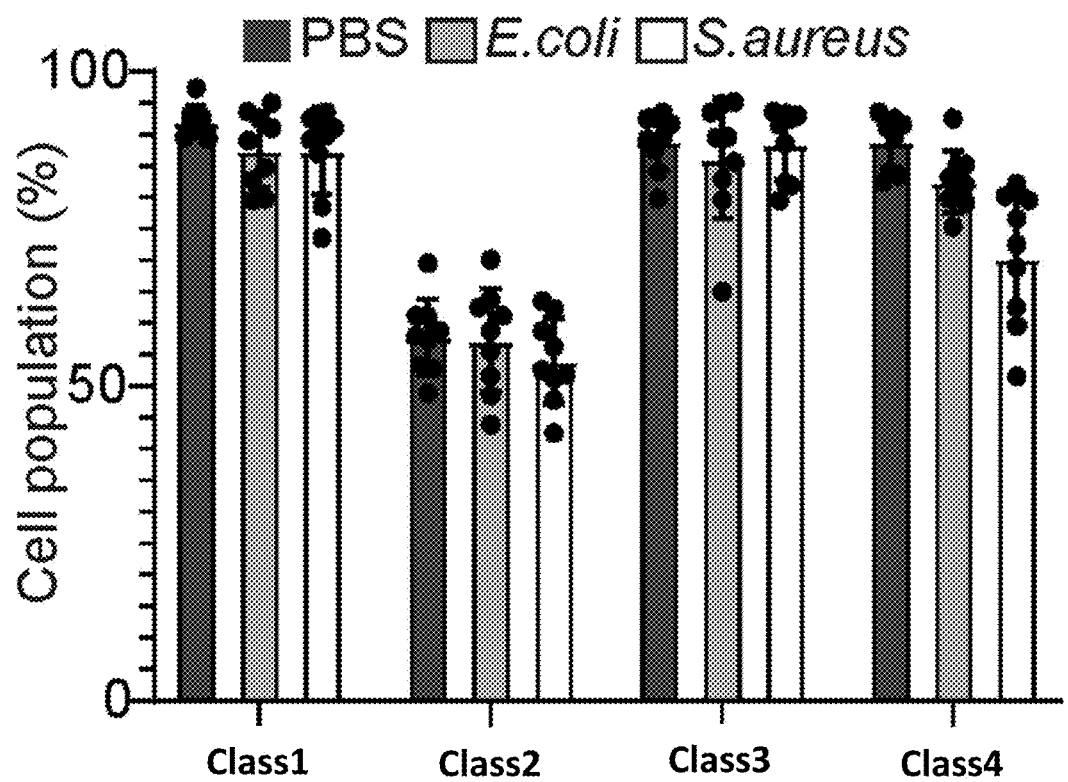
Figure 12D:
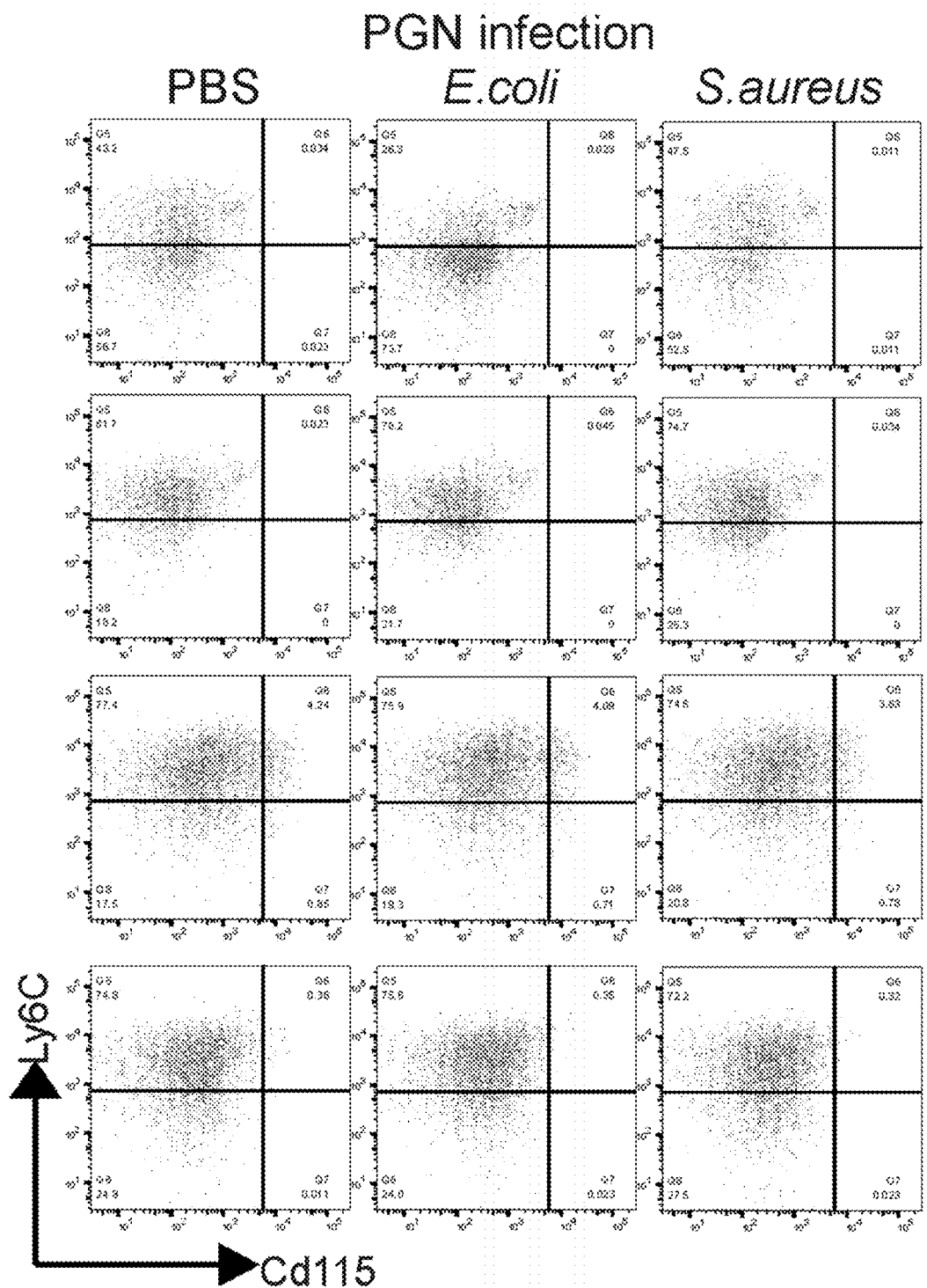
Figure 12E:
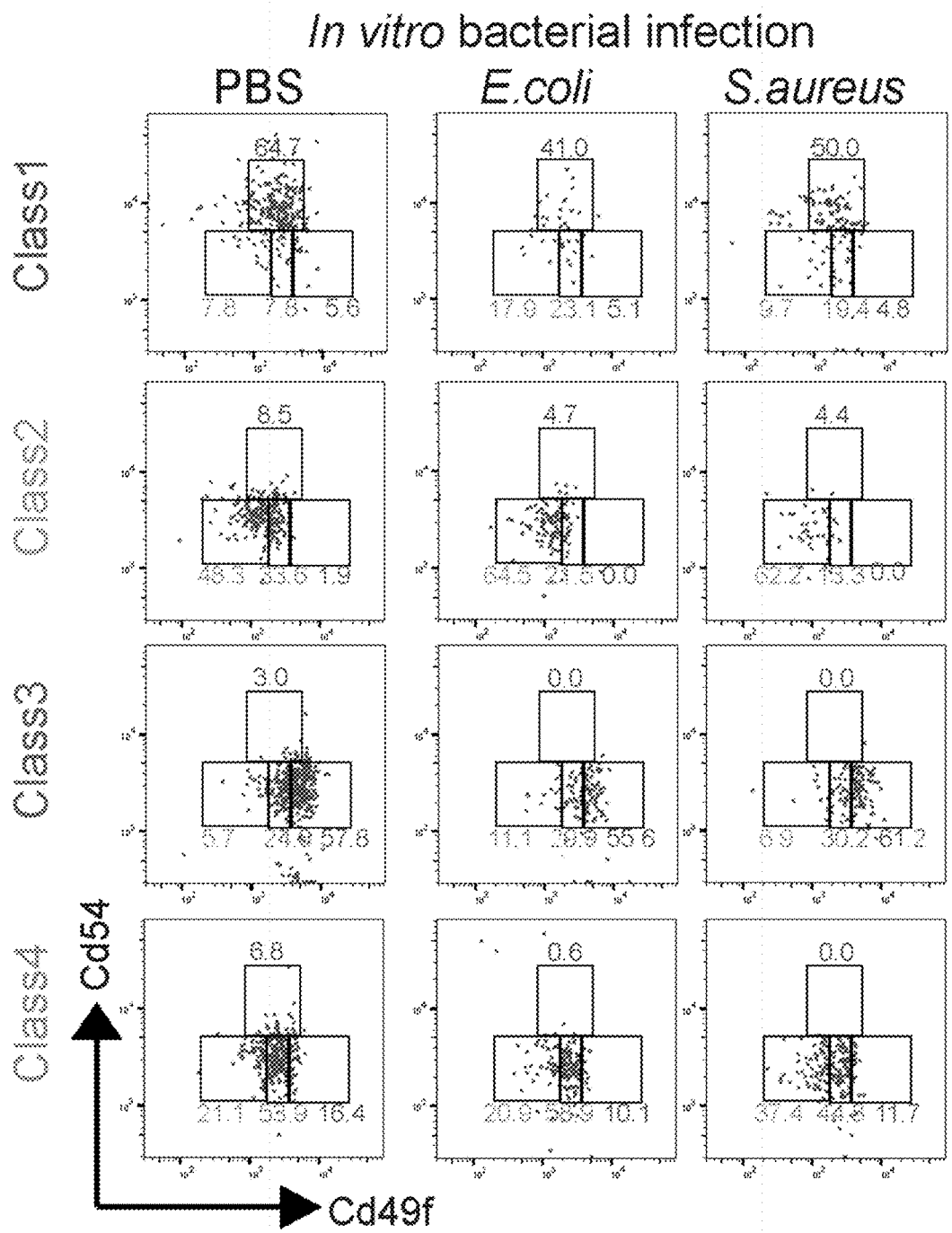
Figure 12F:
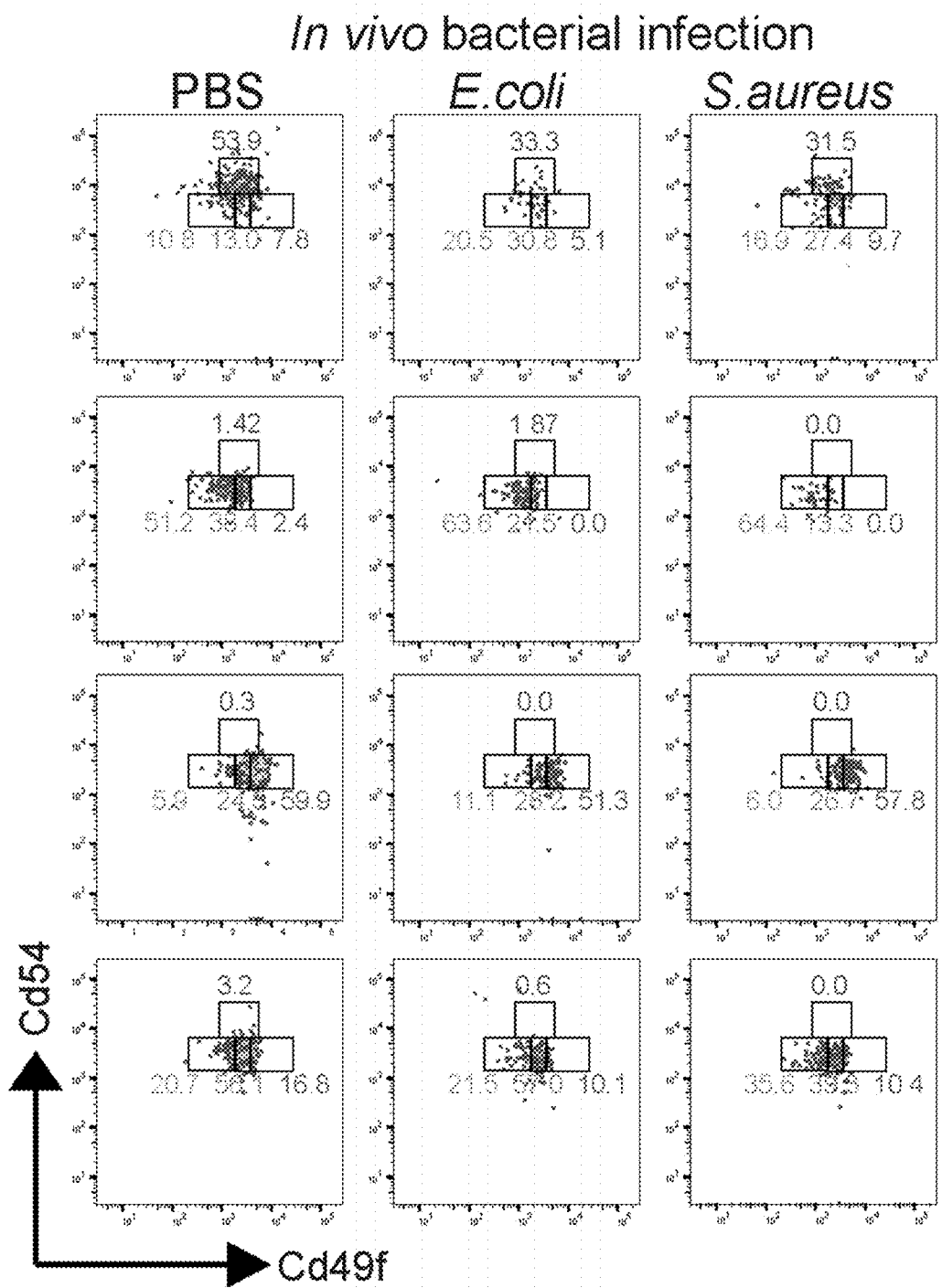
Figure 12G:
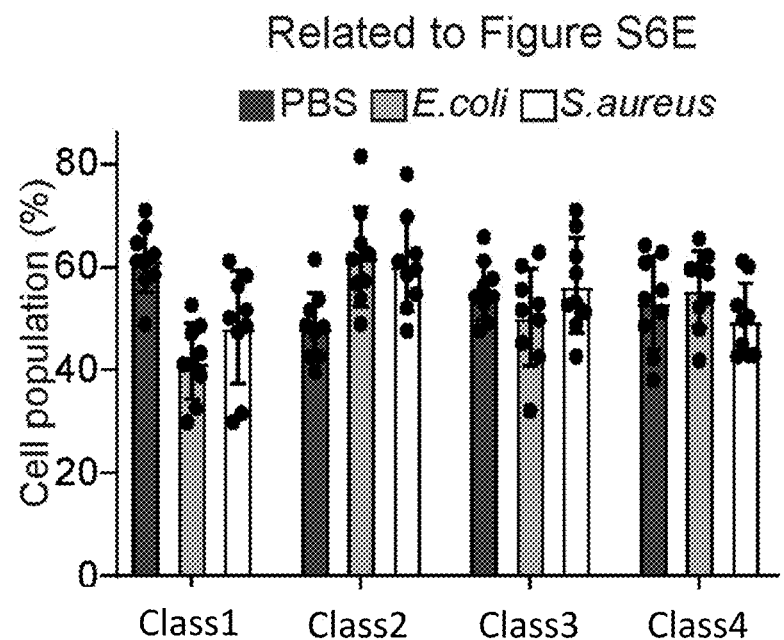
Figure 12H:
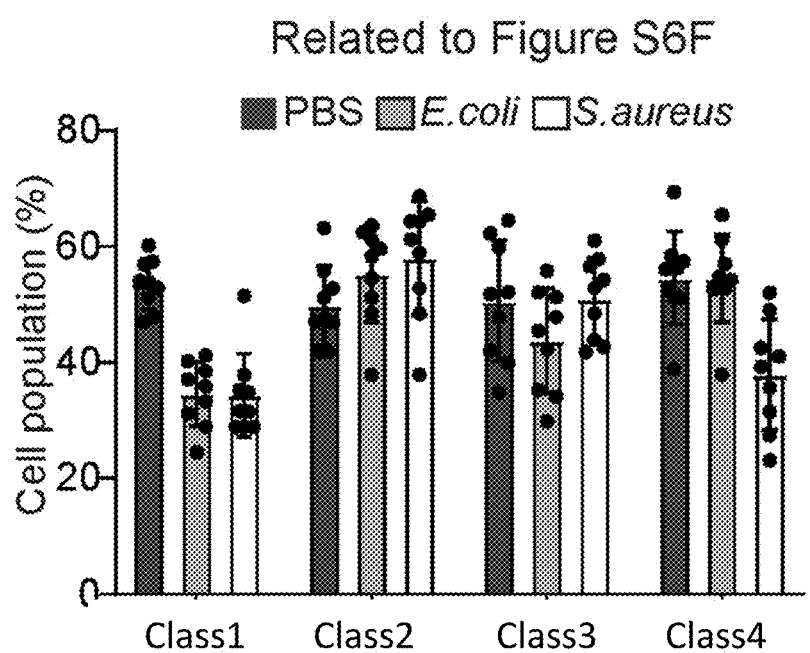
Figure 12I:
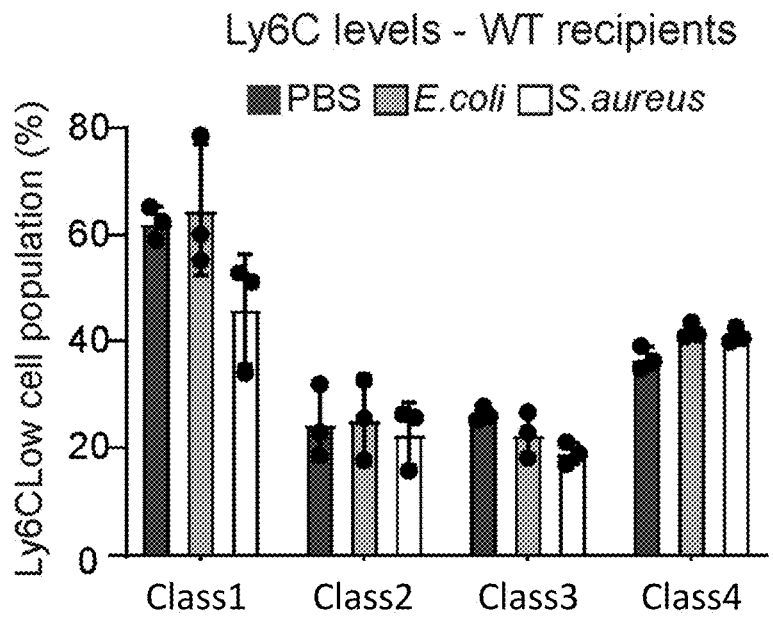
Figure 12J:
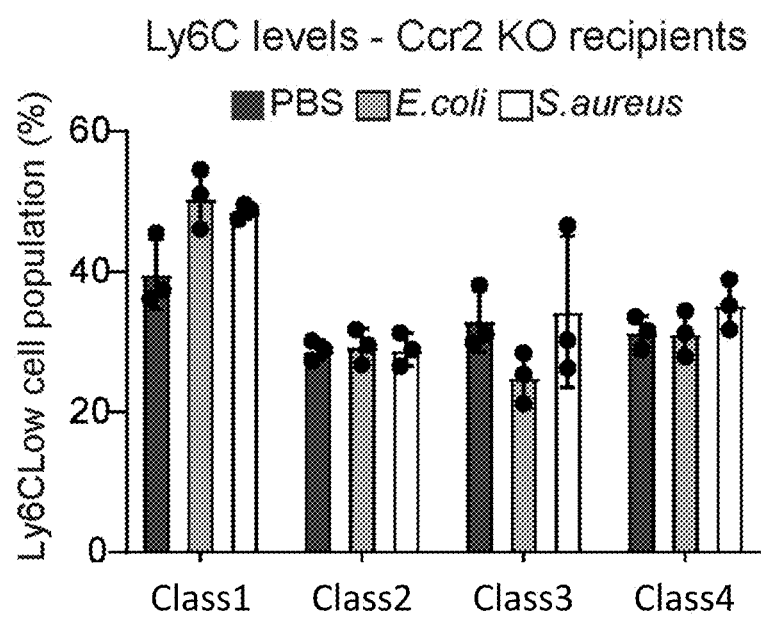

To test the stability of Ly6C levels in each monocytic class, Ly6C levels were examined 4 days post-transplantation of ER-Hoxb8 GMP clones intravenously injected into WT and Ccr2 KO mice. These mice were infected with E. coli or S. aureus interperitoneally 3 hours prior to analysis. The Ly6C levels of Class1-4 monocytes were shifted from Ly6C$^{Hi}$ to Ly6C$^{Low}$ when increasing numbers of bacteria were used in the infection (FIGS. 12G1, 12G1 and 11I). This indicates that Ly6C expression varies within each monocyte class further supporting the notion that these are orthogonal means of categorizing monocytes.

Example 7. Class-Specific Monocytes are Selected by Physiological Challenges

Figure 13A:
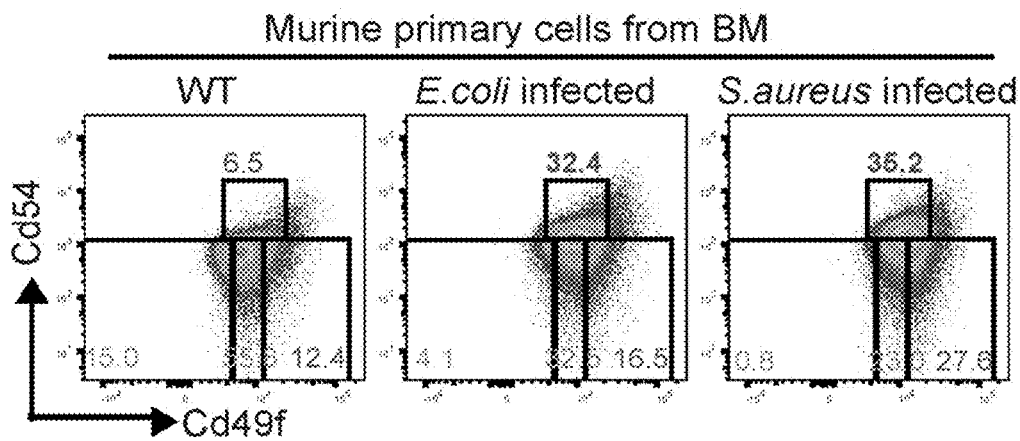
FIGS. 13A-L. Depicts class-specific monocytes selected by physiological challenges. (A) Representative FACS plots showing changes in the proportions of monocytic classes after 3 hours of bacterial infection (n=3 independent experiments, using 3 mice each experiment). (B) Experimental scheme of functional assays that evaluate selection vs induction of primary murine monocytes upon bacterial infection. The fluorophores labeled to each class of monocytes were used in different combinations as well. (C,D) Bar graphs showing percentage of primary monocyte subsets left in pooled samples after live E. coli and S. aureus infection, respectively, in vitro (n=3 independent experiments, using 3 mice each experiment). (E,F) Bar graphs showing number of ER-Hoxb8 monocytes found in bone marrow or peritoneal cavity of Ccr2 KO mice after heat-killed E. coli and S. aureus infection, respectively, in vivo (n=3 mice). (G,H) Bar graphs showing percentage of primary monocyte subsets left in pooled samples and F4/80 expression levels after 24 hrs of live bacterial infection into 5FU treated mice in vivo, respectively (n=3 independent experiments, using 3 mice each experiment). (I) Bar graphs showing phagocytosis efficiency in secondary exposure to live bacteria. (J) Survival curves of sub-lethally irradiated mice with injection of individual ER-Hoxb8 clones followed by infection with LPS (n=8 mice with 2 independent experiments). (K,L) Survival curves of lethally irradiated mice with injection of ER-Hoxb8 monocytic clones followed by live bacterial infection (n=10 mice with 2 independent experiments). See FIGS. 14A-K.
Figure 13B:
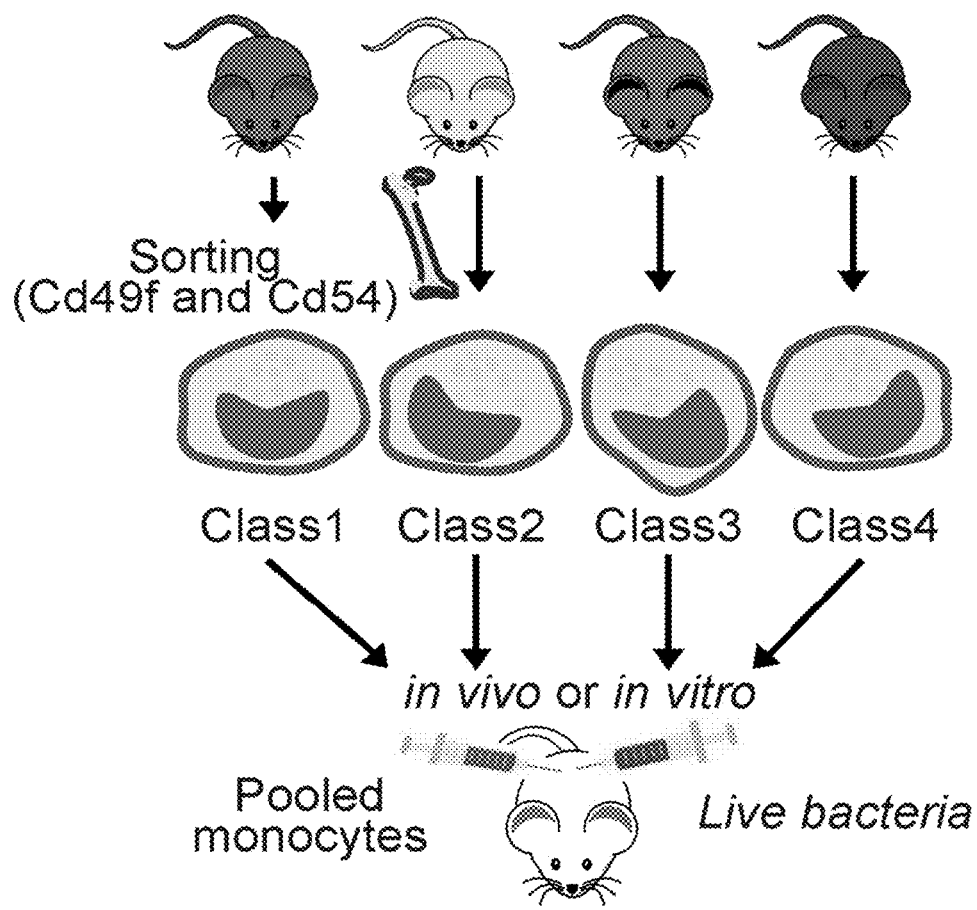
Figure 13C:
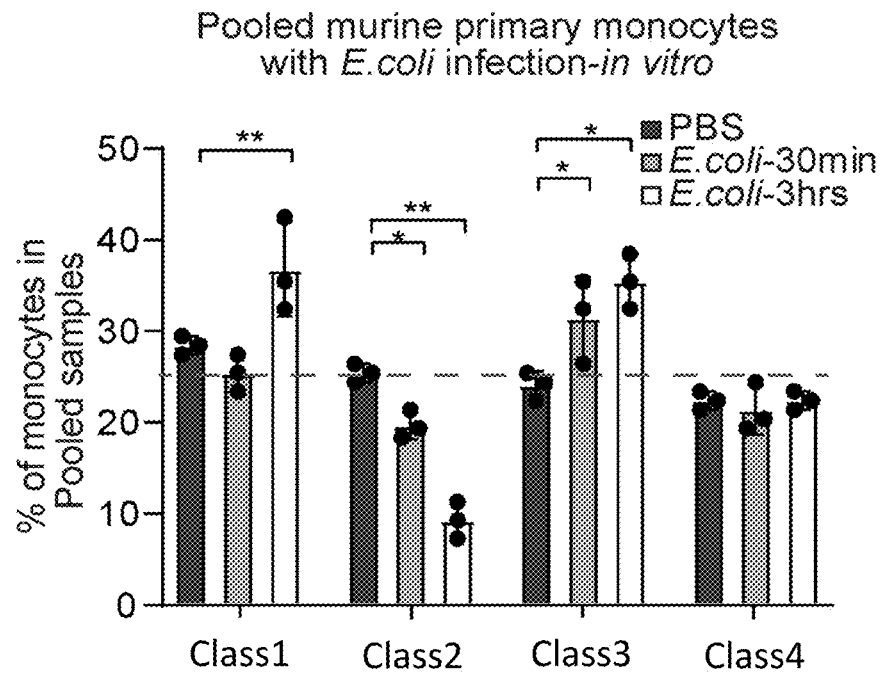
Figure 13D:
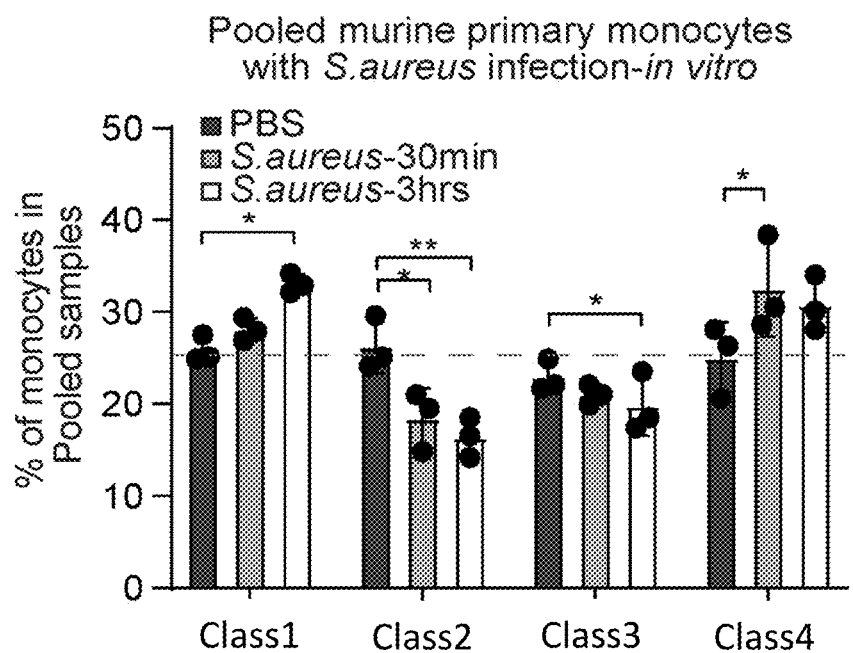
Figure 14A:
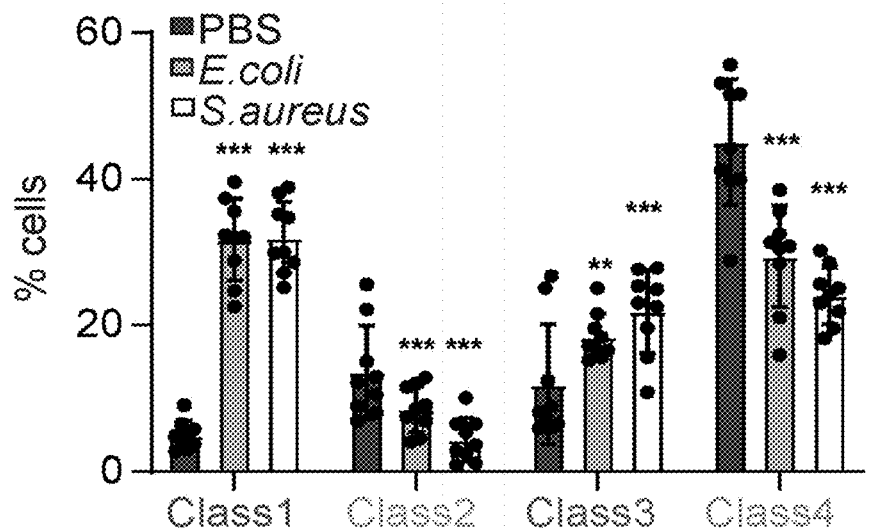
FIGS. 14A-K. Depicts each distinct phenotypes among each class upon bacterial infection, related to FIG. 13. (A) Bar graphs cell population before and after bacterial infection, related to FIG. 13A. (B) Representative FACS plots of FIG. 13C. The fluorophores labeled to each Class were used in different combinations as well. (C) Bar graph showing expression of F4/80 in each class upon bacterial infection in vitro (n=3 independent experiments). (D) Experimental scheme of 'selection' vs 'adaption' test using bacterial infection and pooled monocyte clones in the same mouse. (E) Bar graphs showing percentage of monocyte subsets left in pooled samples of lethally irradiated CCR2 KO mice after bacterial infection (n=3 independent experiments, in triplicate technical replicates). (F) Representative FACS plots showing gating strategy of FIG. 13E for analyzing sorted primary monocytes. The fluorophores labeled to each Class were used in different combinations as well. (G) Bar graphs comparing annexin expression of sorted primary mouse monocytes that were injected into the peritoneum of mice infected with bacteria. (n=2 independent experiments) (H) Experimental scheme of functional tests using bacterial infection trained mice to test memory existence. (I) Bar graphs showing expression of cytokines and F4/80 in both bacterial infection trained mice and WT mice, after infection with live E. coli or S. aureus. (n=3 independent experiments, using 3 mice each experiment). (J,K) Experimental scheme of survival assays, related to FIGS. 13J and 13K, 13L, respectively. *P<0.05, P<0.01, and *P<0.005.
Figure 14B:
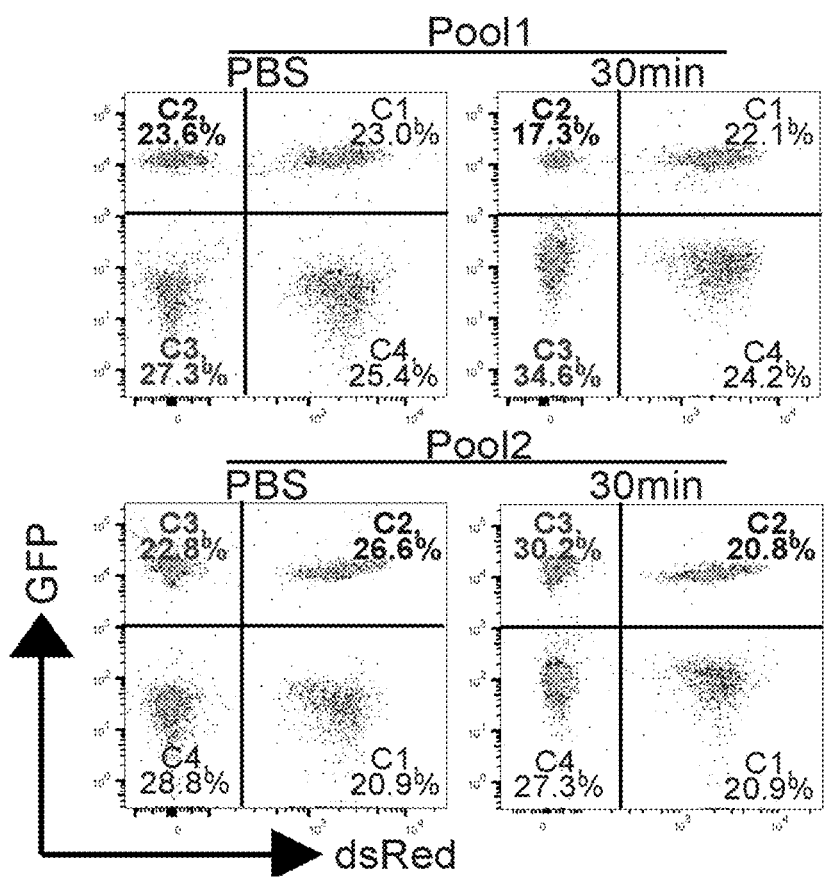
Figure 14C:
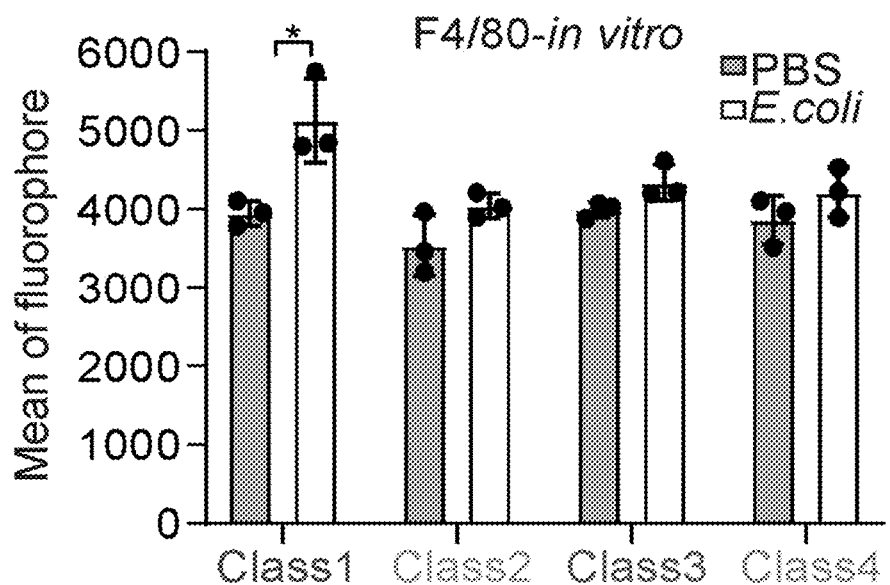

To further test whether cells alter their fate between classes or if classes are selected during infection, monocyte class populations were evaluated in the bone marrow before and after E. coli or S. aureus peritonitis. The proportion and absolute number of Class1 monocytes dramatically increased with septic challenge (FIGS. 13A and 14A), suggesting either Class1 monocytes proliferate in response to infection or monocytes switch identify to Class1. To test this question, each class of primary monocyte was sorted from a different fluorescently-labeled engineered mouse strain and incubated the sorted cells with live bacteria in vitro (FIG. 13B). After 3 hours of infection, proportions of monocytes in the pooled samples started to change (FIGS. 13C-13D and 14B). Whereas Class1/3 and Class1/4 monocytes increased upon *E. coli* and *S. aureus* exposure respectively, Class2 monocytes decreased (FIGS. 13C and 13D). In addition, the level of F4/80 in Class1 increased compared to other classes (FIG. 14C), suggesting a Class-specific response to bacteria and that the subset-specific responses do not converge.

Figure 13E:
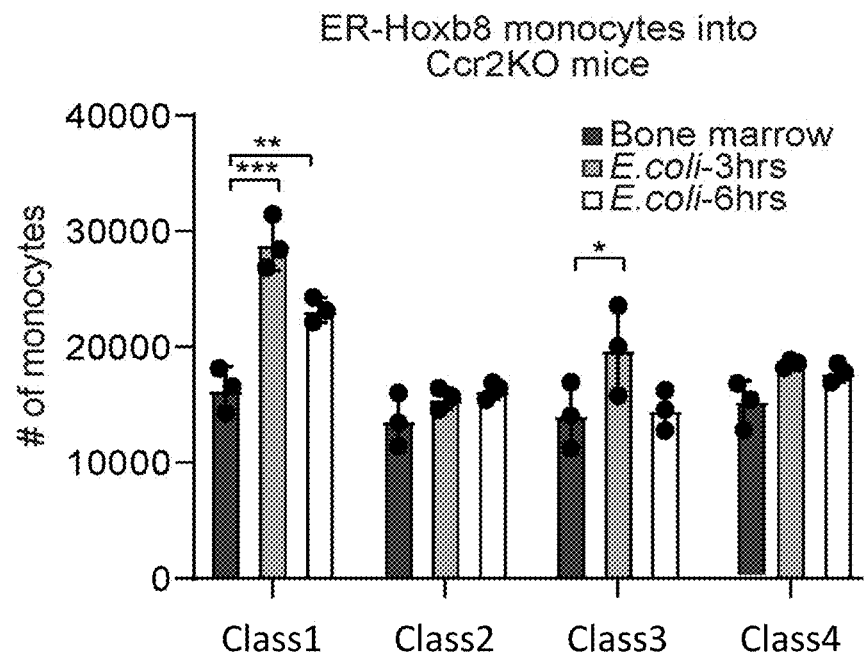
Figure 13F:
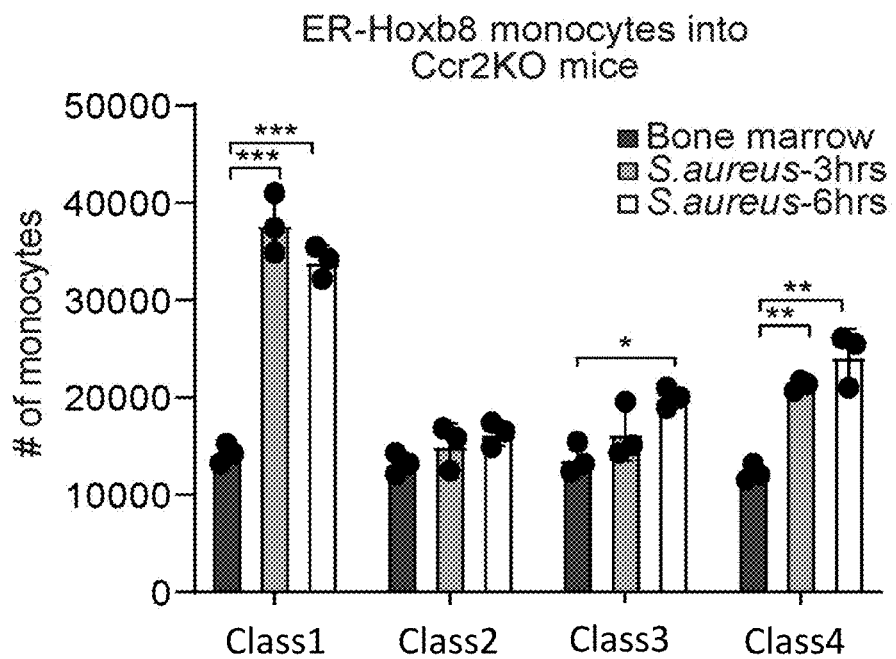
Figure 13G:
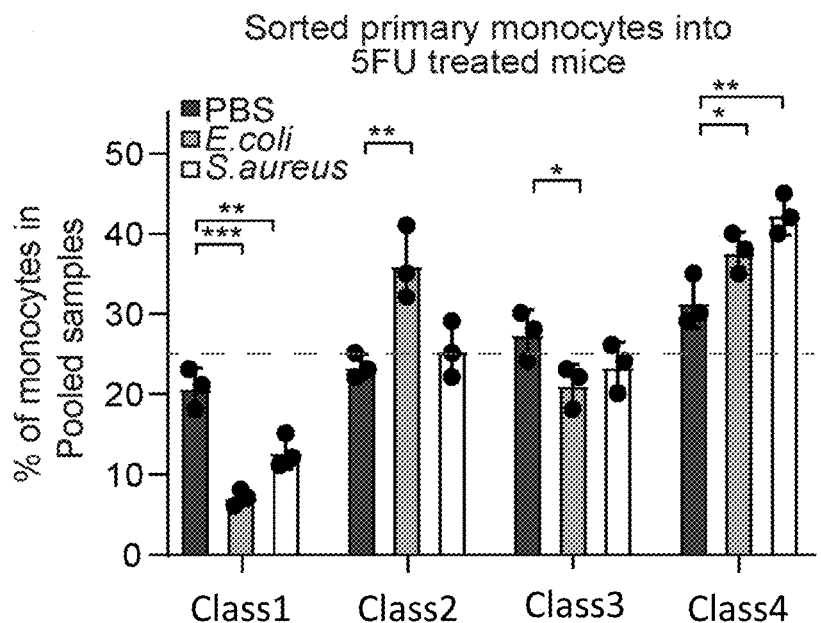
Figure 14D:
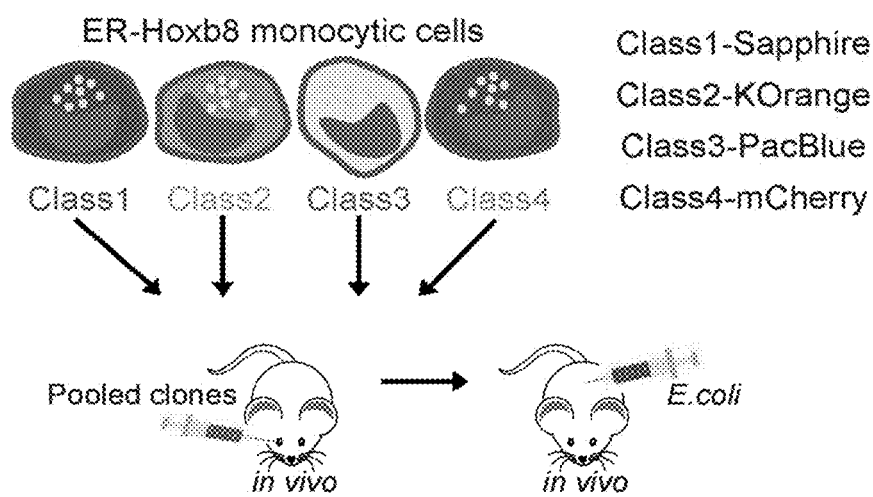
Figure 14E:
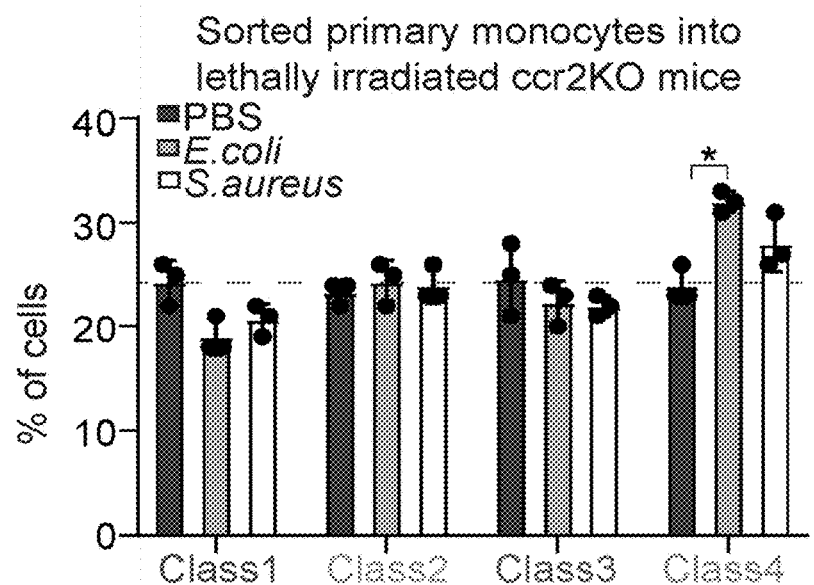
Figure 14F:
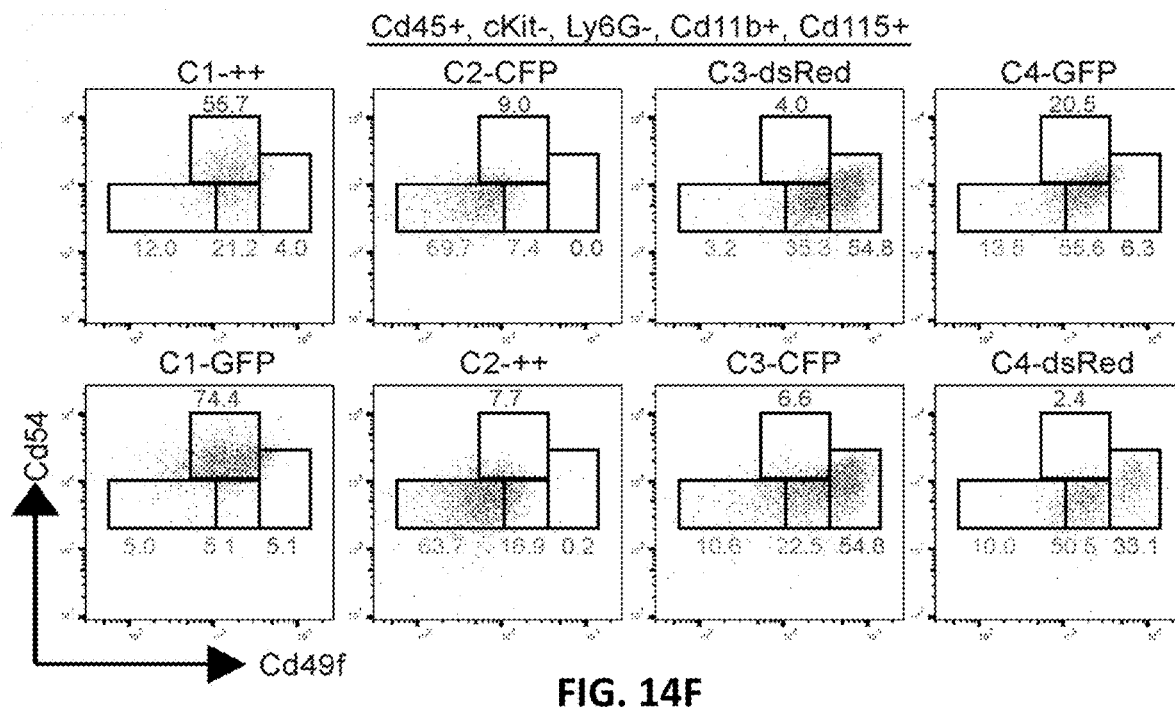

Next, equal cell numbers of all 4 classes of ER-Hoxb8 monocytic clones with each clone bearing a clone-specific, distinct fluorescent tag were injected into the same lethally irradiated Ccr2KO mice by intravenous injection. Thereafter, bacteria were injected into the peritoneal cavity of the same Ccr2 KO recipient mice (FIG. 14D). Interestingly, significant numbers of monocytes bearing the fluorescent tag of class 1 were then found in the peritoneal fluid after 3 hours of bacterial infection. By 6 hours, the number of Class1 monocytes decreased (FIGS. 13E and 13F). To validate these pooled monocyte behaviors in vivo, bacteria with equal numbers of sorted primary monocyte subsets were injected intraperitoneally into Ccr2KO or 5-FU treated recipient mice. Intraperitoneal cell numbers were quantified by fluorescent tag after 24 hours. Despite Class3 specializing in killing *E. coli* and Class4 specializing in killing *S. aureus* compared to other classes, proportions of Class1 monocytes were most affected in the peritoneal fluid (FIGS. 13G and 14E). Notably, the monocytes derived from distinct classes stayed in their original classes without changes in their class fate based on their surface markers (FIG. 14F). The cells were not capable of undergoing a state shift to acquire the Class1-like functional capability to accumulate in the peritoneal cavity with bacterial challenge. These aggregated data support a selection of Class1 cells over induction of Class1-like monocytes in vivo.

Figure 13H:
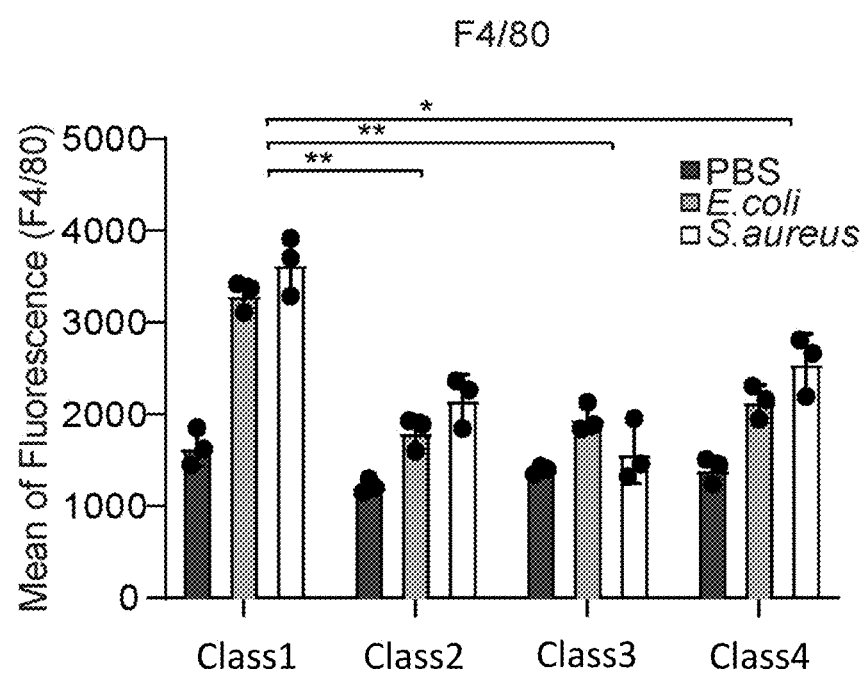
Figure 14G:
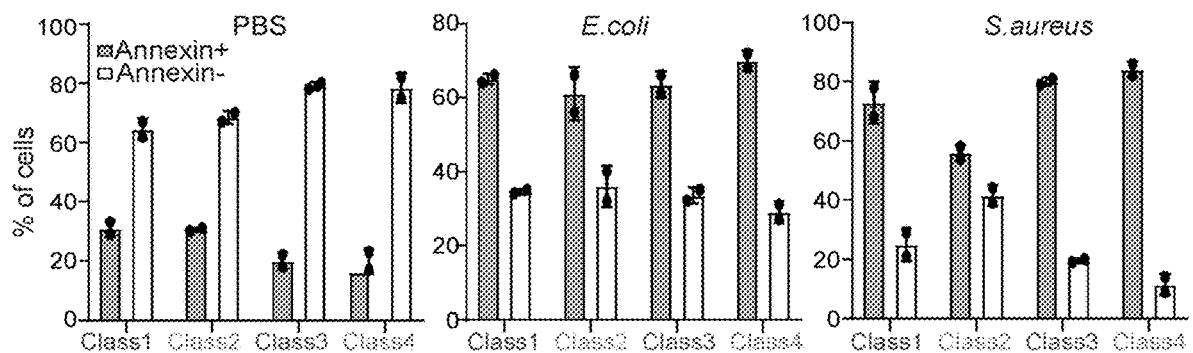

Furthermore, these data suggest that Class1 monocytes either undergo cell death or become activated, exiting the blood to tissues. Previous studies showed that even 5 minutes post LPS injection, active monocytes adhere to the wall of the peritoneum and eventually traffic to the lymph nodes (Cao et al., 2005; Randolph et al., 1999). Thus, F4/80 levels of the monocytes injected into bacterial infected mice were measured, and it was determined that F4/80 was significantly higher in Class1 following infectious challenge, though not at baseline, than other classes (FIG. 13H) and there was no induction of annexinV indicative of apoptosis (FIG. 14G). These data imply that Class1 monocytes were activated and thereby adhere to the peritoneal wall. The data conflict with those from the systemically administered Class1 ER-HoxB8 cells which preferentially entered the infected peritoneal cavity. However, both sets of data indicate that Class1 cells are distinctive in their response to the infectious challenge and differentially engage the peritoneum based on their vascular or peritoneal fluid location.

Example 8. Monocytes can be Trained by Bacterial Infection

Figure 13I:
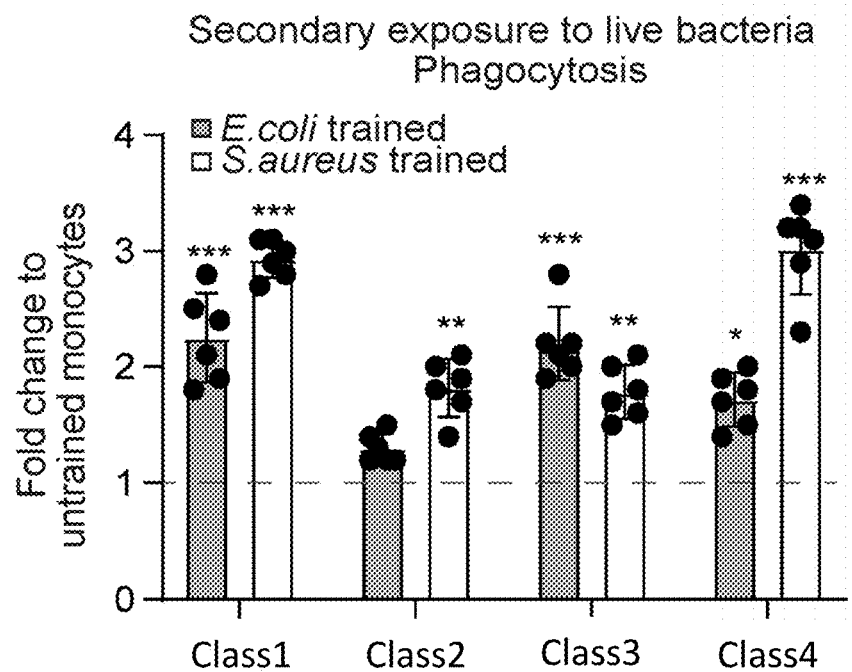
Figure 14H:
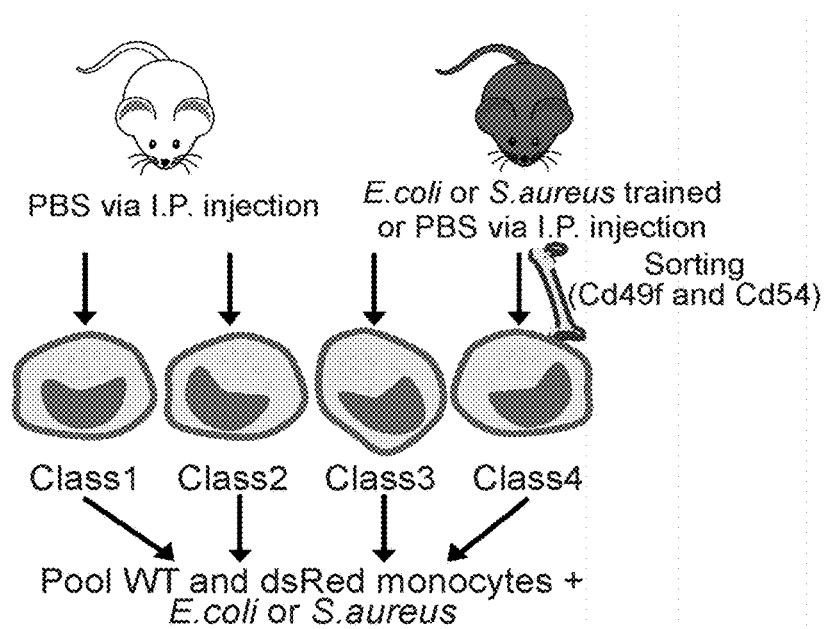
Figure 14I:
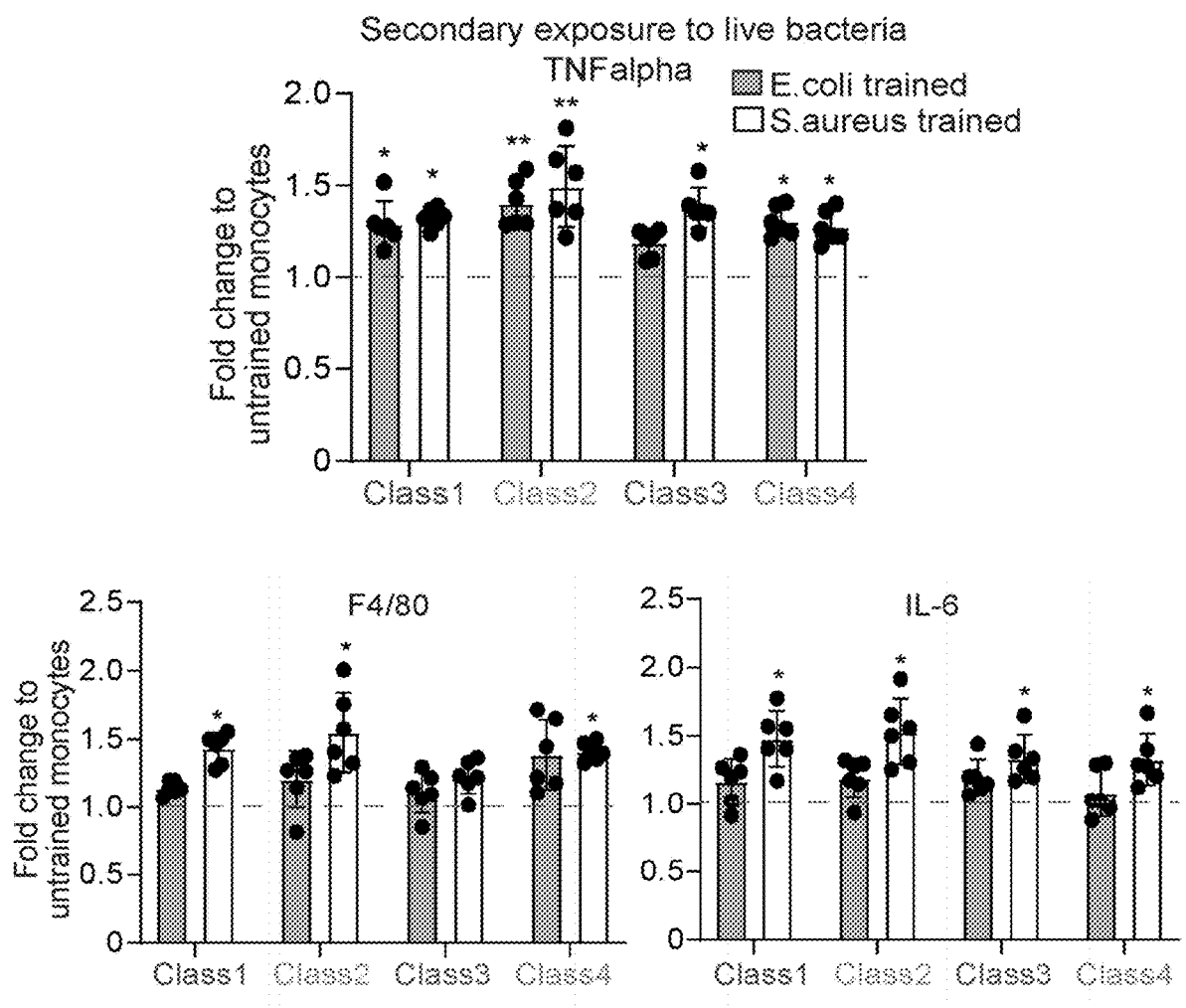

If there is a selection of particular monocyte subsets based on differential response to challenges, there might also be cellular memory. To test this, sorted monocytes of WT mice and mice that were previously exposed to bacteria were sorted (FIG. 14H) and exposed to bacteria in vitro. Evaluating monocytic functions (Mulder et al., 2019), it was determined that all classes have an enhanced phagocytosis upon secondary exposure to either *E. coli* or *S. aureus* (FIG. 13I). In addition, higher production of TNFalpha, F4/80, and IL-6 by 'trained' monocytes occurs across the different monocytic subsets (FIG. 14I) (de Laval et al., 2020; Mitroulis et al., 2018). These data are consistent with a 'reprogramming' effect or an epigenetic inscription of pathogen exposure proposed by others on either mature cells or primitive HSPC (Kleinnijenhuis et al., 2012; Netea et al., 2011; Saeed et al., 2014). Combined with selective increased representation of subsets of monocytes, the system may enable innate immune memory both by increasing the number of cells with specific functions and by potentiating responses within specific cell subsets.

Figure 13J:
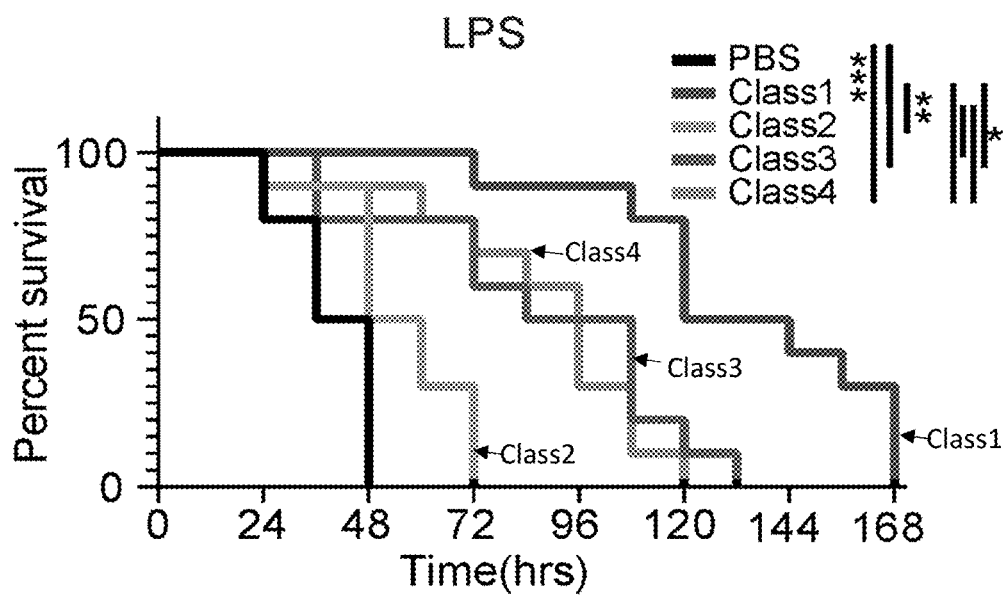
Figure 13K:
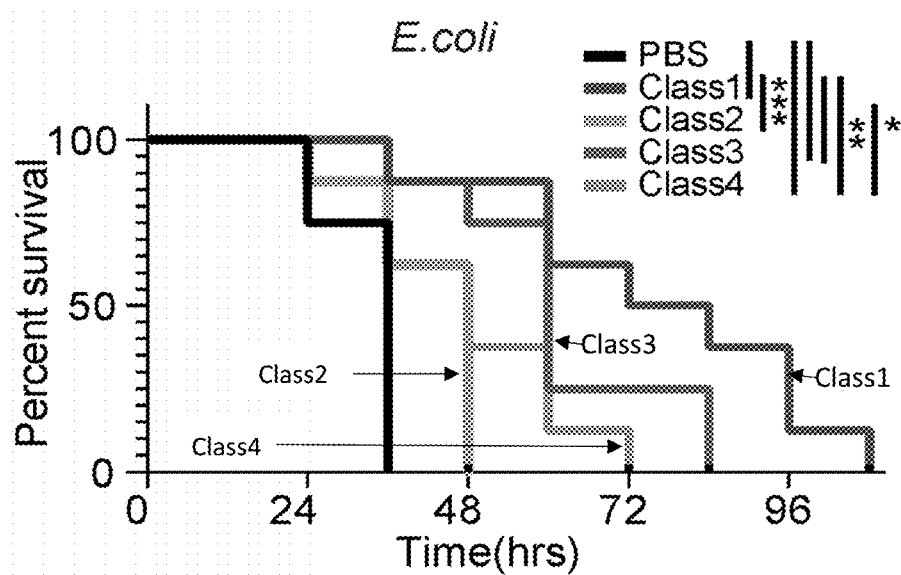
Figure 13L:
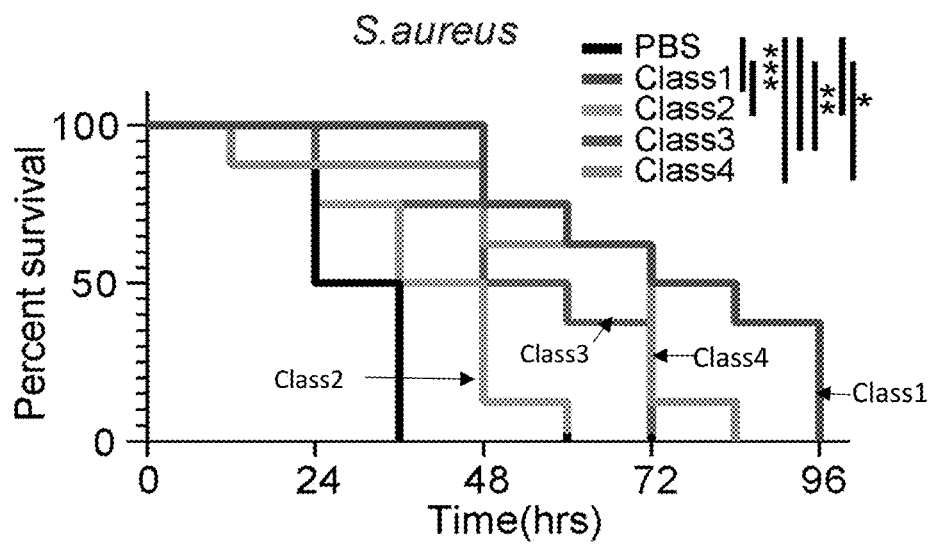
Figure 14J:
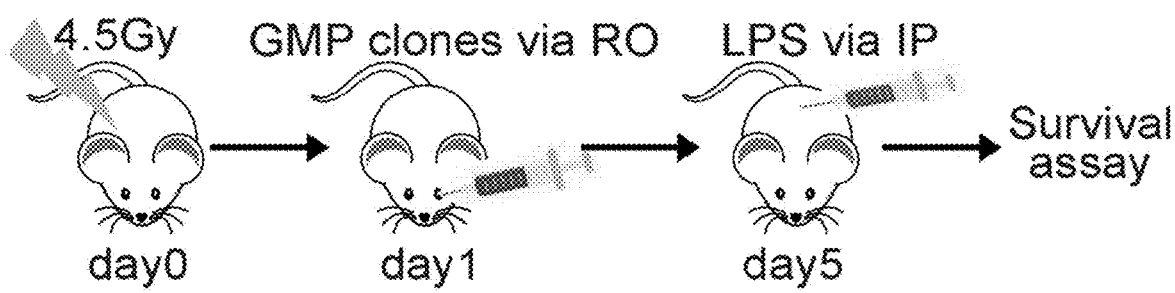
Figure 14K:
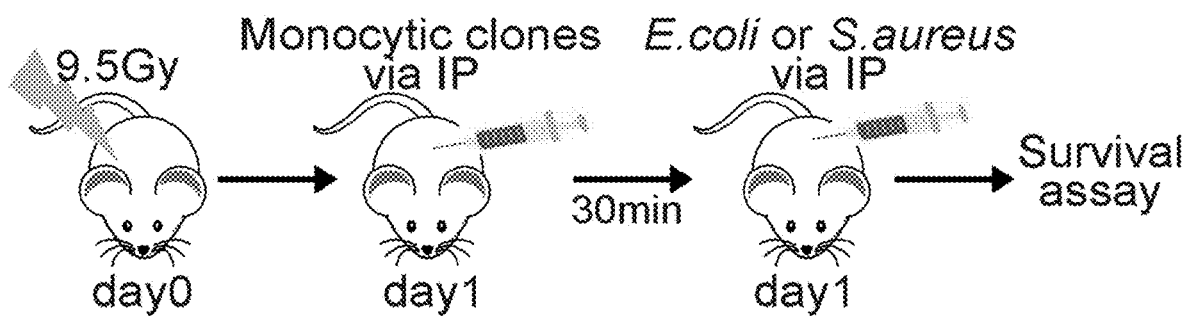

To determine if our findings had implications for clinical settings, mice were sub-lethally irradiated followed by injection of individual GMP clones intravenously. After allowing the clones to differentiate in vivo over four days, LPS was injected via intraperitoneal injection (FIG. 14J). Class1 GMP infusion significantly increased the survival rates compared to the infusion of other GMP classes (FIG. 13J). Next, mice were lethally irradiated followed by injection of monocytic clones and bacteria on the same day (FIG. 14K). Transfer of Class1 cells into recipient mice increased the survival rates most significantly (FIGS. 13K and 13L). These findings are consistent with class specific functions being maintained in stress and that Class1 monocytes provide preferential benefit under conditions resembling sepsis.

REFERENCES

All patents, patent applications and publications mentioned in this specification are herein incorporated by reference to the same extent as if each independent patent and publication was specifically and individually indicated to be incorporated by reference, including but not limited to the following references herein below.

1. Anders, S., McCarthy, D. J., Chen, Y., Okoniewski, M., Smyth, G. K., Huber, W., and Robinson, M. D. (2013). Count-based differential expression analysis of RNA sequencing data using R and Bioconductor. Nat Protoc 8, 1765-1786.
2. Anders, S., Pyl, P. T., and Huber, W. (2015). HTSeq—a Python framework to work with high-throughput sequencing data. Bioinformatics 31, 166-169.
3. Bailey, T. L., Boden, M., Buske, F. A., Frith, M., Grant, C. E., Clementi, L., Ren, J., Li, W. W., and Noble, W. S. (2009). MEME SUITE: tools for motif discovery and searching. Nucleic Acids Res 37, W202-208.
4. Bhang, H. E., Ruddy, D. A., Krishnamurthy Radhakrishna, V., Caushi, J. X., Zhao, R., Hims, M. M., Singh, A. P., Kao, I., Rakiec, D., Shaw, P., et al. (2015). Studying clonal dynamics in response to cancer therapy using high-complexity barcoding. Nat Med 21, 440-448.
5. Boyette, L. B., Macedo, C., Hadi, K., Elinoff, B. D., Walters, J. T., Ramaswami, B., Chalasani, G., Taboas, J. M., Lakkis, F. G., and Metes, D. M. (2017). Phenotype, function, and differentiation potential of human monocyte subsets. PLoS One 12, e0176460.
6. Breslin, W. L., Strohacker, K., Carpenter, K. C., Haviland, D. L., and McFarlin, B. K. (2013). Mouse blood monocytes: standardizing their identification and analysis using CD115. J Immunol Methods 390, 1-8.
7. Buenrostro, J. D., Corces, M. R., Lareau, C. A., Wu, B., Schep, A. N., Aryee, M. J., Majeti, R., Chang, H. Y., and Greenleaf, W. J. (2018). Integrated Single-Cell Analysis Maps the Continuous Regulatory Landscape of Human Hematopoietic Differentiation. Cell 173, 1535-1548 e1516.

8. Buenrostro, J. D., Wu, B., Chang, H. Y., and Greenleaf, W. J. (2015). ATAC-seq: A Method for Assaying Chromatin Accessibility Genome-Wide. Curr Protoc Mol Biol 109, 21 29 21-21 29 29.
9. Cao, C., Lawrence, D. A., Strickland, D. K., and Zhang, L. (2005). A specific role of integrin Mac-1 in accelerated macrophage efflux to the lymphatics. Blood 106, 3234-3241.
10. Chen, E. Y., Tan, C. M., Kou, Y., Duan, Q., Wang, Z., Meirelles, G. V., Clark, N. R., and Ma'ayan, A. (2013). Enrichr: interactive and collaborative HTML5 gene list enrichment analysis tool. BMC Bioinformatics 14, 128.
11. Cros, J., Cagnard, N., Woollard, K., Patey, N., Zhang, S. Y., Senechal, B., Puel, A., Biswas, S. K., Moshous, D., Picard, C., et al. (2010). Human CD14dim monocytes patrol and sense nucleic acids and viruses via TLR7 and TLR8 receptors. Immunity 33, 375-386.
12. de Laval, B., Maurizio, J., Kandalla, P. K., Brisou, G., Simonnet, L., Huber, C., Gimenez, G., Matcovitch-Natan, O., Reinhardt, S., David, E., et al. (2020). C/EBPbeta-Dependent Epigenetic Memory Induces Trained Immunity in Hematopoietic Stem Cells. Cell Stem Cell 26, 657-674 e658.
13. Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.
14. Drevets, D. A., Canono, B. P., and Campbell, P. A. (2015). Measurement of bacterial ingestion and killing by macrophages. Curr Protoc Immunol 109, 14 16 11-14 16 17.
15. Francke, A., Herold, J., Weinert, S., Strasser, R. H., and Braun-Dullaeus, R. C. (2011). Generation of mature murine monocytes from heterogeneous bone marrow and description of their properties. J Histochem Cytochem 59, 813-825.
16. Frankenberg, T., Kirschnek, S., Hacker, H., and Hacker, G. (2008). Phagocytosis-induced apoptosis of macrophages is linked to uptake, killing and degradation of bacteria. Eur J Immunol 38, 204-215.
17. Geissmann, F., Manz, M. G., Jung, S., Sieweke, M. H., Merad, M., and Ley, K. (2010). Development of monocytes, macrophages, and dendritic cells. Science 327, 656-661.
18. Ghisletti, S., Barozzi, I., Mietton, F., Polletti, S., De Santa, F., Venturini, E., Gregory, L., Lonie, L., Chew, A., Wei, C. L., et al. (2010). Identification and characterization of enhancers controlling the inflammatory gene expression program in macrophages. Immunity 32, 317-328.
19. Gordon, S., and Taylor, P. R. (2005). Monocyte and macrophage heterogeneity. Nat Rev Immunol 5, 953-964.
20. Gu, Z., Eils, R., and Schlesner, M. (2016). Complex heatmaps reveal patterns and correlations in multidimensional genomic data. Bioinformatics 32, 2847-2849.
21. Hanna, R. N., Carlin, L. M., Hubbeling, H. G., Nackiewicz, D., Green, A. M., Punt, J. A., Geissmann, F., and Hedrick, C. C. (2011). The transcription factor NR4A1 (Nur77) controls bone marrow differentiation and the survival of Ly6C-monocytes. Nat Immunol 12, 778-785.
22. Heinz, S., Benner, C., Spann, N., Bertolino, E., Lin, Y. C., Laslo, P., Cheng, J. X., Murre, C., Singh, H., and Glass, C. K. (2010). Simple combinations of lineage-determining transcription factors prime cis-regulatory elements required for macrophage and B cell identities. Mol Cell 38, 576-589.
23. Huang da, W., Sherman, B. T., and Lempicki, R. A. (2009). Systematic and integrative analysis of large gene lists using DAVID bioinformatics resources. Nat Protoc 4, 44-57.
24. Italiani, P., and Boraschi, D. (2014). From Monocytes to M1/M2 Macrophages: Phenotypical vs. Functional Differentiation. Front Immunol 5, 514.
25. Jakubzick, C. V., Randolph, G. J., and Henson, P. M. (2017). Monocyte differentiation and antigen-presenting functions. Nat Rev Immunol 17, 349-362.
26. Kapellos, T. S., Bonaguro, L., Gemund, I., Reusch, N., Saglam, A., Hinkley, E. R., and Schultze, J. L. (2019). Human Monocyte Subsets and Phenotypes in Major Chronic Inflammatory Diseases. Front Immunol 10, 2035.
27. Kleinnijenhuis, J., Quintin, J., Preijers, F., Joosten, L. A., Ifrim, D. C., Saeed, S., Jacobs, C., van Loenhout, J., de Jong, D., Stunnenberg, H. G., et al. (2012). Bacille Calmette-Guerin induces NOD2-dependent nonspecific protection from reinfection via epigenetic reprogramming of monocytes. Proc Natl Acad Sci USA 109, 17537-17542.
28. Koressaar, T., and Remm, M. (2007). Enhancements and modifications of primer design program Primer3. Bioinformatics 23, 1289-1291.
29. Li, H., and Durbin, R. (2009). Fast and accurate short read alignment with Burrows-Wheeler transform. Bioinformatics 25, 1754-1760.
30. Medzhitov, R., and Janeway, C., Jr. (2000). Innate immunity. N Engl J Med 343, 338-344.
31. Menezes, S., Melandri, D., Anselmi, G., Perchet, T., Loschko, J., Dubrot, J., Patel, R., Gautier, E. L., Hugues, S., Longhi, M. P., et al. (2016). The Heterogeneity of Ly6C(hi) Monocytes Controls Their Differentiation into iNOS(+) Macrophages or Monocyte-Derived Dendritic Cells. Immunity 45, 1205-1218.
32. Mercier, F. E., Sykes, D. B., and Scadden, D. T. (2016). Single Targeted Exon Mutation Creates a True Congenic Mouse for Competitive Hematopoietic Stem Cell Transplantation: The C57BL/6-CD45.1(STEM) Mouse. Stem Cell Reports 6, 985-992.
33. Mildner, A., Schonheit, J., Giladi, A., David, E., Lara-Astiaso, D., Lorenzo-Vivas, E., Paul, F., Chappell-Maor, L., Priller, J., Leutz, A., et al. (2017). Genomic Characterization of Murine Monocytes Reveals C/EBPbeta Transcription Factor Dependence of Ly6C(-) Cells. Immunity 46, 849-862 e847.
34. Mitroulis, I., Ruppova, K., Wang, B., Chen, L. S., Grzybek, M., Grinenko, T., Eugster, A., Troullinaki, M., Palladini, A., Kourtzelis, I., et al. (2018). Modulation of Myelopoiesis Progenitors Is an Integral Component of Trained Immunity. Cell 172, 147-161 e12.
35. Mulder, W. J. M., Ochando, J., Joosten, L. A. B., Fayad, Z. A., and Netea, M. G. (2019). Therapeutic targeting of trained immunity. Nat Rev Drug Discov 18, 553-566.
36. Narasimhan, P. B., Marcovecchio, P., Hamers, A. A. J., and Hedrick, C. C. (2019). Nonclassical Monocytes in Health and Disease. Annu Rev Immunol 37, 439-456.
37. Netea, M. G., Quintin, J., and van der Meer, J. W. (2011). Trained immunity: a memory for innate host defense. Cell Host Microbe 9, 355-361.
38. Olingy, C. E., Dinh, H. Q., and Hedrick, C. C. (2019). Monocyte heterogeneity and functions in cancer. J Leukoc Biol 106, 309-322.
39. Passlick, B., Flieger, D., and Ziegler-Heitbrock, H. W. (1989). Identification and characterization of a novel monocyte subpopulation in human peripheral blood. Blood 74, 2527-2534.

40. Patel, A. A., Zhang, Y., Fullerton, J. N., Boelen, L., Rongvaux, A., Maini, A. A., Bigley, V., Flavell, R. A., Gilroy, D. W., Asquith, B., et al. (2017). The fate and lifespan of human monocyte subsets in steady state and systemic inflammation. J Exp Med 214, 1913-1923.
41. Paul, F., Arkin, Y., Giladi, A., Jaitin, D. A., Kenigsberg, E., Keren-Shaul, H., Winter, D., Lara-Astiaso, D., Gury, M., Weiner, A., et al. (2015). Transcriptional Heterogeneity and Lineage Commitment in Myeloid Progenitors. Cell 163, 1663-1677.
42. Pham, T. H., Minderjahn, J., Schmidl, C., Hoffmeister, H., Schmidhofer, S., Chen, W., Langst, G., Benner, C., and Rehli, M. (2013). Mechanisms of in vivo binding site selection of the hematopoietic master transcription factor PU.1. Nucleic Acids Res 41, 6391-6402.
43. Quinlan, A. R., and Hall, I. M. (2010). BEDTools: a flexible suite of utilities for comparing genomic features. Bioinformatics 26, 841-842.
44. Randolph, G. J., Inaba, K., Robbiani, D. F., Steinman, R. M., and Muller, W. A. (1999). Differentiation of phagocytic monocytes into lymph node dendritic cells in vivo. Immunity 11, 753-761.
45. Robinson, M. D., McCarthy, D. J., and Smyth, G. K. (2010). edgeR: a Bioconductor package for differential expression analysis of digital gene expression data. Bioinformatics 26, 139-140.
46. Saeed, S., Quintin, J., Kerstens, H. H., Rao, N. A., Aghajanirefah, A., Matarese, F., Cheng, S. C., Ratter, J., Berentsen, K., van der Ent, M. A., et al. (2014). Epigenetic programming of monocyte-to-macrophage differentiation and trained innate immunity. Science 345, 1251086.
47. Schauer, D., Starlinger, P., Zajc, P., Alidzanovic, L., Maier, T., Buchberger, E., Pop, L., Gruenberger, B., Gruenberger, T., and Brostj an, C. (2014). Monocytes with angiogenic potential are selectively induced by liver resection and accumulate near the site of liver regeneration. BMC Immunol 15, 50
48. Shi, C., and Pamer, E. G. (2011). Monocyte recruitment during infection and inflammation. Nat Rev Immunol 11, 762-774.
49. Swirski, F. K., Nahrendorf, M., Etzrodt, M., Wildgruber, M., Cortez-Retamozo, V., Panizzi, P., Figueiredo, J. L., Kohler, R. H., Chudnovskiy, A., Waterman, P., et al. (2009). Identification of splenic reservoir monocytes and their deployment to inflammatory sites. Science 325, 612-616.
50. Sykes, D. B., Kfoury, Y. S., Mercier, F. E., Wawer, M. J., Law, J. M., Haynes, M. K., Lewis, T. A., Schajnovitz, A., Jain, E., Lee, D., et al. (2016). Inhibition of Dihydroorotate Dehydrogenase Overcomes Differentiation Blockade in Acute Myeloid Leukemia. Cell 167, 171-186 e115.
51. Thomas, G. D., Hamers, A. A. J., Nakao, C., Marcovecchio, P., Taylor, A. M., McSkimming, C., Nguyen, A. T., McNamara, C. A., and Hedrick, C. C. (2017). Human Blood Monocyte Subsets: A New Gating Strategy Defined Using Cell Surface Markers Identified by Mass Cytometry. Arterioscler Thromb Vasc Biol 37, 1548-1558.
52. Varol, C., Landsman, L., Fogg, D. K., Greenshtein, L., Gildor, B., Margalit, R., Kalchenko, V., Geissmann, F., and Jung, S. (2007). Monocytes give rise to mucosal, but not splenic, conventional dendritic cells. J Exp Med 204, 171-180.
53. Villani, A. C., Satij a, R., Reynolds, G., Sarkizova, S., Shekhar, K., Fletcher, J., Griesbeck, M., Butler, A., Zheng, S., Lazo, S., et al. (2017). Single-cell RNA-seq reveals new types of human blood dendritic cells, monocytes, and progenitors. Science 356.
54. Wang, G. G., Calvo, K. R., Pasillas, M. P., Sykes, D. B., Hacker, H., and Kamps, M. P. (2006). Quantitative production of macrophages or neutrophils ex vivo using conditional Hoxb8. Nat Methods 3, 287-293.
55. Xie, Z., Bailey, A., Kuleshov, M. V., Clarke, D. J. B., Evangelista, J. E., Jenkins, S. L., Lachmann, A., Wojciechowicz, M. L., Kropiwnicki, E., Jagodnik, K. M., et al. (2021). Gene Set Knowledge Discovery with Enrichr. Curr Protoc 1, e90.
56. Yanez, A., Coetzee, S. G., Olsson, A., Muench, D. E., Berman, B. P., Hazelett, D. J., Salomonis, N., Grimes, H. L., and Goodridge, H. S. (2017). Granulocyte-Monocyte Progenitors and Monocyte-Dendritic Cell Progenitors Independently Produce Functionally Distinct Monocytes. Immunity 47, 890-902 e894.
57. Yang, J., Zhang, L., Yu, C., Yang, X. F., and Wang, H. (2014). Monocyte and macrophage differentiation: circulation inflammatory monocyte as biomarker for inflammatory diseases. Biomark Res 2, 1.
58. Yona, S., Kim, K. W., Wolf, Y., Mildner, A., Varol, D., Breker, M., Strauss-Ayali, D., Viukov, S., Guilliams, M., Misharin, A., et al. (2013). Fate mapping reveals origins and dynamics of monocytes and tissue macrophages under homeostasis. Immunity 38, 79-91.

The invention claimed is:

1. A method of treating a microbial infection in a tissue of a subject, the method comprising administering to the subject a composition comprising isolated monocyte cells that express Cd49f, Cd54, and Cd11b; and express an increased level of Bcl6, Tlr4, Tlr9, Notch2 and Il1r1, and secrete an increased level of cytokines IL6 and TNF alpha compared to classical and non-classical monocytes, thereby treating the microbial infection in the tissue of the subject.

2. The method of claim 1, wherein the microbial infection is a gram negative bacterial infection or a gram positive bacterial infection.

3. The method of claim 2, wherein the gram negative bacterial infection is an *E. coli* infection, and the gram positive bacterial infection is an *S. aureus* infection.

4. The method of claim 1, wherein the cells comprise exogenous nucleic acid sequences recombined into their genomic DNA.

5. The method of claim 4, wherein the exogenous nucleic acid sequences encode ER-Hoxb8.

6. The method of claim 1, wherein the cells comprise transiently expressed exogenous nucleic acid sequences.

* * * * *

UNITED STATES PATENT AND TRADEMARK OFFICE
CERTIFICATE OF CORRECTION

| | | |
|---|---|---|
| PATENT NO. | : 12,193,996 B2 | Page 1 of 1 |
| APPLICATION NO. | : 17/525673 | |
| DATED | : January 14, 2025 | |
| INVENTOR(S) | : Catherine Rhee and David T. Scadden | |

It is certified that error appears in the above-identified patent and that said Letters Patent is hereby corrected as shown below:

In the Claims

In Column 55, Line 55, Claim 1, delete "Illr1," and insert -- II1r1, --

Signed and Sealed this
Twenty-seventh Day of May, 2025

Coke Morgan Stewart
*Acting Director of the United States Patent and Trademark Office*

SEQUENCE LISTING

<160> NUMBER OF SEQ ID NOS: 32

<210> SEQ ID NO 1
<211> LENGTH: 1839
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1774)..(1774)
<223> OTHER INFORMATION: n is a, c, g, or t
<220> FEATURE:
<221> NAME/KEY: misc_feature
<222> LOCATION: (1825)..(1826)
<223> OTHER INFORMATION: n is a, c, g, or t

<400> SEQUENCE: 1

```
gctctcttcc tcatccgccc cgtctctccc ccttgaacct cctcgttcga ccccgcctcg    60
atcctcccct tatccagccc tcactccttc tctaggcgcc ggaattcgcc accatgggat   120
acccatacga tgttccggat tacgctacgc gttctgctgg agacatgaga gctgccaacc   180
tttggccaag cccgctcatg atcaaacgct ctaagaagaa cagcctggcc ttgtccctga   240
cggccgacca gatggtcagt gccttgttgg atgctgagcc ccccatactc tattccgagt   300
atgatcctac cagacccttc agtgaagctt cgatgatggg cttactgacc aacctggcag   360
acagggagct ggttcacatg atcaactggg cgaagagggt gccaggcttt gtggatttga   420
ccctccatga tcaggtccac cttctagaat gtgcctggct agagatcctg atgattggtc   480
tcgtctggcg ctccatggag cacccagtga agctactgtt tgctcctaac ttgctcttgg   540
acaggaacca gggaaaatgt gtagagggca tggtggagat cttcgacatg ctgctggcta   600
catcatctcg gttccgcatg atgaatctgc agggagagga gtttgtgtgc ctcaaatcta   660
ttatttttgct taattctgga gtgtacacat ttctgtccag caccctgaag tctctggaag   720
agaaggacca tatccaccga gtcctggaca agatcacaga cactttgatc cacctgatgg   780
ccaaggcagg cctgaccctg cagcagcagc accagcggct ggcccagctc ctcctcatcc   840
tctcccacat caggcacatg agtaacaaag gcatggagca tctgtacagc atgaagtgca   900
agaacgtggt gcccctctat gacctgctgc tggagatgct ggacgcccac cgcctacatg   960
cgcccactag ccgtggaggg gcatccgtgg aggagacgga ccaaagccac ttggccactg  1020
cgggctctac ttcatcgcat tccttgcaaa agtattacat cacggggggag gcagagggtt  1080
tccctgccac agtcacgcgt ggaagctctt atttcgtcaa ctcactgttc tccaaataca  1140
aaaccgggga gtccctgcgc cccaattatt atgactgcgg cttcgcccag gacctgggcg  1200
gccgacccac cgtggtgtac ggtcccagca gcggcggcag cttccagcac ccttcgcaaa  1260
tccaggagtt ctaccacggg ccatcgtcgc tgtccacagc tccctaccag cagaacccgt  1320
gcgccgtggc gtgccacggc gaccccggca acttctacgg ctacgaccct ctgcagcgcc  1380
agagcctgtt cggtgcgcag gatccagacc tggtgcagta cgcagactgc aagctcgcgg  1440
cagccagcgg cctgggcgag gaggccgagg ggtctgagca gagcccgtcg cccacacagc  1500
tctttccctg gatgcgccct caagccgccg gacgcaggcg aggccgccag acctacagtc  1560
gctaccagac cctggagctg gagaaggagt tcctatttaa tccctatctg aatcgcaagc  1620
ggaggatcga ggtatcgcac gcgctgggac tgacagagac acaggtcaaa atctggttcc  1680
agaatcggag aatgaagtgg aaaaaggaga acaacaaaga caagtttccc agcagtaaat  1740
gcgagcagga ggagctggag aaagagaagc tggngcgggc accagagacc gccgagcagg  1800
gcgatgcgca gaagggtgac aagannngtag taactcgag                        1839
```

<210> SEQ ID NO 2
<211> LENGTH: 1836
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1771)..(1771)
<223> OTHER INFORMATION: n is a, c, g, or t
<220> FEATURE:
<221> NAME/KEY: misc_feature
<222> LOCATION: (1822)..(1823)

<223> OTHER INFORMATION: n is a, c, g, or t

<400> SEQUENCE: 2

```
gctctcttcc tcatccgccc cgtctctccc ccttgaacct cctcgttcga ccccgcctcg      60
atcctcccctt tatccagccc tcactccttc tctaggcgcc ggaattcgcc accatggact    120
acaaggacga cgatgacaaa ggaacgcgtt ctgctggaga catgagagct gccaaccttt    180
ggccaagccc gctcatgatc aaacgctcta agaagaacag cctggccttg tccctgacgg    240
ccgaccagat ggtcagtgcc ttgttggatg ctgagccccc catactctat tccgagtatg    300
atcctaccag acccttcagt gaagcttcga tgatgggctt actgaccaac ctggcagaca    360
gggagctggt tcacatgatc aactgggcga agagggtgcc aggctttgtg gatttgaccc    420
tccatgatca ggtccacctt ctagaatgtg cctggctaga gatcctgatg attggtctcg    480
tctggcgctc catggagcac ccagtgaagc tactgtttgc tcctaacttg ctcttggaca    540
ggaaccaggg aaaatgtgta gagggcatgg tggagatctt cgacatgctg ctggctacat    600
catctcggtt ccgcatgatg aatctgcagg gagaggagtt tgtgtgcctc aaatctatta    660
ttttgcttaa ttctggagtg tacacatttc tgtccagcac cctgaagtct ctggaagaga    720
aggaccatat ccaccgagtc ctggacaaga tcacagacac tttgatccac ctgatggcca    780
aggcaggcct gaccctgcag cagcagcacc agcggctggc ccagctcctc ctcatcctct    840
cccacatcag gcacatgagt aacaaaggca tggagcatct gtacagcatg aagtgcaaga    900
acgtggtgcc cctctatgac ctgctgctgg agatgctgga cgcccaccgc tacatgcgc     960
ccactagccg tggaggggca tccgtggagg agacggacca aagccacttg gccactgcgg   1020
gctctacttc atcgcattcc ttgcaaaagt attacatcac gggggaggca gagggtttcc   1080
ctgccacagt cacgcgtgga agctcttatt tcgtcaactc actgttctcc aaatacaaaa   1140
ccggggagtc cctgcgcccc aattattatg actgcggctt cgcccaggac ctgggcggcc   1200
gacccaccgt ggtgtacggt cccagcagcg gcggcagctt ccagcaccct tcgcaaatcc   1260
aggagttcta ccacgggcca tcgtcgctgt ccacagctcc ctaccagcag aacccgtgcg   1320
ccgtggcgtg ccacggcgac cccggcaact tctacggcta cgaccctctg cagcgccaga   1380
gcctgttcgg tgcgcaggat ccagacctgg tgcagtacgc agactgcaag ctcgcggcag   1440
ccagcggcct gggcgaggag gccgaggggt ctgagcagag cccgtcgccc acacagctct   1500
ttcccctgga tgcgccctcaa gccgccggac gcaggcgagg ccgccagacc tacagtcgct   1560
accagaccct ggagctggag aaggagttcc tatttaatcc ctatctgaat cgcaagcgga   1620
ggatcgaggt atcgcacgcg ctgggactga cagagagaca ggtcaaaatc tggttccaga   1680
atcggagaat gaagtggaaa aaggagaaca caaagacaa gtttcccagc agtaaatgcg   1740
agcaggagga gctggagaaa gagaagctgg ngcgggcacc agagaccgcc gagcagggcg   1800
atgcgcagaa gggtgacaag anngtagtaa ctcgag                             1836
```

<210> SEQ ID NO 3
<211> LENGTH: 51
<212> TYPE: DNA
<213> ORGANISM: Artificial Sequence
<220> FEATURE:
<223> OTHER INFORMATION: HA tag

<400> SEQUENCE: 3

```
gaattcgcca ccatgggata cccatacgat gttccggatt acgctacgcg t             51
```

-continued

```
<210> SEQ ID NO 4
<211> LENGTH: 48
<212> TYPE: DNA
<213> ORGANISM: Artificial Sequence
<220> FEATURE:
<223> OTHER INFORMATION: Flag tag

<400> SEQUENCE: 4
gaattcgcca ccatggacta caaggacgac gatgacaaag gaacgcgt                    48

<210> SEQ ID NO 5
<211> LENGTH: 77
<212> TYPE: DNA
<213> ORGANISM: Artificial Sequence
<220> FEATURE:
<223> OTHER INFORMATION: Synthetic primer

<400> SEQUENCE: 5
ggaattcgcc accatgggat acccatacga tgttccggat tacgctacgc gtggaagctc       60
ttatttcgtc aactcac                                                      77

<210> SEQ ID NO 6
<211> LENGTH: 74
<212> TYPE: DNA
<213> ORGANISM: Artificial Sequence
<220> FEATURE:
<223> OTHER INFORMATION: Synthetic primer

<400> SEQUENCE: 6
ggaattcgcc accatggact acaaggacga cgatgacaaa ggaacgcgtg gaagctctta       60
tttcgtcaac tcac                                                         74

<210> SEQ ID NO 7
<211> LENGTH: 35
<212> TYPE: DNA
<213> ORGANISM: Artificial Sequence
<220> FEATURE:
<223> OTHER INFORMATION: Synthetic primer

<400> SEQUENCE: 7
ccgctcgagt tactacttct tgtcacccct ctgcg                                  35

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
gcaccatgtt agctgctctt c                                                 21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
tggactcatt ctccttgcac t                                                 21

<210> SEQ ID NO 10
<211> LENGTH: 21
<212> TYPE: DNA
```

```
<213> ORGANISM: Artificial Sequence
<220> FEATURE:
<223> OTHER INFORMATION: Synthetic primer

<400> SEQUENCE: 10
tggggtttgt tcttgtctt g                                             21

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
aaccaccacc caggaactat c                                            21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
cttcacggct tcagagatga c                                            21

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
ttgatctgaa cagggatcca g                                            21

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
acagtggcga atacaggtgt c                                            21

<210> SEQ ID NO 15
<211> LENGTH: 21
<212> TYPE: DNA
<213> ORGANISM: Artificial Sequence
<220> FEATURE:
<223> OTHER INFORMATION: Synthetic primer

<400> SEQUENCE: 15
gggttctcct tctgtgagga c                                            21

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
atcacccaaa gggccatata c                                            21
```

```
<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
attattccag cctgccttgt t                                                  21

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
gaaaggcatt tcgtgtacca g                                                  21

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
actcctcccg gttgtagatg t                                                  21

<210> SEQ ID NO 20
<211> LENGTH: 24
<212> TYPE: DNA
<213> ORGANISM: Artificial Sequence
<220> FEATURE:
<223> OTHER INFORMATION: Synthetic primer

<400> SEQUENCE: 20
cttggtagag gtgactgagg agtt                                               24

<210> SEQ ID NO 21
<211> LENGTH: 25
<212> TYPE: DNA
<213> ORGANISM: Artificial Sequence
<220> FEATURE:
<223> OTHER INFORMATION: Synthetic primer

<400> SEQUENCE: 21
gttgtagact gttaaggtcc tctgc                                              25

<210> SEQ ID NO 22
<211> LENGTH: 23
<212> TYPE: DNA
<213> ORGANISM: Artificial Sequence
<220> FEATURE:
<223> OTHER INFORMATION: Synthetic primer

<400> SEQUENCE: 22
ctgaattcaa atgaagccaa aac                                                23

<210> SEQ ID NO 23
<211> LENGTH: 23
<212> TYPE: DNA
<213> ORGANISM: Artificial Sequence
<220> FEATURE:
```

<223> OTHER INFORMATION: Synthetic primer

<400> SEQUENCE: 23
tccttctcgg gtaccaaatt tat                                          23

<210> SEQ ID NO 24
<211> LENGTH: 21
<212> TYPE: DNA
<213> ORGANISM: Artificial Sequence
<220> FEATURE:
<223> OTHER INFORMATION: Synthetic primer

<400> SEQUENCE: 24
aaattcaacg gcacagtcaa g                                            21

<210> SEQ ID NO 25
<211> LENGTH: 21
<212> TYPE: DNA
<213> ORGANISM: Artificial Sequence
<220> FEATURE:
<223> OTHER INFORMATION: Synthetic primer

<400> SEQUENCE: 25
caccccattt gatgttagtg g                                            21

<210> SEQ ID NO 26
<211> LENGTH: 237
<212> TYPE: PRT
<213> ORGANISM: Homo sapiens

<400> SEQUENCE: 26

```
Thr Ala Asp Gln Met Val Ser Ala Leu Leu Asp Ala Glu Pro Pro Ile
1               5                   10                  15

Leu Tyr Ser Glu Tyr Asp Pro Thr Arg Pro Phe Ser Glu Ala Ser Met
            20                  25                  30

Met Gly Leu Leu Thr Asn Leu Ala Asp Arg Glu Leu Val His Met Ile
        35                  40                  45

Asn Trp Ala Lys Arg Val Pro Gly Phe Val Asp Leu Thr Leu His Asp
    50                  55                  60

Gln Val His Leu Leu Glu Cys Ala Trp Leu Glu Ile Leu Met Ile Gly
65                  70                  75                  80

Leu Val Trp Arg Ser Met Glu His Pro Val Lys Leu Leu Phe Ala Pro
                85                  90                  95

Asn Leu Leu Leu Asp Arg Asn Gln Gly Lys Cys Val Glu Gly Met Val
            100                 105                 110

Glu Ile Phe Asp Met Leu Leu Ala Thr Ser Ser Arg Phe Arg Met Met
        115                 120                 125

Asn Leu Gln Gly Glu Glu Phe Val Cys Leu Lys Ser Ile Ile Leu Leu
    130                 135                 140

Asn Ser Gly Val Tyr Thr Phe Leu Ser Ser Thr Leu Lys Ser Leu Glu
145                 150                 155                 160

Glu Lys Asp His Ile His Arg Val Leu Asp Lys Ile Thr Asp Thr Leu
                165                 170                 175

Ile His Leu Met Ala Lys Ala Gly Leu Thr Leu Gln Gln Gln His Gln
            180                 185                 190

Arg Leu Ala Gln Leu Leu Leu Ile Leu Ser His Ile Arg His Met Ser
        195                 200                 205

Asn Lys Gly Met Glu His Leu Tyr Ser Met Lys Cys Lys Asn Val Val
    210                 215                 220
```

```
Pro Leu Tyr Asp Leu Leu Leu Glu Met Leu Asp Ala His
225                 230                 235
```

<210> SEQ ID NO 27
<211> LENGTH: 314
<212> TYPE: PRT
<213> ORGANISM: Homo sapiens

<400> SEQUENCE: 27

```
Ser Ala Gly Asp Met Arg Ala Ala Asn Leu Trp Pro Ser Pro Leu Met
1               5                   10                  15

Ile Lys Arg Ser Lys Lys Asn Ser Leu Ala Leu Ser Leu Thr Ala Asp
            20                  25                  30

Gln Met Val Ser Ala Leu Leu Asp Ala Glu Pro Pro Ile Leu Tyr Ser
        35                  40                  45

Glu Tyr Asp Pro Thr Arg Pro Phe Ser Glu Ala Ser Met Met Gly Leu
    50                  55                  60

Leu Thr Asn Leu Ala Asp Arg Glu Leu Val His Met Ile Asn Trp Ala
65                  70                  75                  80

Lys Arg Val Pro Gly Phe Val Asp Leu Thr Leu His Asp Gln Val His
                85                  90                  95

Leu Leu Glu Cys Ala Trp Leu Glu Ile Leu Met Ile Gly Leu Val Trp
            100                 105                 110

Arg Ser Met Glu His Pro Val Lys Leu Leu Phe Ala Pro Asn Leu Leu
        115                 120                 125

Leu Asp Arg Asn Gln Gly Lys Cys Val Glu Gly Met Val Glu Ile Phe
    130                 135                 140

Asp Met Leu Leu Ala Thr Ser Ser Arg Phe Arg Met Met Asn Leu Gln
145                 150                 155                 160

Gly Glu Glu Phe Val Cys Leu Lys Ser Ile Ile Leu Leu Asn Ser Gly
                165                 170                 175

Val Tyr Thr Phe Leu Ser Ser Thr Leu Lys Ser Leu Glu Glu Lys Asp
            180                 185                 190

His Ile His Arg Val Leu Asp Lys Ile Thr Asp Thr Leu Ile His Leu
        195                 200                 205

Met Ala Lys Ala Gly Leu Thr Leu Gln Gln Gln His Gln Arg Leu Ala
    210                 215                 220

Gln Leu Leu Leu Ile Leu Ser His Ile Arg His Met Ser Asn Lys Gly
225                 230                 235                 240

Met Glu His Leu Tyr Ser Met Lys Cys Lys Asn Val Val Pro Leu Tyr
                245                 250                 255

Asp Leu Leu Leu Glu Met Leu Asp Ala His Arg Leu His Ala Pro Thr
            260                 265                 270

Ser Arg Gly Gly Ala Ser Val Glu Glu Thr Asp Gln Ser His Leu Ala
        275                 280                 285

Thr Ala Gly Ser Thr Ser Ser His Ser Leu Gln Lys Tyr Tyr Ile Thr
    290                 295                 300

Gly Glu Ala Glu Gly Phe Pro Ala Thr Val
305                 310
```

<210> SEQ ID NO 28
<211> LENGTH: 242
<212> TYPE: PRT
<213> ORGANISM: Homo sapiens

<400> SEQUENCE: 28

```
Ser Ser Tyr Phe Val Asn Ser Leu Phe Ser Lys Tyr Lys Thr Gly Glu
1               5                   10                  15

Ser Leu Arg Pro Asn Tyr Tyr Asp Cys Gly Phe Ala Gln Asp Leu Gly
            20                  25                  30

Gly Arg Pro Thr Val Val Tyr Gly Pro Ser Ser Gly Ser Phe Gln
        35                  40                  45

His Pro Ser Gln Ile Gln Glu Phe Tyr His Gly Pro Ser Ser Leu Ser
    50                  55                  60

Thr Ala Pro Tyr Gln Gln Asn Pro Cys Ala Val Ala Cys His Gly Asp
65                  70                  75                  80

Pro Gly Asn Phe Tyr Gly Tyr Asp Pro Leu Gln Arg Gln Ser Leu Phe
                85                  90                  95

Gly Ala Gln Asp Pro Asp Leu Val Gln Tyr Ala Asp Cys Lys Leu Ala
                100                 105                 110

Ala Ala Ser Gly Leu Gly Glu Glu Ala Glu Gly Ser Glu Gln Ser Pro
            115                 120                 125

Ser Pro Thr Gln Leu Phe Pro Trp Met Arg Pro Gln Ala Ala Ala Gly
    130                 135                 140

Arg Arg Arg Gly Arg Gln Thr Tyr Ser Arg Tyr Gln Thr Leu Glu Leu
145                 150                 155                 160

Glu Lys Glu Phe Leu Phe Asn Pro Tyr Leu Thr Arg Lys Arg Arg Ile
                165                 170                 175

Glu Val Ser His Ala Leu Gly Leu Thr Glu Arg Gln Val Lys Ile Trp
            180                 185                 190

Phe Gln Asn Arg Arg Met Lys Trp Lys Lys Glu Asn Asn Lys Asp Lys
        195                 200                 205

Phe Pro Ser Ser Lys Cys Glu Gln Glu Leu Glu Lys Gln Lys Leu
    210                 215                 220

Glu Arg Ala Pro Glu Ala Ala Asp Glu Gly Asp Ala Gln Lys Gly Asp
225                 230                 235                 240

Lys Lys
```

<210> SEQ ID NO 29
<211> LENGTH: 575
<212> TYPE: PRT
<213> ORGANISM: Artificial Sequence
<220> FEATURE:
<223> OTHER INFORMATION: Fusion protein
<220> FEATURE:
<221> NAME/KEY: misc_feature
<222> LOCATION: (554)..(554)
<223> OTHER INFORMATION: Xaa can be any naturally occurring amino acid
<220> FEATURE:
<221> NAME/KEY: misc_feature
<222> LOCATION: (571)..(571)
<223> OTHER INFORMATION: Xaa can be any naturally occurring amino acid

<400> SEQUENCE: 29

```
Met Gly Tyr Pro Tyr Asp Val Pro Asp Tyr Ala Thr Arg Ser Ala Gly
1               5                   10                  15

Asp Met Arg Ala Ala Asn Leu Trp Pro Ser Pro Leu Met Ile Lys Arg
            20                  25                  30

Ser Lys Lys Asn Ser Leu Ala Leu Ser Leu Thr Ala Asp Gln Met Val
        35                  40                  45

Ser Ala Leu Leu Asp Ala Glu Pro Pro Ile Leu Tyr Ser Glu Tyr Asp
    50                  55                  60
```

```
Pro Thr Arg Pro Phe Ser Glu Ala Ser Met Met Gly Leu Leu Thr Asn
 65                  70                  75                  80

Leu Ala Asp Arg Glu Leu Val His Met Ile Asn Trp Ala Lys Arg Val
             85                  90                  95

Pro Gly Phe Val Asp Leu Thr Leu His Asp Gln Val His Leu Leu Glu
            100                 105                 110

Cys Ala Trp Leu Glu Ile Leu Met Ile Gly Leu Val Trp Arg Ser Met
            115                 120                 125

Glu His Pro Val Lys Leu Leu Phe Ala Pro Asn Leu Leu Leu Asp Arg
        130                 135                 140

Asn Gln Gly Lys Cys Val Glu Gly Met Val Glu Ile Phe Asp Met Leu
145                 150                 155                 160

Leu Ala Thr Ser Ser Arg Phe Arg Met Met Asn Leu Gln Gly Glu Glu
                165                 170                 175

Phe Val Cys Leu Lys Ser Ile Ile Leu Leu Asn Ser Gly Val Tyr Thr
            180                 185                 190

Phe Leu Ser Ser Thr Leu Lys Ser Leu Glu Glu Lys Asp His Ile His
            195                 200                 205

Arg Val Leu Asp Lys Ile Thr Asp Thr Leu Ile His Leu Met Ala Lys
        210                 215                 220

Ala Gly Leu Thr Leu Gln Gln Gln His Gln Arg Leu Ala Gln Leu Leu
225                 230                 235                 240

Leu Ile Leu Ser His Ile Arg His Met Ser Asn Lys Gly Met Glu His
                245                 250                 255

Leu Tyr Ser Met Lys Cys Lys Asn Val Val Pro Leu Tyr Asp Leu Leu
            260                 265                 270

Leu Glu Met Leu Asp Ala His Arg Leu His Ala Pro Thr Ser Arg Gly
        275                 280                 285

Gly Ala Ser Val Glu Glu Thr Asp Gln Ser His Leu Ala Thr Ala Gly
        290                 295                 300

Ser Thr Ser Ser His Ser Leu Gln Lys Tyr Tyr Ile Thr Gly Glu Ala
305                 310                 315                 320

Glu Gly Phe Pro Ala Thr Val Thr Arg Gly Ser Ser Tyr Phe Val Asn
                325                 330                 335

Ser Leu Phe Ser Lys Tyr Lys Thr Gly Glu Ser Leu Arg Pro Asn Tyr
            340                 345                 350

Tyr Asp Cys Gly Phe Ala Gln Asp Leu Gly Gly Arg Pro Thr Val Val
        355                 360                 365

Tyr Gly Pro Ser Ser Gly Gly Ser Phe Gln His Pro Ser Gln Ile Gln
        370                 375                 380

Glu Phe Tyr His Gly Pro Ser Ser Leu Ser Thr Ala Pro Tyr Gln Gln
385                 390                 395                 400

Asn Pro Cys Ala Val Ala Cys His Gly Asp Pro Gly Asn Phe Tyr Gly
                405                 410                 415

Tyr Asp Pro Leu Gln Arg Gln Ser Leu Phe Gly Ala Gln Asp Pro Asp
            420                 425                 430

Leu Val Gln Tyr Ala Asp Cys Lys Leu Ala Ala Ala Ser Gly Leu Gly
            435                 440                 445

Glu Glu Ala Glu Gly Ser Glu Gln Ser Pro Ser Pro Thr Gln Leu Phe
        450                 455                 460

Pro Trp Met Arg Pro Gln Ala Ala Gly Arg Arg Gly Arg Gln Thr
465                 470                 475                 480
```

-continued

```
Tyr Ser Arg Tyr Gln Thr Leu Glu Leu Glu Lys Glu Phe Leu Phe Asn
            485                 490                 495

Pro Tyr Leu Asn Arg Lys Arg Arg Ile Glu Val Ser His Ala Leu Gly
            500                 505                 510

Leu Thr Glu Arg Gln Val Lys Ile Trp Phe Gln Asn Arg Arg Met Lys
            515                 520                 525

Trp Lys Lys Glu Asn Asn Lys Asp Lys Phe Pro Ser Ser Lys Cys Glu
530                 535                 540

Gln Glu Glu Leu Glu Lys Glu Lys Leu Xaa Arg Ala Pro Glu Thr Ala
545                 550                 555                 560

Glu Gln Gly Asp Ala Gln Lys Gly Asp Lys Xaa Val Val Thr Arg
            565                 570                 575

<210> SEQ ID NO 30
<211> LENGTH: 9
<212> TYPE: PRT
<213> ORGANISM: Artificial Sequence
<220> FEATURE:
<223> OTHER INFORMATION: HA tag

<400> SEQUENCE: 30

Tyr Pro Tyr Asp Val Pro Asp Tyr Ala
1               5

<210> SEQ ID NO 31
<211> LENGTH: 8
<212> TYPE: PRT
<213> ORGANISM: Artificial Sequence
<220> FEATURE:
<223> OTHER INFORMATION: FLAG tag

<400> SEQUENCE: 31

Asp Tyr Lys Asp Asp Asp Asp Lys
1               5

<210> SEQ ID NO 32
<211> LENGTH: 7
<212> TYPE: PRT
<213> ORGANISM: Artificial Sequence
<220> FEATURE:
<223> OTHER INFORMATION: EE epitope tag

<400> SEQUENCE: 32

Glu Glu Tyr Met Pro Met Glu
1               5
```